United States Patent
Julien et al.

(10) Patent No.: US 10,060,933 B2
(45) Date of Patent: Aug. 28, 2018

(54) METHODS FOR DIAGNOSIS AND TREATMENT OF AMYOTROPHIC LATERAL SCLEROSIS BASED ON AN INCREASED LEVEL OF INTERACTION BETWEEN TDP-43 POLYPEPTIDE AND NF-KB P65 POLYPEPTIDE

(71) Applicant: UNIVERSITE LAVAL, Quebec (CA)

(72) Inventors: Jean-Pierre Julien, Quebec (CA); Vivek Swarup, Quebec (CA)

(73) Assignee: UNIVERSITE LAVAL, Quebec (CA)

( * ) Notice: Subject to any disclaimer, the term of this patent is extended or adjusted under 35 U.S.C. 154(b) by 0 days.

(21) Appl. No.: 14/935,024

(22) Filed: Nov. 6, 2015

(65) Prior Publication Data

US 2016/0091504 A1    Mar. 31, 2016

Related U.S. Application Data

(63) Continuation of application No. 14/128,122, filed as application No. PCT/CA2012/050419 on Jun. 22, 2012.

(60) Provisional application No. 61/499,860, filed on Jun. 22, 2011.

(51) Int. Cl.

| | |
|---|---|
| *A61K 49/00* | (2006.01) |
| *G01N 33/53* | (2006.01) |
| *A61B 5/00* | (2006.01) |
| *A61K 39/395* | (2006.01) |
| *A61K 39/00* | (2006.01) |
| *A61K 38/00* | (2006.01) |
| *C07K 14/00* | (2006.01) |
| *C07K 7/00* | (2006.01) |
| *G01N 33/68* | (2006.01) |
| *C12Q 1/6883* | (2018.01) |
| *G01N 33/50* | (2006.01) |
| *C12N 15/113* | (2010.01) |
| *A61K 31/58* | (2006.01) |
| *A61K 31/7088* | (2006.01) |
| *A01K 67/027* | (2006.01) |
| *C07K 14/47* | (2006.01) |
| *C12N 15/85* | (2006.01) |
| *C07K 16/18* | (2006.01) |

(52) U.S. Cl.
CPC ..... *G01N 33/6896* (2013.01); *A01K 67/0275* (2013.01); *A61K 31/58* (2013.01); *A61K 31/7088* (2013.01); *C07K 14/4702* (2013.01); *C07K 16/18* (2013.01); *C12N 15/113* (2013.01); *C12N 15/8509* (2013.01); *C12Q 1/6883* (2013.01); *G01N 33/502* (2013.01); *A01K 2217/052* (2013.01); *A01K 2227/105* (2013.01); *A01K 2267/0312* (2013.01); *A01K 2267/0318* (2013.01); *C07K 2317/76* (2013.01); *C12N 2310/14* (2013.01); *C12Q 2600/112* (2013.01); *C12Q 2600/158* (2013.01); *G01N 2333/4703* (2013.01); *G01N 2333/4704* (2013.01); *G01N 2500/00* (2013.01); *G01N 2800/28* (2013.01); *G01N 2800/2835* (2013.01); *G01N 2800/50* (2013.01); *G01N 2800/56* (2013.01)

(58) Field of Classification Search
CPC .......................... C07K 16/18; C07K 14/4702; C07K 2317/76; C07K 2317/24; C07K 2317/35; C07K 2317/52; C07K 2317/54; C07K 2317/55; C07K 2317/569; C07K 14/4703; C07K 2319/00; C12N 2310/14; G01N 2500/00; G01N 2800/28; G01N 2800/2835; G01N 2800/50; G01N 2800/56; G01N 33/6896; G01N 2333/4703; G01N 2333/4704; C12Q 1/6883; C12Q 1/6809; C12Q 2600/112; C12Q 2600/158; A61K 38/00; A61K 39/00; A01K 2217/052; A01K 2267/0318
See application file for complete search history.

(56) References Cited

U.S. PATENT DOCUMENTS

| | | | |
|---|---|---|---|
| 8,598,339 B2 | 12/2013 | Timmermann et al. | |
| 8,715,643 B2* | 5/2014 | Nonaka | C07K 14/4711 424/93.2 |
| 8,889,597 B2* | 11/2014 | Cairns | C12Q 1/6883 435/6.1 |
| 8,940,872 B2* | 1/2015 | Hasegawa | C07K 16/18 530/387.9 |
| 2002/0106689 A1* | 8/2002 | Faustman | C07K 14/4702 435/7.1 |
| 2003/0143540 A1 | 7/2003 | Matsuda et al. | |

(Continued)

FOREIGN PATENT DOCUMENTS

| | | |
|---|---|---|
| EP | 2189526 A1 | 5/2010 |
| WO | 2004/110364 A2 | 12/2004 |

(Continued)

OTHER PUBLICATIONS

Hart et al. Curr. Opin. Neurol. 2003. 16: 375-383.*

(Continued)

*Primary Examiner* — Chang-Yu Wang
(74) *Attorney, Agent, or Firm* — Seed IP Law Group LLP

(57) ABSTRACT

The present invention provides methods and uses for the diagnostic of a subject predisposed or suspected of developing a neurodegenerative disease or suffering from a neurodegenerative disease. The present invention also relates to methods and uses for identifying candidate compounds and to compounds for treating neurodegenerative disease. The present invention also relates to an animal model for neurodegenerative disease.

11 Claims, 35 Drawing Sheets
Specification includes a Sequence Listing.

(56) References Cited

U.S. PATENT DOCUMENTS

| | | | |
|---|---|---|---|
| 2009/0263824 A1 | 10/2009 | Lee et al. | |
| 2010/0136573 A1* | 6/2010 | Petrucelli | C07K 14/4711 435/7.1 |
| 2011/0034447 A1 | 2/2011 | Nonaka et al. | |
| 2011/0053857 A1* | 3/2011 | Lindquist | C12N 15/1079 514/17.7 |
| 2011/0065600 A1 | 3/2011 | Cairns et al. | |
| 2011/0230551 A1 | 9/2011 | Gunatilaka et al. | |
| 2011/0287953 A1 | 11/2011 | Huang et al. | |
| 2012/0196815 A1 | 8/2012 | Timmermann et al. | |
| 2013/0338039 A1 | 12/2013 | Mazed et al. | |
| 2014/0120562 A1* | 5/2014 | Julien | C12Q 1/6883 435/7.92 |

FOREIGN PATENT DOCUMENTS

| | | | |
|---|---|---|---|
| WO | 2008/042190 A2 | 4/2008 | |
| WO | 2008/151055 A1 | 12/2008 | |
| WO | WO 2008151055 A1 * | 12/2008 | C07K 14/4711 |
| WO | 2009/008529 A1 | 1/2009 | |
| WO | 2009/044119 A1 | 4/2009 | |
| WO | WO 2009099941 A2 * | 8/2009 | C12Q 1/6883 |
| WO | 2010/015040 A1 | 2/2010 | |
| WO | 2010/030395 A2 | 3/2010 | |
| WO | 2010/053655 A2 | 5/2010 | |
| WO | 2011/005628 A1 | 1/2011 | |
| WO | 2011/151359 A1 | 12/2011 | |

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Aleyasin et al. "Nuclear factor-(kappa)B modulates the p53 response in neurons exposed to DNA damage", J Neurosci 24, 2963-2973 (2004).
Arai et al."TDP-43 is a component of ubiquitin-positive tau-negative inclusions in frontotemporal lobar degeneration and amyotrophic lateral sclerosis", Biochem Biophys Res Commun 351, 602-611 (2006).
Badadani et al. "VCP associated inclusion body myopathy and paget disease of bone knock-in mouse model exhibits tissue pathology typical of human disease", PLoS One 5, e13183 (2010).
Barbeito et al. "A role for astrocytes in motor neuron loss in amyotrophic lateral sclerosis", Brain Res Rev 47:263-74 (2004).
Baumer, D. et al. "TARDBP in amyotrophic lateral sclerosis: identification of a novel variant but absence of copy number variation", J Neurol Neurosurg Psychiatry 80, 1283-1285 (2009).
Beaulieu et al. "Late onset of motor neurons in mice overexpressing wild-type peripherin", J Cell Biol 147:531-44 (1999).
Beaulieu et al. "Induction of peripherin expression in subsets of brain neurons after lesion injury or cerebral ischemia", Brain Res 946:153-61 (2002).
Bergmann et al. "IkappaBalpha degradation and nuclear factor-kappaB DNA binding are insufficient for interleukin-1beta and tumor necrosis factor-alpha-induced kappaB-dependent transcription. Requirement for an additional activation pathway", J Biol Chem 273, 6607-6610 (1998).
Boillee et al. "ALS: a disease of motor neurons and their non-neuronal neighbors", Neuron 52, 39-59 (2006).
Boillee et al."Onset and progression in inherited ALS determined by motor neurons and microglia", Science 312, 1389-1392 (2006).
Bose et al. "TDP-43 overexpression enhances exon 7 inclusion during the survival of motor neuron pre-mRNA splicing", J Biol Chem 283:28852-9 (2008).
Buratti et al. "Nuclear factor TDP-43 and SR proteins promote in vitro and in vivo CFTR exon 9 skipping",EMBO J 20:1774-84 (2001).
Cairns et al. "TDP-43 in familial and sporadic frontotemporal lobar degeneration with ubiquitin inclusions" Am J Pathol; 171:227-40 (2007).

Carpenter "Proximal axonal enlargement in motor neuron disease" Neurology 18:841-51 (1968).
Cassel et al. "Development of a novel nonradiometric assay for nucleic acid binding to TDP-43 suitable for high-throughput screening using AlphaScreen technology", J. Biomol Screen, 15, 1099-1106 (2010).
Chiang et al. "Deletion of TDP-43 down-regulates Tbc 1d1, a gene linked to obesity, and alters body fat metabolism", Proc Natl Acad Sci USA, 107, 16320-16324, (2010).
Clement et al. "Wild-type nonneuronal cells extend survival of SOD1 mutant motor neurons in ALS mice", Science 302, 113-117 (2003).
Corbo et al. "Peripherin and neurofilament protein coexist in spinal spheroids of motor neuron disease", J Neuropathol Exp Neurol 51:531-7 (1992).
Cordeau et al. "Live imaging of neuroinflammation reveals sex and estrogen effects on astrocyte response to ischemic injury", Stroke 39, 935-942 (2008).
Corrado et al. "High frequency of TARDBP gene mutations in Italian patients with amyotrophic lateral sclerosis", Hum Mutat 30, 688-694 (2009).
Custer et al."Transgenic mice expressing mutant forms VCP/p97 recapitulate the full spectrum of IBMPFD including degeneration in muscle, brain and bone", Hum Mol Genet 19, 1741-1755 (2010).
Daoud et al."Contribution of TARDBP mutations to sporadic amyotrophic lateral sclerosis", J Med Genet 46, 112-114 (2009).
Davies et al."Isolation and culture of murine macrophages.", Methods Mol Biol 290, 91-103 (2005).
Deng, H.X., et al. "FUS-immunoreactive inclusions are a common feature in sporadic and non-SOD1 familial amyotrophic lateral sclerosis", Ann Neurol 67, 739-748 (2010).
Dequen et al. "Modest loss of peripheral axons, muscle atrophy and formation of brain inclusions in mice with targeted deletion of gigaxonin exon 1",. J Neurochem 107, 253-264 (2008).
Di Giorgio et al. "Non-cell autonomous effect of glia on motor neurons in an embryonic stem cell-based ALS model", Nat Neurosci 10:608-14. (2007).
Di Giorgio et al. "Human embryonic stem cell-derived motor neurons are sensitive to the toxic effect of glial cells carrying an ALS-causing mutation", Cell Stem Cell 3:637-48 (2008).
Dormann et al. "Proteolytic processing of TAR DNA binding protein-43 by caspases produces C-terminal fragments with disease defining properties independent of progranulin", J Neurochem 110, 1082-1094 (2009).
Douville et al., "Identification of active loci of a human endogenous retrovirus in neurons of patients with amyotrophic lateral sclerosis", Ann Neurol 69, 141-151 (2011).
Dreyfuss et al. "hnRNP proteins and the biogenesis of mRNA", Annu Rev Biochem 62, 289-321 (1993).
Forman et al. "TDP-43: a novel neurodegenerative proteinopathy", Curr Opin Neurobiol 17:548-55 (2007).
Gerritsen et al. "CREB-binding protein/p300 are transcriptional coactivators of p65", Proc Natl Acad Sci USA 94, 2927-2932 (1997).
Gitcho et al. "TDP-43 A315T mutation in familial motor neuron disease". Ann Neurol 63, 535-538 (2008).
Gitcho et al. "TARDBP 3'-UTR variant in autopsy-confirmed frontotemporal lobar degeneration with TDP-43 proteinopathy", Acta Neuropathol 118, 633-645 (2009).
Gros-Louis et al. "Als2 mRNA splicing variants detected in KO mice rescue severe motor dysfunction phenotype in Als2 knock-down zebrafish", Hum Mol Genet 17, 2691-2702 (2008).
Guerreiro et al. "TDP-43 is not a common cause of sporadic amyotrophic lateral sclerosis", PLoS One 3, e2450 (2008).
Hodges et al. "Clinicopathological correlates in frontotemporal dementia", Ann Neurol 56:399-406 (2004).
Horvath et al., "Differential migration, LPS-induced cytokine, chemokine, and NO expression in immortalized BV-2 and HAPI cell lines and primary microglial cultures", J Neurochem 107, 557-569 (2008).
Igaz et al. "Expression of TDP-43 C-terminal Fragments in Vitro Recapitulates Pathological Features of TDP-43 Proteinopathies", J Biol Chem 284, 8516-8524 (2009).

(56) References Cited

OTHER PUBLICATIONS

Johnson et al. "A yeast TDP-43 proteinopathy model: Exploring the molecular determinants of TDP-43 aggregation and cellular toxicity", Proc Natl Acad Sci USA 105, 6439-6444 (2008).
Johnson et al. "Exome sequencing reveals VCP mutations as a cause of familial ALS", Neuron 68, 857-864 (2010).
Julien "ALS: astrocytes move in as deadly neighbors", Nat Neurosci 10:535-7 (2007).
Kabashi et al. "TARDBP mutations in individuals with sporadic and familial amyotrophic lateral sclerosis", Nat Genet 40, 572-574 (2008).
Kasai et al. "Increased TDP-43 protein in cerebrospinal fluid of patients with amyotrophic lateral sclerosis", Acta Neuropathol 117, 55-62 (2009).
Keller et al. "Empirical statistical model to estimate the accuracy of peptide identifications made by MS/MS and database search", Anal Chem 74, 5383-5392 (2002).
Keller et al. "Live imaging of amyotrophic lateral sclerosis pathogenesis: disease onset is characterized by marked induction of GFAP in Schwann cells", Glia 57:1130-42 (2009).
Keller et al. "Treatment with minocycline after disease onset alters astrocyte reactivity and increases microgliosis in SOD1 mutant mice", Exp Neurol, 228, 69-79 (2011).
Kriz et al. "Altered ionic conductances in axons of transgenic mouse expressing the human neurofilament heavy gene: A mouse model of amyotrophic lateral sclerosis", Exp Neurol 163:414-21 (2000).
Kwiatkowski et al. "Mutations in the FUS/TLS gene on chromosome 16 cause familial amyotrophic lateral sclerosis", Science 323, 1205-1208 (2009).
Lagier-Tourenne et al. "Rethinking ALS: the FUS about TDP-43" Cell 136:1001-4 (2009).
Ling et al. "ALS-associated mutations in TDP-43 increase its stability and promote TDP-43 complexes with FUS/TLS", Proc Natl Acad Sci USA 107, 13318-13323 (2010).
Lomen-Hoerth et al. "Are amyotrophic lateral sclerosis patients cognitively normal?", Neurology 60:1094-7 (2003).
Lu et al "A method to solubilise protein aggregates for immunoassay quantification which overcomes the neurofilament "hook" effect", J Neurosci Methods 195:143-50 (2011).
Maruyama et al. "Mutations of optineurin in amyotrophic lateral sclerosis", Nature 465, 223-226 (2010).
Maysinger et al. "Real-time imaging of astrocyte response to quantum dots: in vivo screening model system for biocompatibility of nanoparticles", Nano Lett 7, 2513-2520 (2007).
Mercado et al "Depletion of TDP 43 overrides the need for exonic and intronic splicing enhancers in the human apoA-II gene", Nucleic Acids Res 33:6000-10 (2005).
Migheli et al. "Peripherin immunoreactive structures in amyotrophic lateral sclerosis", Lab Invest 68:185-91 (1993).
Nagai et al. "Astrocytes expressing ALS-linked mutated SOD1 release factors selectively toxic to motor neurons", Nat Neurosci 10:615-22 (2007).
Neumann et al. "Ubiquitinated TDP-43 in frontotemporal lobar degeneration and amyotrophic lateral sclerosis", Science 314, 130-133 (2006).
Neumann et al., "Molecular Neuropathology of TDP-43 Proteinopathies," *Int. J. Mol. Sci.* 10:232-246 (2009).
Noto et al. "Elevated CSF TDP-43 levels in amyotrophic lateral sclerosis: Specificity, sensitivity, and a possible prognostic value", Amyotroph Lateral Scler, 12, 140-143 (2011).
Oh et al. "Withaferin A inhibits iNOS expression and nitric oxide production by Akt inactivation and down-regulating LPS-induced activity of NF-kappaB in RAW 264.7 cells", Eur J Pharmacol 599, 11-17 (2008).
Ou et al. "Cloning and characterization of a novel cellular protein, TDP-43, that binds to human immunodeficiency virus type 1 TAR DNA sequence motifs", J Virol 69:3584-96 (1995).
Perkins et al. "Regulation of NF-kappaB by cyclin-dependent kinases associated with the p300 coactivator", Science 275, 523-527 (1997).
Pizzi et al. "Inhibition of IkappaBalpha phosphorylation prevents glutamate-induced NF-kappaB activation and neuronal cell death", Acta Neurochir Suppl 93, 59-63 (2005).
Pizzi et al., "Distinct roles of diverse nuclear factor-κB complexes in neuropathological mechanisms," *European Journal of Pharmacology* 545:22-28, 2006.
Polymenidou et al. "Long pre-mRNA depletion and RNA missplicing contribute to neuronal vulnerability from loss of TDP-43", Nat Neurosci 14:459-68 (2011).
Prut et al. "Aged APP23 mice show a delay in switching to the use of a strategy in the Barnes maze" Behav Brain Res 179:107-10 (2007).
Robertson et al. "A neurotoxic peripherin splice variant in a mouse model of ALS", J Cell Biol 160:939-49 (2003).
Rutherford et al. "Novel mutations in TARDBP (TDP-43) in patients with familial amyotrophic lateral sclerosis", PLoS Genet 4:e1000193 (2008).
Sanelli et al. "Evidence that TDP-43 is not the major ubiquitinated target within the pathological inclusions of amyotrophic lateral sclerosis", Journal of neuropathology and experimental neurology 66:1147-53 (2007).
Schmitz et al. "Interaction of the COOH-terminal transactivation domain of p65 NF-kappa B with TATA-binding protein, transcription factor IIB, and coactivators", J Biol Chem 270, 7219-7226 (1995).
Schmitz et al. "Transactivation domain 2 (TA2) of p65 NF-kappa B. Similarity to TA1 and phorbol ester-stimulated activity and phosphorylation in intact cells", J Biol Chem 270, 15576-15584 (1995).
Schwartz et al., "Microglia activation in multiple system atrophy: a potential role for NF-κB/rel proteins," *NeuroReport* 9(13):3029-3032, 1998.
Seeley "Selective functional, regional, and neuronal vulnerability in frontotemporal dementia", Curr Opin Neurol 21:701-7 (2008).
Sephton et al. "TDP-43 is a developmentally regulated protein essential for early embryonic development", J Biol Chem 285, 6826-6834 (2010).
Seyfried et al. "Multiplex SILAC analysis of a cellular TDP-43 proteinopathy model reveals protein inclusions associated with SUMOylation and diverse polyubiquitin chains", Mol Cell Proteomics 9, 705-718 (2010).
Sheppard et al. "Transcriptional activation by NF-kappaB requires multiple coactivators", Mol Cell Biol 19, 6367-6378 (1999).
Sreedharan et al. "TDP-43 mutations in familial and sporadic amyotrophic lateral sclerosis", Science 319, 1668-1672 (2008).
Stallings et al. "Generation and characterization of wild-type and mutant TDP-43 transgenic mice", Society For Neuroscience, Abstract Book 2009 (2009).
Stallings et al. "Progressive motor weakness in transgenic mice expressing human TDP-43", Neurobiol Dis, 40, 404-414 (2010).
Sterneck et al. "Interleukin-6 induces expression of peripherin and cooperates with Trk receptor signaling to promote neuronal differentiation in PC12 cells", J Neurochem 67:1365-74 (1996).
Swarup et al."Tumor necrosis factor receptor-1-induced neuronal death by TRADD contributes to the pathogenesis of Japanese encephalitis", J Neurochem 103, 771-783 (2007).
Swarup et al. "Japanese encephalitis virus infection decrease endogenous IL-10 production: correlation with microglial activation and neuronal death", Neurosci Lett 420, 144-149 (2007).
Swarup et al., "ALS pathosgenesis: Recent insights from genetics and mouse models," *Progress in Neuro-Psychopharmacology & Biological Psychiatry* 35:363-369, 2011.
Swarup et al., "Deregulation of TDP-43 in amyotrophic lateral sclerosis triggers nuclear factor κB-mediated pathogenic pathways," *The Journal of Experimental Medicine* 208(12):2429-2447, 2011.
Suzuki et al. "Increased expression of TDP-43 in the skin of amyotrophic lateral sclerosis", Acta Neurol Scand, 122, 367-372 (2010).
T Hart et al., "The use of animal models to investigate the pathogenesis of neuroinflammatory disorders of the central nervous system," *Current Opinion in Neurolology* 16:375-383 (2003).

(56) References Cited

OTHER PUBLICATIONS

Talbot et al. "Recent advances in the genetics of amyotrophic lateral sclerosis and frontotemporal dementia: common pathways in neurodegenerative disease", Hum Mol Genet 15 Spec No. 2:R182-7 (2006).

Thaiparambil et al. "Withaferin A inhibits breast cancer invasion and metastasis at sub-cytotoxic doses by inducing vimentin disassembly and serine 56 phosphorylation", Int J Cancer, 129, 2744-2755 (2011).

Vance et al. "Mutations in FUS, an RNA processing protein, cause familial amyotrophic lateral sclerosis type 6", Science 323, 1208-1211 (2009).

Van Deerlin et al. "TARDBP mutations in amyotrophic lateral sclerosis with TDP-43 neuropathology: a genetic and histopathological analysis", Lancet Neurol 7:409-16 (2008).

Voigt et al. "TDP-43-mediated neuron loss in vivo requires RNA-binding activity",PLoS One 5, e12247 (2010).

Wegorzewska et al."TDP-43 mutant transgenic mice develop features of ALS and frontotemporal lobar degeneration", Proc Natl Acad Sci USA 106, 18809-18814 (2009).

Weydt et al. "Increased cytotoxic potential of microglia from ALS-transgenic mice", Glia 48, 179-182 (2004).

Wils et al. "TDP-43 transgenic mice develop spastic paralysis and neuronal inclusions characteristic of ALS and frontotemporal lobar degeneration", Proc Natl Acad Sci USA 107, 3858-3863 (2010).

Wong et al. "Characterization of neuronal intermediate filament protein expression in cervical spinal motor neurons in sporadic amyotrophic lateral sclerosis (ALS)", J Neuropathol Exp Neurol 59:972-82 (2000).

Xiao et al. "An aggregate-inducing peripherin isoform generated through intron retention is upregulated in amyotrophic lateral sclerosis and associated with disease pathology", J Neurosci 28:1833-40 (2008).

Xu et al. "Wild-Type Human TDP-43 Expression Causes TDP-43 Phosphorylation, Mitochondrial Aggregation, Motor Deficits, and Early Mortality in Transgenic Mice", J Neurosci 30, 10851-10859 (2010).

Yokoseki et al. "TDP-43 mutation in familial amyotrophic lateral sclerosis" Ann Neurol 63:538-42 (2008).

Yoza et al. "Protein-tyrosine kinase activation is required for lipopolysaccharide induction of interleukin 1beta and NFkappaB activation, but not NFkappaB nuclear translocation", J Biol Chem 271, 18306-18309 (1996).

Yum et al. "A novel recessive Nefl mutation causes a severe, early-onset axonal neuropathy" Ann Neurol 66:759-70 (2009).

Zhang et al. "Aberrant cleavage of TDP-43 enhances aggregation and cellular toxicity", Proc Natl Acad Sci USA 106, 7607-7612 (2009).

Zhang et al. "Circulating endotoxin and systemic immune activation in sporadic amyotrophic lateral sclerosis (sALS)", J Neuroimmunol 206, 121-124 (2009).

Zhang et al. "Gene expression profiling in peripheral blood mononuclear cells from patients with sporadic amyotrophic lateral sclerosis (sALS)", J Neuroimmunol 230, 114-123 (2011).

\* cited by examiner

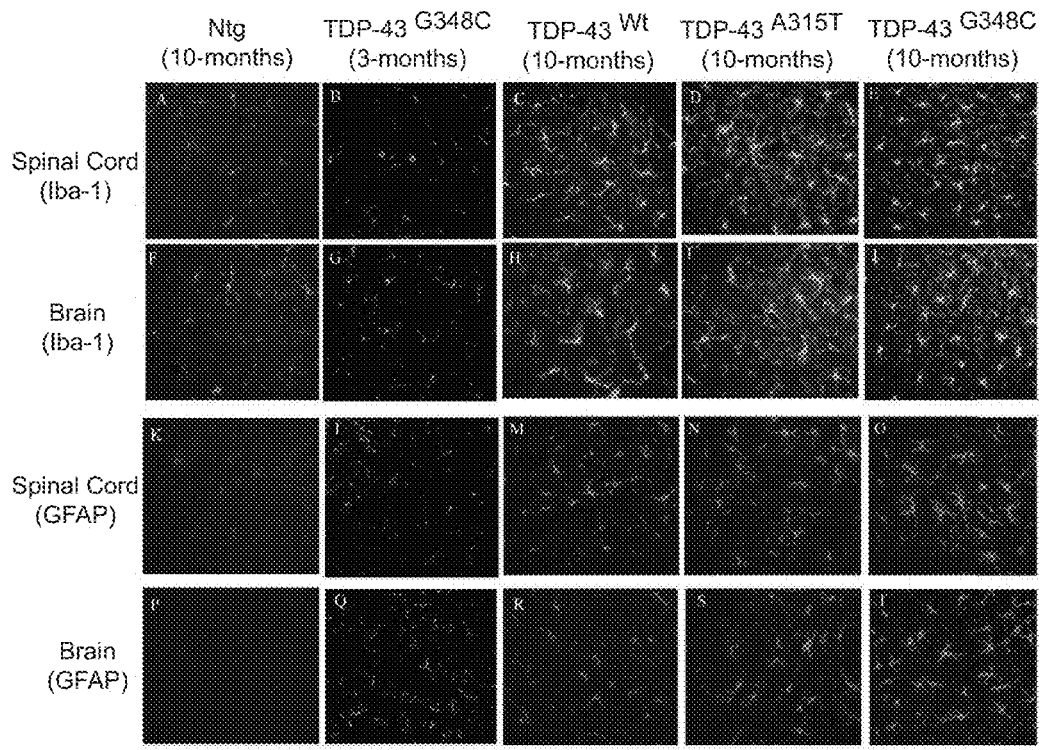
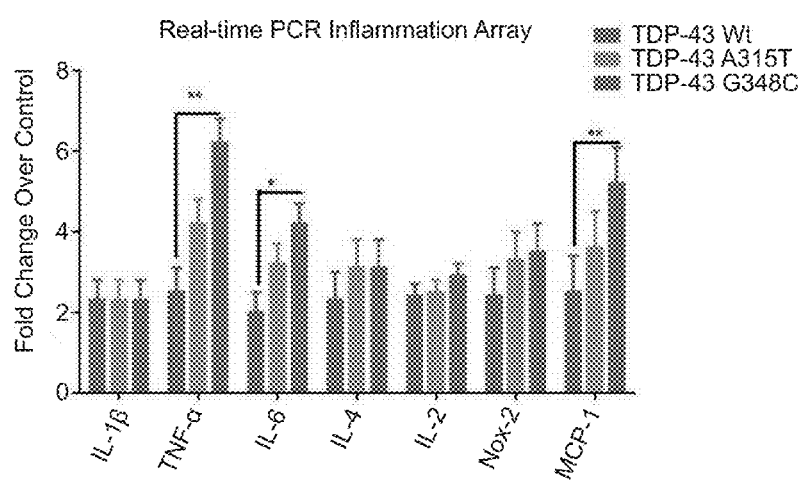
FIG. 23

METHODS FOR DIAGNOSIS AND TREATMENT OF AMYOTROPHIC LATERAL SCLEROSIS BASED ON AN INCREASED LEVEL OF INTERACTION BETWEEN TDP-43 POLYPEPTIDE AND NF-ΚB P65 POLYPEPTIDE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920136_401C1_SEQUENCE_LISTING.txt. The text file is 18.1 KB was created on Nov. 3, 2015, and is being submitted electronically via EFS-Web.

BACKGROUND

The present invention relates to methods for the prognostic and diagnostic of neurodegenerative disease, kits related to such methods and methods to identify candidate compounds for preventing and treating neurodegenerative disease.

Amyotrophic lateral sclerosis (ALS) is an adult-onset neurodegenerative disorder characterized by the progressive degeneration of motor neurons in the brain and spinal cord. Approximately 10% of ALS cases are familial and 90% are sporadic. Recently, TAR DNA binding protein 43 (TDP-43) has been implicated in ALS[1]. TDP-43 is a DNA/RNA-binding 43 kDa protein that contains a N-terminal domain, two RNA recognition motifs (RRMs) and a glycine-rich C-terminal domain, characteristic of the heterogeneous nuclear ribonucleoprotein (hnRNP) class of proteins[2]. TDP-43, normally observed in the nucleus, is detected in pathological inclusions in the cytoplasm and nucleus of both neurons and glial cells of ALS and frontotemporal lobar degeneration with ubiquitin inclusions (FTLD-U) cases[1, 3]. The inclusions consist prominently of TDP-43 C-terminal fragments (CTFs) of ~25 kDa. The involvement of TDP-43 with ALS cases led to the discovery of TDP-43 mutations found in ALS patients. Dominant mutations in TARDBP, which codes for TDP-43, were reported by several groups as a primary cause of ALS[4-9] and may account for ~3% of familial ALS cases and ~1.5% of sporadic cases.

Neuronal overexpression at high levels of wild-type or mutant TDP-43 in transgenic mice caused a dose-dependent degeneration of cortical and spinal motor neurons but with no cytoplasmic TDP-43 aggregates[10-13], raising up the possibility that an upregulation of TDP-43 in the nucleus rather than TDP-43 cytoplasmic aggregates may contribute to neurodegeneration. The physiological role of TDP-43 and the pathogenic pathways of TDP-43 abnormalities are not well understood. TDP-43 is essential for embryogenesis[14] and postnatal deletion of the TDP-43 gene in mice caused downregulation of Tbc1d1, a gene that alters body fat metabolism[15]. Proteins known to interact with TDP-43 have also been implicated in protein refolding or proteasomal degradation including ubiquitin, proteasome-beta subunits, SUMO-2/3 and Hsp70[16].

Because TDP-43 is ubiquitously expressed and several studies have supported the importance of glial cells in mediating motor neuron injury[17-19], additional proteins which might interact with TDP-43 in LPS-stimulated microglial (BV-2) cells were searched. The rationale for choosing microglial BV-2 cells was that TDP-43 deregulation may occur not only in neurons but also in microglial cells. Moreover, there are recent reports of increased levels of LPS in the blood of ALS patients[20] and of an upregulation of LPS/TLR-4 signaling associated genes in peripheral blood monocytes from ALS patients[21]. Accordingly, the search was biased for proteins interacting with TDP-43 when microglia are activated by LPS. Surprisingly, co-immunoprecipitation assays and mass spectrometry led us to identify the p65 subunit of NF-κB as a binding partner of TDP-43. Furthermore, the results show that TDP-43 mRNA was abnormally upregulated in the spinal cord of ALS subjects. These results reported here led to further explore the physiological significance of the interaction between TDP-43 and p65 NF-κB.

As the symptoms of ALS are similar to those of other neuromuscular disorders, many of which are treatable, ALS is difficult to diagnose. The diagnosis is usually based on a complete neurological examination and clinical tests.

There is therefore a need for methods for evaluating a subject predisposed to developing a neurodegenerative disease such as ALS and FTLD-U or suffering from these neurodegenerative diseases as well as method to identify new candidate compounds useful for the prevention and/or treatment of neurodegenerative diseases.

The present inventors have surprisingly found an interaction between TDP-43 and p65 NF-κB in subjects suffering from a neurodegenerative disease. The present inventors have also found that levels of TDP-43 and p65 mRNA are elevated in subjects suffering from a neurodegenerative disease.

The present invention relates to methods measuring or evaluating interaction between TDP-43 and p65 for diagnosis, prognosis, monitoring the progression of the disease or for identifying drug candidates.

The present invention also relates to measuring the level of TDP-43 and/or p65 mRNA.

Kits for measuring the interaction between TDP-43 and p65 and for measuring the levels of TDP-43 and p65 mRNA are also provided by the present invention.

The present invention also relates to the use of the interaction level between TDP-43 and p65 as a biochemical marker for monitoring the progression or the regression of a neurological disease.

The present invention also relates to a method for the diagnostic of a subject predisposed or suspected of developing a neurodegenerative disease or suffering from a neurodegenerative disease, the method comprising the step of:
  determining the level of interaction between a TDP-43 polypeptide or fragment thereof and a p65 polypeptide or fragment thereof in a biological sample of the subject,
wherein observing an elevated level of interaction between TDP-43 polypeptide or fragment thereof and p65 polypeptide or fragment thereof in the biological sample relative to a reference level of interaction between TDP-43 polypeptide or fragment thereof and p65 polypeptide or fragment thereof indicates that the subject is predisposed or suspected of developing a neurodegenerative disease or is suffering from a neurodegenerative disease.

The present invention also relates to a method for the diagnostic of a subject predisposed or suspected of developing a neurodegenerative disease or suffering from a neurodegenerative disease, the method comprising the steps of:
  contacting a TDP-43 polypeptide or fragment thereof with a TDP-43 agent in a biological sample of the subject;
  contacting a p65 polypeptide or fragment thereof with a p65 agent in the biological sample; and detecting the TDP-43 agent and/or the p65 agent to determine the level of interaction between the TDP-43 polypeptide or fragment thereof and the p65 polypeptide or fragment thereof, wherein detecting an elevated level of interaction between TDP-43 polypeptide or fragment thereof and p65 polypeptide or fragment thereof in the biological sample relative to a reference level of interaction between TDP-43 polypeptide or fragment thereof and p65 polypeptide or fragment thereof indicates that the subject is predisposed or suspected of developing a neurodegenerative disease or is suffering from a neurodegenerative disease.

The present invention also relates to a method for the diagnostic of a subject predisposed or suspected of developing a neurodegenerative disease or suffering from a neurodegenerative disease, the method comprising the step of:

determining the level of TDP-43 mRNA in a biological sample of the subject, wherein observing an elevated level of TDP-43 mRNA in the biological sample relative to the reference level of TDP-43 mRNA indicates that the subject is predisposed or suspected of developing a neurodegenerative disease or is suffering from a neurodegenerative disease.

The present invention also relates to a method for the diagnostic of a subject predisposed or suspected of developing a neurodegenerative disease or suffering from a neurodegenerative disease, the method comprising the steps of:

isolating TDP-43 mRNA from a biological sample of a subject; and detecting the level of TDP-43 mRNA in the biological sample of the subject, wherein detecting an elevated level of TDP-43 mRNA in the biological sample relative to the reference level of TDP-43 mRNA indicates that the subject is predisposed or suspected of developing a neurodegenerative disease or is suffering from a neurodegenerative disease.

The present invention also relates to a kit for the diagnostic of a subject predisposed to or suspected of developing a neurodegenerative disease or suffering from a neurodegenerative disease, the kit comprising:

i) at least one TDP-43 specific antibody or fragment thereof;

ii) at least one p65 specific antibody or fragment thereof;

iii) a reference corresponding to the level of interaction between TDP-43 polypeptide or fragment thereof and p65 polypeptide or fragment thereof, iv) a container, and v) a buffer or an appropriate reagent.

The present invention also relates to a kit for the diagnostic of a subject predisposed to developing a neurodegenerative disease or suffering from a neurodegenerative disease, the kit comprising:

i) at least one set of specific primers for determining the level of TDP-43 mRNA;

ii) a reference corresponding to the level of TDP-43 mRNA, iii) a container, and iv) a buffer or an appropriate reagent.

The present invention also relates to a method for identifying a candidate compound useful for preventing and/or treating a neurodegenerative disease, the method comprising the steps of:

a) contacting the candidate compound with a biological system comprising TDP-43 polypeptide or fragment thereof and p65 polypeptide or fragment thereof, b) measuring the ability of the candidate compound to modulate the activation of NF-κB p65 in the biological system, and c) determining if the candidate compound is useful for preventing and/or treating a neurodegenerative disease based on the result of step b).

The present invention also relates to a method for identifying a candidate compound useful for preventing and/or treating a neurodegenerative disease, the method comprising the steps of:

a) contacting the candidate compound with a biological system comprising TDP-43 polypeptide or fragment thereof and p65 polypeptide or fragment thereof b) measuring the ability of the candidate compound to reduce or inhibit the interaction between TDP-43 polypeptide or fragment thereof and p65 polypeptide or fragment thereof, and c) determining if the candidate compound is useful for preventing and/or treating a neurodegenerative disease based on the result of step a).

The present invention also relates to a method for monitoring the progression or the regression of a neurodegenerative disease in a subject, the method comprising the step of:

determining the level of interaction between a TDP-43 polypeptide or fragment thereof and a p65 polypeptide or fragment thereof in a biological sample of the subject, wherein observing an increased level of interaction between TDP-43 polypeptide or fragment thereof and p65 polypeptide or fragment thereof indicates a progression of the neurodegenerative disease and wherein observing a decreased level of interaction between TDP-43 polypeptide or fragment thereof and p65 polypeptide or fragment thereof indicates a regression of the neurodegenerative disease.

The present invention also relates to a method for monitoring the progression or the regression of a neurodegenerative disease in a subject, the method comprising the steps of:

contacting a TDP-43 polypeptide or fragment thereof with a TDP-43 agent in a biological sample of the subject;

contacting a p65 polypeptide or fragment thereof with a p65 agent in the biological sample; and detecting the TDP-43 agent and/or the p65 agent to determine the level of interaction between the TDP-43 polypeptide or fragment thereof and the p65 polypeptide or fragment thereof;

wherein detecting an increased level of interaction between TDP-43 polypeptide or fragment thereof and p65 polypeptide or fragment thereof indicates a progression of the neurodegenerative disease and wherein observing a decreased level of interaction between TDP-43 polypeptide or fragment thereof and p65 polypeptide or fragment thereof indicates a regression of the neurodegenerative disease.

The present invention also relates to a use of the interaction level between a TDP-43 polypeptide or fragment thereof and p65 polypeptide or fragment thereof in a biological sample as a biochemical marker for monitoring the progression or the regression of a neurodegenerative disease in a subject.

The present invention also relates to a use of at least one TDP-43 interacting compound or a pharmaceutically acceptable salt thereof for treating a subject suffering from a neurodegenerative disease.

The present invention also relates to a use of a pharmaceutical composition comprising at least one TDP-43 interacting compound or a pharmaceutically acceptable salt thereof and a pharmaceutical acceptable carrier for treating a subject suffering from a neurodegenerative disease.

The present invention also relates to use of at least one withanolide compound or pharmaceutically acceptable salt thereof for treating a subject suffering from a neurodegenerative disease.

The present invention also relates to a use of a pharmaceutical composition comprising at least one withanolide compound or a pharmaceutically acceptable salt thereof and a pharmaceutical acceptable carrier for treating a subject suffering from a neurodegenerative disease.

The present invention also relates to a method for treating a subject suffering from a neurodegenerative disease comprising the step of administering at least one TDP-43 interacting compound or a pharmaceutically acceptable salt thereof to the subject.

The present invention also relates to a method for treating a subject suffering from a neurodegenerative disease comprising the step of administering a pharmaceutical composition comprising at least one TDP-43 interacting compound or a pharmaceutically acceptable salt thereof and a pharmaceutical acceptable salt thereof to the subject.

The present invention also relates to a method for treating a subject suffering from a neurodegenerative disease comprising the step of administering at least one withanolide compound or pharmaceutically acceptable salt thereof to the subject.

The present invention also relates to a method for treating a subject suffering from a neurodegenerative disease comprising the step of administering a pharmaceutical composition comprising at least one withanolide compound or a pharmaceutically acceptable salt thereof and a pharmaceutical acceptable carrier to the subject.

The present invention also relates to a non-human transgenic animal model of neurodegenerative disease, wherein the genome of the non-human transgenic model comprises a human TDP-43 genomic fragment operably linked to a human TDP-43 promoter and wherein the non-human transgenic model expresses human TDP-43 polypeptide in a moderate level.

The present invention also relates to an expression cassette comprising the sequence of TDP-43$^{WT}$, TDP-43$^{A315T}$ or TDP-43$^{G348C}$.

The present invention also relates to a transgenic cell transformed with the expression cassette as defined herein.

The present invention also relates to a method for identifying or confirming the utility of a candidate compound useful for preventing and/or treating a neurodegenerative disease, the method comprising the steps of:
  a) administering the candidate compound to the non-human transgenic model as defined herein;
  b) measuring the effect of the candidate compound on the non-human transgenic model in behavioral task test or by in vivo bioluminescence imaging; and
  c) determining if the candidate compound is useful for preventing and/or treating the neurodegenerative disease based on the result of step c).

Figure 5:
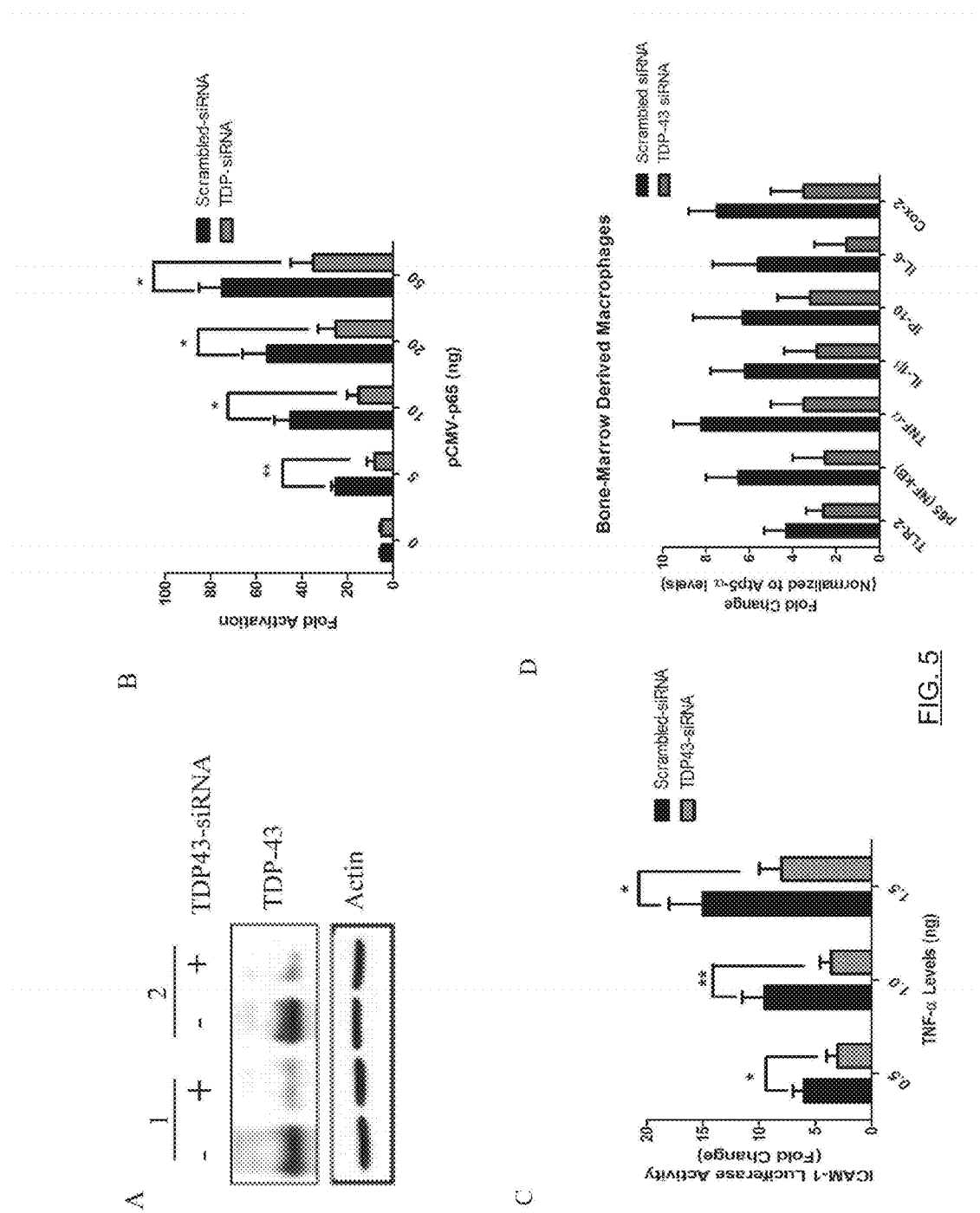
FIG. 5. TDP-43 siRNA inhibits activation of NF-κB. BV-2 cells were transfected either with mouse TDP-43 siRNA or scrambled siRNA. 72 hrs after transfection some of the cells were either stimulated with LPS (100 ng/ml) or mock stimulated for 12 hrs. (A) Protein extracted from siRNA experiment was subjected to western blot analysis. TDP-43 siRNA actually reduced the endogenous mouse TDP-43 levels significantly as compared to scrambled siRNA transfected cells in two different experiments as determined by rabbit polyclonal TDP-43 antibody (1 and 2). (B) Additionally BV-2 cells were transfected with pCMV-p65 (various concentrations) and 4κB$^{wt}$-luc vector. Luciferase assay in TDP-43 siRNA transfected cells revealed decreased activation of NF-κB reporter gene. The decrease in NF-κB activation was about 3-fold for 5 ng pCMV-p65 (**, p<0.01) about 2.5-fold for 10 and 20 ng pCMV-p65 (n=4, *p<0.05) and 2-fold for 50 ng pCMV-p65 (n=4, *p<0.05) as compared to scrambled siRNA transfected cells (C) We transfected BV-2 cells with ICAM1-luc vector in addition to TDP-43 siRNA or scrambled siRNA. 72 hrs after transfection, cells were stimulated with varying concentrations of TNF-α. When stimulated at 0.5 ng/ml of TNF-α, there was a 2-fold decrease in ICAM-1 luciferase activity (*, p<0.05) in TDP-43 siRNA transfected cells as compared to scrambled siRNA cells. Similarly there was a decrease of 2.5-fold (**, p<0.01) and 2-fold (*, p<0.05) in TDP-43 siRNA transfected cells at 1.0 ng/ml and 1.5 ng/ml TNF-α concentrations respectively. (D) TDP-43 siRNA transfected and LPS stimulated BMMs had reduced levels of TLR2 mRNA (1.5-fold, p<0.05), p65 (RELA, 3-fold, p<0.01), TNF-α (3-fold, p<0.01), IL-1β (2-fold, p<0.05), IP-10 (2-fold, p<0.05), IL-6 (2.5-fold, p<0.01) and Cox-2 (2-fold, p<0.05) as compared to scrambled siRNA transfected BMMs. Error bars represent mean±SEM.

*p<0.05) increase in TNF-α levels. TDP-43 harboring the A315T and G348C mutations had similar effects on boosting the levels of TNF-α upon LPS stimulation. (B) The mRNA levels of IL-1β had a similar 5-fold increase (*, p<0.05) in TDP-43 transfected LPS challenged cells. (C) The levels of IL-6 had a significant 9-fold increase (**, p<0.001) in TDP-43 transfected cells compared to untransfected. (D) The levels of Nox-2 gene was 2.8-fold (*, p<0.05) in LPS challenged TDP-43 transfected cells as compared to LPS treated mock-transfected cells. (E) The mRNA levels of p65 (RELA) was significantly (10-fold, , p<0.001) higher in TDP-43 (wild type and mutants) transfected cells than LPS treated mock-transfected cells. Results are displayed as fold change over unstimulated control; error bars represent mean±SEM, n=5. (F) Primary microglial cultures from TDP-43$^{wt}$ and C57Bl/6 mice were stimulated by 100 ng/ml of LPS. Proteins from LPS stimulated microglial cultures were subjected to multi-analyte ELISA for inflammatory cytokines and p65. LPS-treated TDP-43$^{wt}$ transgenic microglia had significantly higher levels of TNF-α (2.5-fold, p<0.01), IL-1β (2.3-fold, **p<0.01), IL-6 (2-fold, *p<0.05), IFN-γ (2-fold, *p<0.05) and p65 (3-fold, **p<0.01) as compared to LPS-treated microglia from C57Bl/6 non-transgenic mice in primary microglial cultures from TDP-43$^{wt}$ transgenic as compared to non-transgenic mice following LPS stimulation. (G) Bone marrow derived macrophages isolated from TDP-43$^{wt}$ and C57Bl/6 mice were stimulated by 50 ng/ml of LPS for 4 hrs. The total RNA samples were then subjected to real-time quantitative RT-PCR. As compared to controls, the LPS-treated macrophages overexpressing TDP-43$^{wt}$ exhibited a 2-fold (p<0.05) increase in TLR2 mRNA and MyD88 mRNA levels, and a 2.8-fold (p<0.01) increase in levels of NF-κB p65 (FIG. 5G). In LPS-stimulated TDP-43$^{wt}$ macrophages there was an increase in a plethora of inflammatory cytokines including TNF-α (3-fold, p<0.01), IL-1β(3-fold, p<0.01), IL-12p40 (3-fold, p<0.01), IL-6 (3.8-fold, p<0.01), Cox-2 (2.7-fold, p<0.02), iNOS (2.7-fold, p<0.01), IP-10 (3-fold, p<0.01), RANTES (2-fold, p<0.05) compared to LPS stimulated control (non-transgenic) macrophages. Results are displayed as fold change over unstimulated control; error bars represent mean±SEM, n=4.

Figure 8:
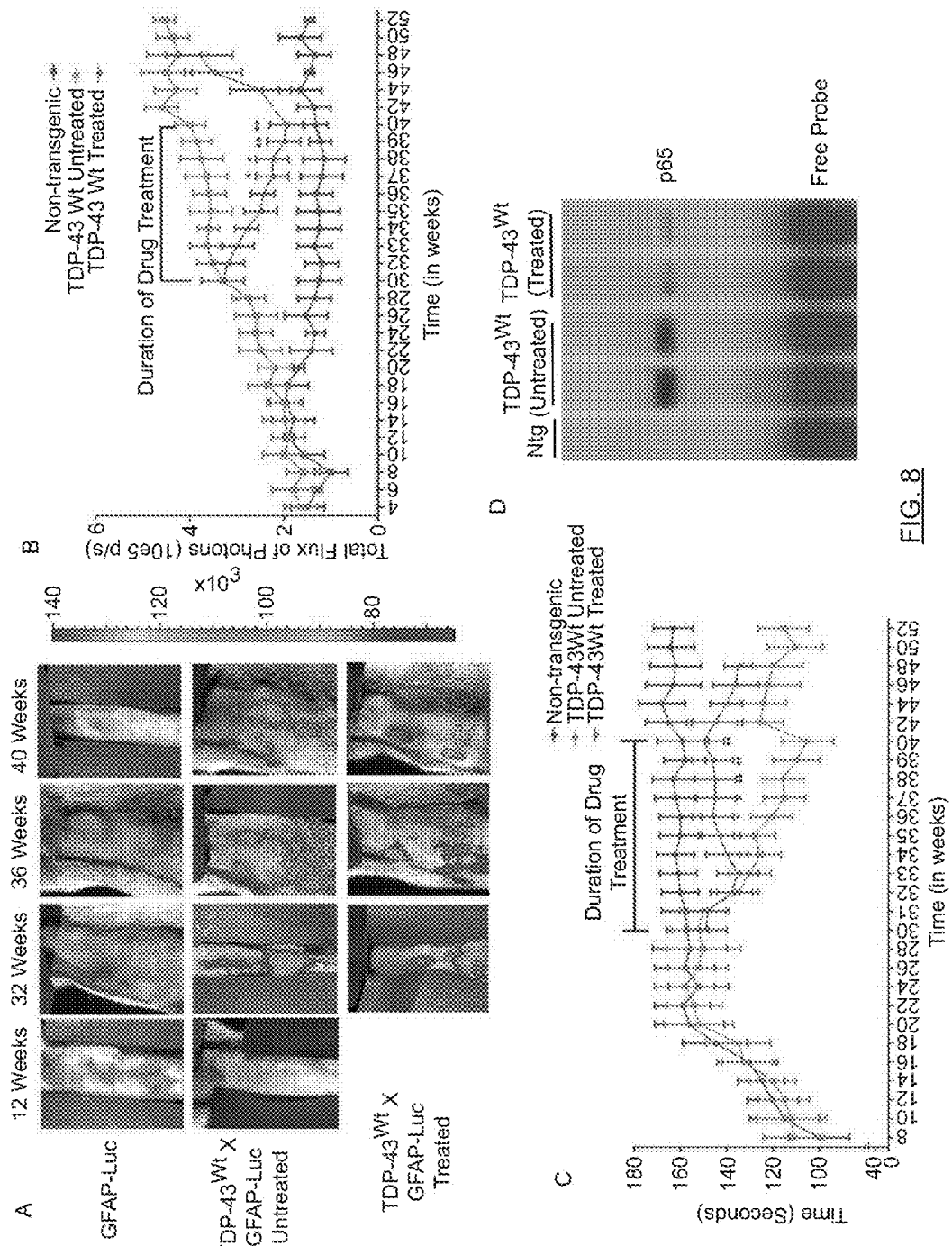
Figure 8:
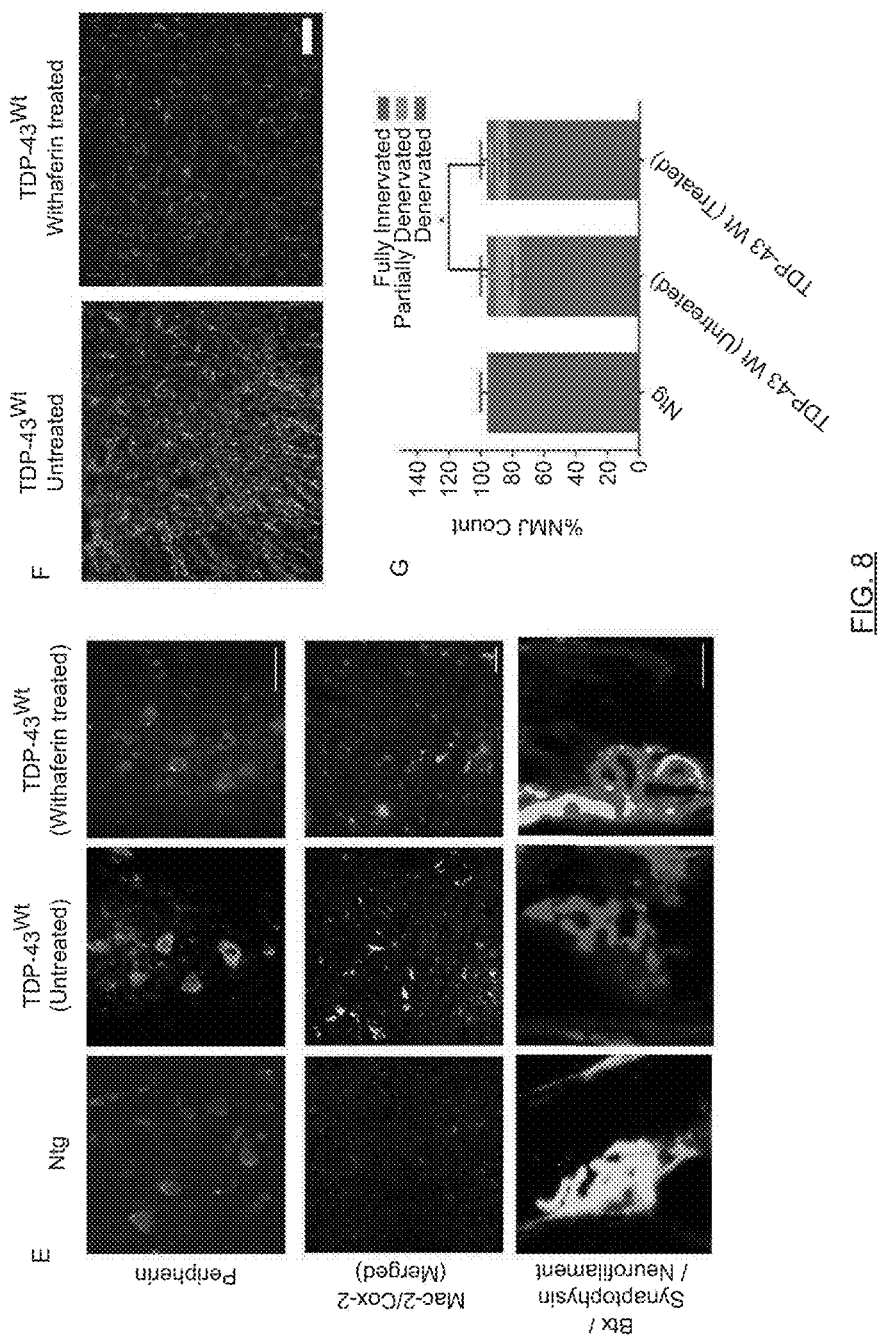

FIG. 8. Withaferin A, an inhibitor of NF-κB, reduces neuronal vulnerability to toxic injury and ameliorates disease phenotypes in TDP-43 transgenic mice (A) In vivo bioluminescence imaging of astrocyte activation was analyzed at various time points in the spinal cord of GFAP-luc/TDP-43$^{Wt}$ mice. Typical sequence of images of the spinal cord area obtained from of GFAP-luc/TDP-43$^{Wt}$ mice at different time points (12, 32, 36, and 40 weeks) by in vivo imaging. Withaferin A was injected in GFAP-luc/TDP-43$^{Wt}$ for 10 weeks starting at 30-weeks of age till 40-weeks. Significant reduction in GFAP promoter activity can be observed in withaferin treated GFAP-luc/TDP-43$^{Wt}$ mice at 36 and 40 weeks age compared to untreated GFAP-luc/TDP-43$^{Wt}$ mice. Control GFAP-luc mice had low background bioluminescence (n=10, each group). (B) Longitudinal quantitative analysis of the total photon GFAP-signal/bioluminescence (total flux of photon/s) in withaferin A treated and untreated GFAP-luc/TDP-43$^{Wt}$ mice and control GFAP-luc mice in the spinal cord are displayed. GFAP imaging analysis of withaferin treated TDP-43 transgenic mice after cessation of the drug treatment shows increase in GFAP luciferase activity. * represents a statistically significant difference between treated and untreated groups (p<0.05) and ** (p<0.01) using repeated-measures 2-way ANOVA (n=10, each group). (C) Accelerating rotarod analysis was performed in GFAP-luc/TDP-43$^{Wt}$ mice at various ages from 8-weeks to 52-weeks. Withaferin A treatment period is marked as drug treatment period. Rotarod experiments demonstrate that withaferin treated GFAP-luc/TDP-43$^{Wt}$ mice had much better rotarod performance than untreated GFAP-luc/TDP-43$^{Wt}$ mice. Rotarod analysis of withaferin treated TDP-43 transgenic mice after cessation of the drug treatment shows decrease in rotarod performance. * represents a statistically significant difference between treated and untreated groups (p<0.05) and ** (p<0.01) using repeated-measures 2-way ANOVA (n=10, each group). (D) p65 EMSA was performed on the spinal cord tissue nuclear lysates from withaferin treated and untreated GFAP-luc/TDP-43$^{Wt}$ mice. p65 EMSA revealed that withaferin treated mice had much reduced nuclear active p65 as compared to untreated GFAP-luc/TDP-43$^{Wt}$ mice (n=5 each group). (E) Immunofluorescence of spinal cord sections of non-transgenic (control), TDP-43$^{Wt}$ (untreated) and TDP-43$^{Wt}$ (Withaferin treated) mice with polyclonal peripherin antibody. Withaferin treated mice show reduced levels of peripherin in spinal cord. Double immunofluorescence of spinal cord sections with activated microglial marker Mac-2 and cyclooxygenase-2 (Cox-2) was performed and quantified (FIG. 14F). Neuromuscular junction (NMJ) staining was performed using anti-synaptophysin/neurofilament antibodies (green) and α-bungarotoxin (BTX-red). Representative images showing fully innervated muscle in 10-months old non-transgenic mice, fully denervated muscle in TDP-43$^{Wt}$ mice (untreated) and partially denervated muscle in age-matched withaferin treated TDP-43$^{Wt}$ mice. (F) Immunofluorescence using GFAP antibody was performed in the spinal cord sections of withaferin treated and untreated GFAP-luc/TDP-43$^{Wt}$ mice (n=5, each group) showing that withaferin treated group had significantly low GFAP activation. (G) Three hundred neuromuscular junctions were counted per animal sample. Frequencies of innervation, partial denervation and denervation were then converted to percentages and plotted as graph. (n=5 per group). There is a significant decrease in the number of partially denervated muscle (9±4%) in withaferin treated TDP-43$^{Wt}$ mice as compared to age-matched untreated TDP-43$^{Wt}$ mice (15±5%). *p<0.01. Scale bar=20 μm. Error bars represent mean±SEM.

Figure 9:
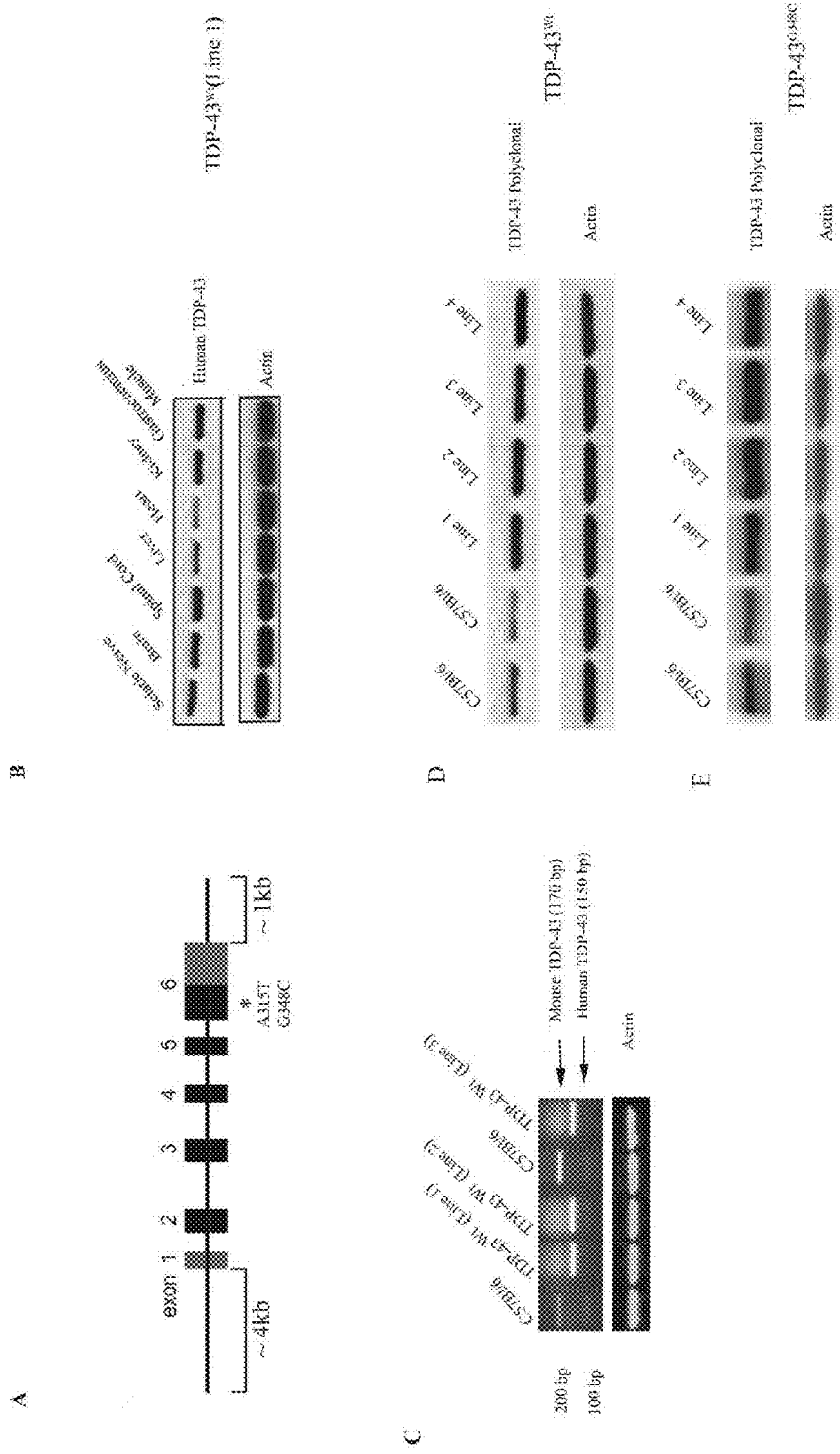

FIG. 9. Generation of TDP-43$^{wt}$ transgenic mice. (A) Schematic diagram showing the structure of the human TARDBP transgene cloned from a BAC clone using PCR. The A315T and G348C mutations (site shown by *) were introduced into the TARDBP transgene construct using site-directed mutagenesis. Note that the construct uses TARDBP's own promoter (~4 kb). The whole ~18 kb fragment was sequenced confirmed before being microinjected in mice. (B) Expression of human TDP-43 in various tissues including brain, spinal cord, sciatic nerve, liver, kidney, heart and gastrocnemius muscle as detected by human monoclonal antibody (Abnova, 1:1000). (C) RT-PCR analyses of total RNA from 2-month old mice brain showing human TDP-43$^{wt}$ mRNA levels compared to mouse endogenous. Actin is shown as a loading control. (D) TDP-43 levels in the spinal cord of all the TDP-43$^{wt}$ transgenic mice produced are shown using polyclonal TDP-43 that detect both human and endogenous mouse TDP-43 levels. Mouse line 1 is used for all further experiments. (E) TDP-43 levels in the spinal cord of all the TDP-43$^{G348C}$ transgenic mice using polyclonal TDP-43 that detect both human and endogenous mouse TDP-43 levels. Mouse line 4 is used for all further experiments. Actin is shown as loading control.

Figure 10:
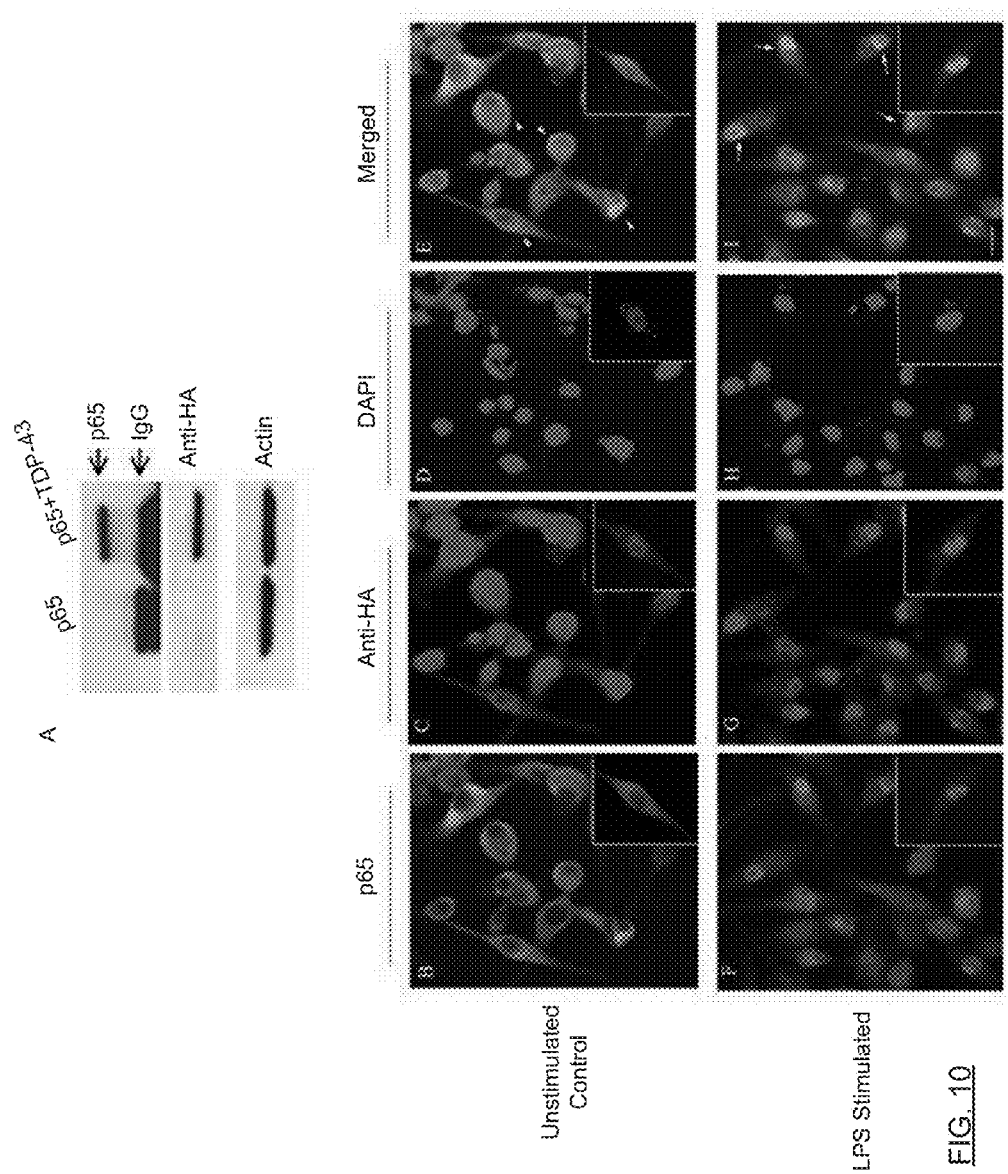

FIG. 10. In vitro interaction of TDP-43 with p65. (A) pCMV-TDP43$^{wt}$ (HA-tagged) and pCMV-p65 were co-transfected in BV-2 cells. 48 hrs after transfection, cells were harvested and total protein extracted. Cell extract was incubated with dynabeads magnetic beads coupled with anti-HA antibody. After incubation and further washing, the complexes were resolved by 10% SDS-PAGE and subjected to chemiluminescence detection. p65 was co-immunoprecipitated with anti-p65 mouse monoclonal antibody showing that TDP-43 interacts with p65 in vitro. The positions of TDP-43 and mouse IgG heavy chain are indicated. (B-E) A double immunofluorescence experiment was set up by transfecting BV-2 cells with pCMV-TDP43$^{wt}$ and pCMV-p65. 24 hrs after transfection, cells were either LPS (100 ng/ml) or mock-stimulated. 12 hrs after stimulation, cells were fixed in 4% PFA and stained with Anti-HA antibody (for TDP-43) and mouse monoclonal p65 antibody and counterstained with nuclear marker-DAPI. Mock stimulated TDP-43$^{wt}$ transfected cells show no nuclear co-localization (arrow heads) of p65 (some co-localization in cytoplasm) and TDP-43$^{wt}$. (F-I) LPS stimulated TDP-43$^{wt}$ cells had significant co-localization (white arrow) of p65 and TDP-43$^{wt}$. Magnification 40×. Inset showing cells at a higher 63× magnification. Scale bar=20 µm.

Figure 11:
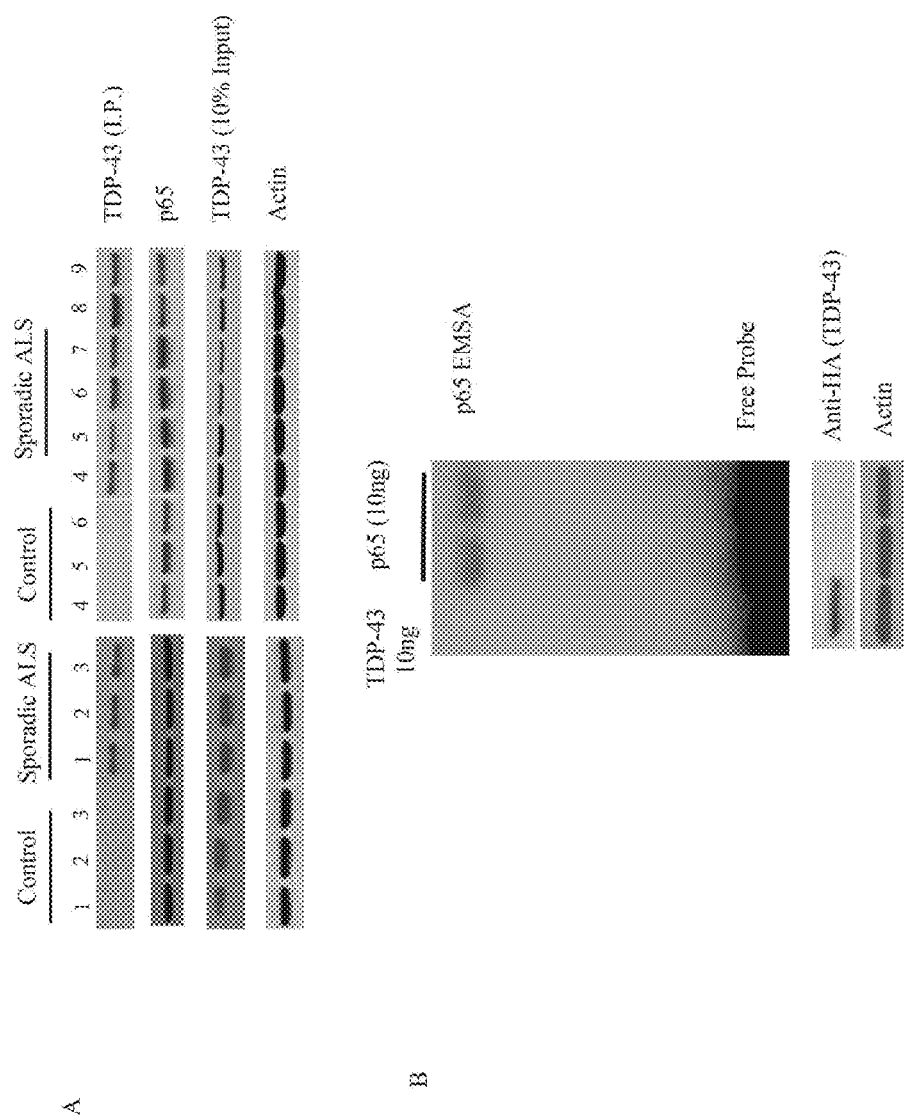

FIG. 11. TDP-43 co-immunoprecipitates with antibodies against p65. (A) TDP-43 was co-immunoprecipitated by antibody against p65 using spinal cord samples from in 9 sporadic ALS cases, but not from 6 control cases. Western blot for TDP-43 is shown as input, p65 as immunoprecipitation control and actin as loading control. (B) BV-2 cells were transfected with either 10 ng TDP-43 or with 10 ng p65. Nuclear extracts were subjected to p65 EMSA. TDP-43 does not bind to p65 EMSA probe on its own, p65 effectively binds. TDP-43 expression levels are shown using anti-HA antibody and actin is shown as a loading control for the western blot.

Figure 12:
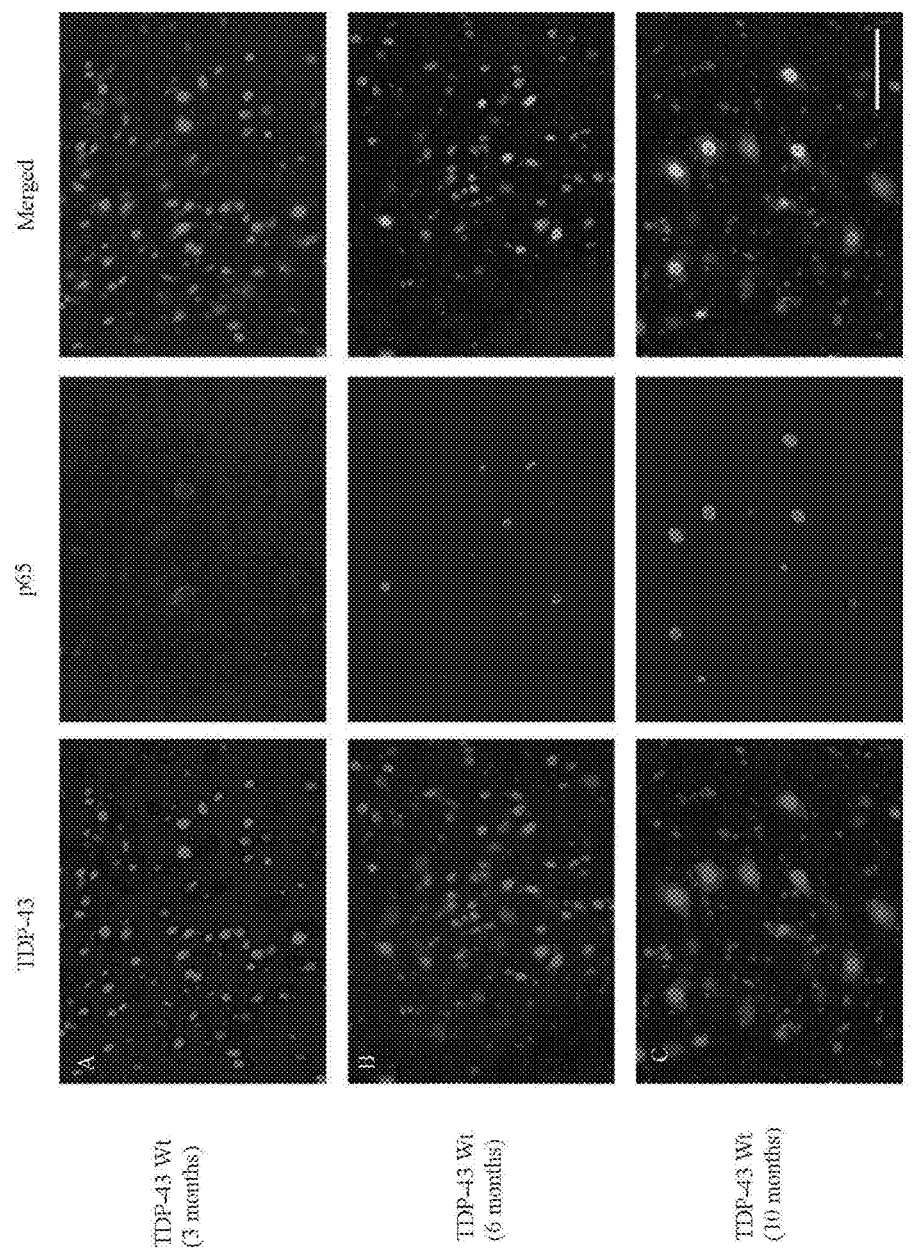

FIG. 12. Age-dependent increase in p65 activation in TDP-43$^{Wt}$ transgenic mice. A-C Double immunofluorescence with TDP-43 (polyclonal) and p65 antibody in the spinal cord of TDP-43Wt transgenic mice at various ages—3 months (A), 6-months (B) and 10-months (C). In 3-months spinal cord, p65 is not activated and is mainly in the cytoplasm. With the progression of age, p65 is activated gradually in 6-months and more in 10-months. Scale bar=20 µm.

Figure 3:
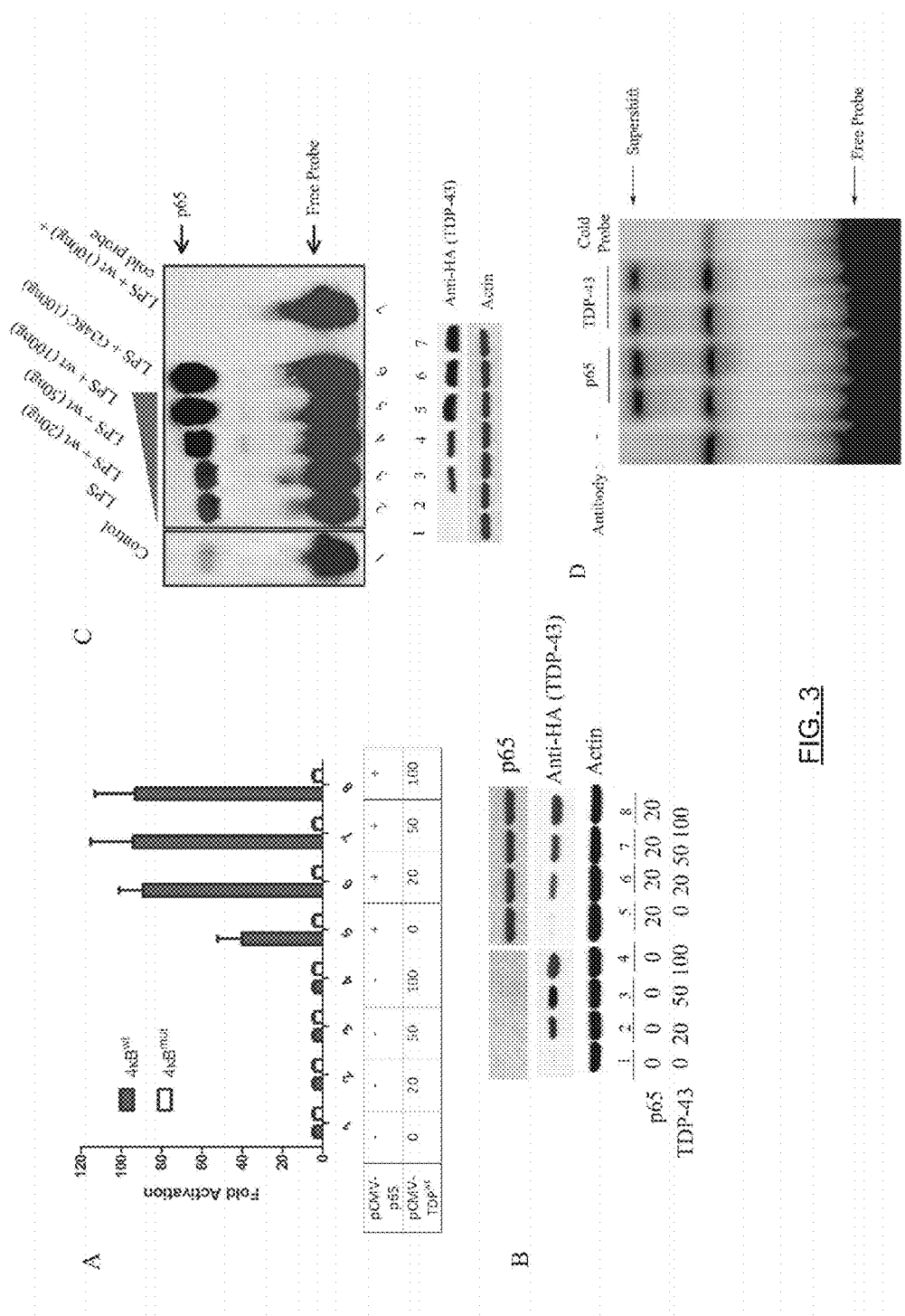
FIG. 3. TDP-43 acts as a co-activator of NF-κB p65. (A) BV-2 cells were transfected with 20 ng of 4κB$^{wt}$-luc (containing wild type NF-κB binding sites) or 4κB$^{mut}$-luc (containing mutated NF-κB binding sites) together with the indicated amounts of pCMV-TDP43$^{wt}$ expression plasmid. Cells were harvested 48 h after transfection, and luciferase activity was measured. Values represent the luciferase activity mean±SEM of three independent transfections. TDP-43 transfected BV-2 cells were treated with 100 ng/ml of LPS. (B) BV-2 cells were transfected with 20 ng pCMV-p65 and various concentrations of pCMV-TDP43$^{wt}$. Western blot analysis of the transfected cell lysate revealed no increase in the protein level of exogenously expressed p65. TDP-43 levels are shown when blotted with Anti-HA antibody (Sigma), Actin is shown as a loading control. (C) 48 hrs after transfection, BV-2 cells were harvested and nuclear extracts prepared. These nuclear extracts were then incubated with NF-κB p65 binding site specific oligonucleotides coated with streptavidin. EMSA was then performed using the NF-κB EMSA kit. LPS alone activated p65 levels to about 2-fold as compared to control (lane 2). Co-transfection of TDP-43$^{wt}$ (50 ng and 100 ng) resulted in a significant dose-dependent activation of p65 (lane 4 and 5). TDP- 43$^{G348C}$ (100 ng) co-transfection had similar effects of TDP-43wt transfection on the activation of p65 (lane 6). The specificity of the assay was ascertained by adding cold probe (lane 7). TDP-43 levels are shown when blotted with Anti-HA antibody (Sigma). Actin is shown as a loading control. (D) Supershift assay was performed by adding anti-HA antibody, which specifically recognizes human TDP-43, during the EMSA assay. p65 antibody was also added in a separate lane as a positive control. Note that all the samples were TDP-43 and p65 transfected and LPS stimulated. Error bars represent mean±SEM.
Figure 13:
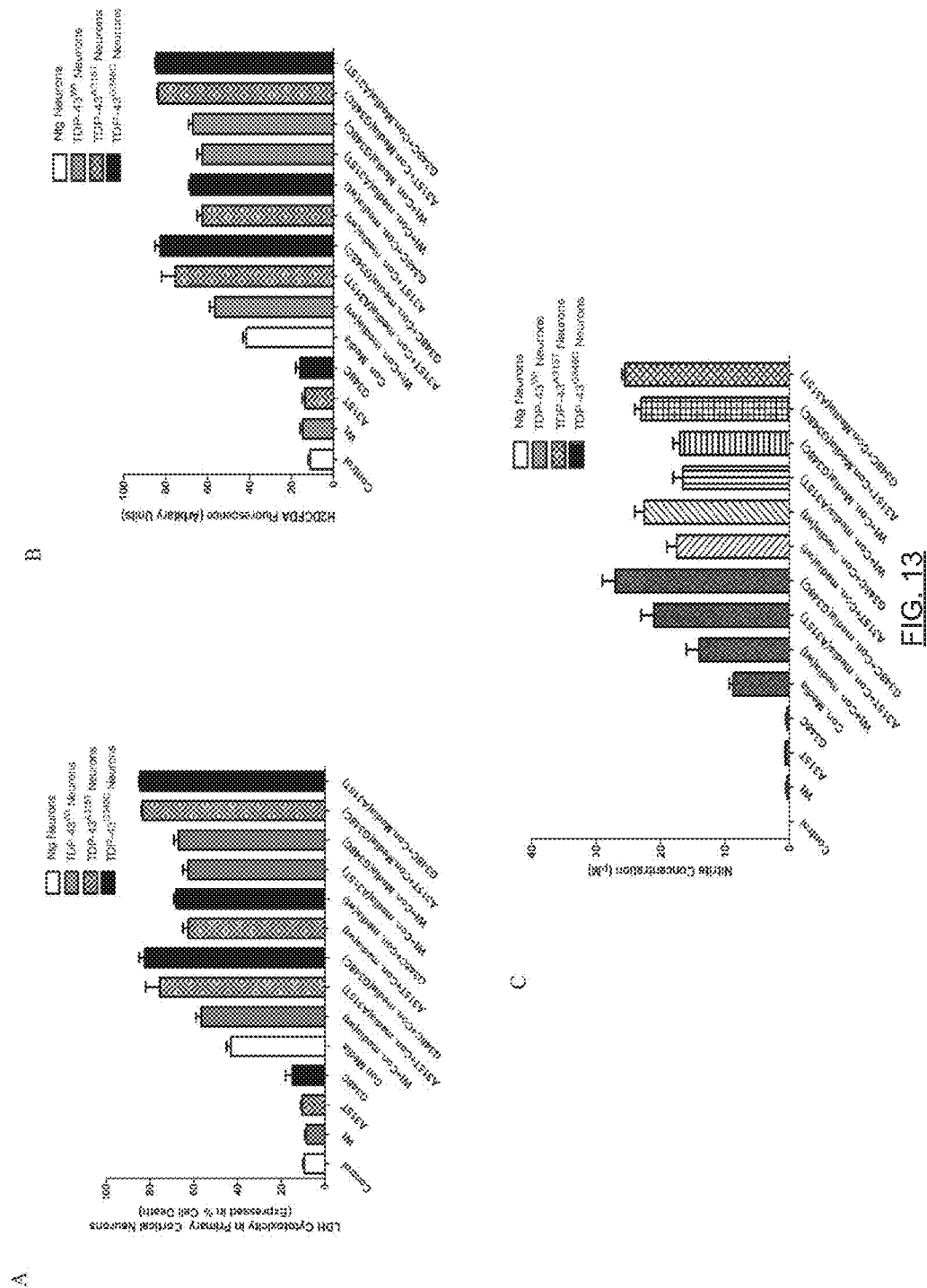

FIG. 13. TDP-43 upregulation enhances neuronal vulnerability to death by microglia-mediated cytotoxicity. Primary cortical neurons from TDP43$^{wt}$, TDP43$^{A315T}$ and TDP43$^{G348C}$ mouse were incubated with the conditioned media derived from primary microglial cells treated with 50 µg/ml LPS. 12 hrs after challenging cortical cells, cell-culture supernatants were used for downstream assays. (A) There is an increase in the cytotoxicity of cortical neurons from C57Bl/6 non-transgenic mice (about 3.5-fold, p<0.01) which were incubated in conditioned media from LPS-challenged microglia of the same genotype as compared to those neurons which were not kept in conditioned media. There is also marked increase in the cytotoxicity of TDP-43$^{wt}$ (5.5-fold, p<0.001), TDP-43$^{A315T}$ (6.5-fold, p<0.001) and TDP-43$^{G348C}$ (7.5-fold, p<0.001) cortical neurons which were incubated in conditioned media (of same genotype) from microglia as compared individually to those neurons which were not kept in conditioned media. TDP-43$^{A315T}$ (1.5-fold, p<0.05) and TDP-43$^{G348C}$ (1.7-fold, p<0.05) neurons incubated in conditioned media from TDP-43$^{wt}$ microglia had less cell death compared to TDP-43$^{A315T}$ and TDP-43$^{G348C}$ neurons which were incubated in conditioned media from microglia of corresponding genotypes. (B) ROS production, as determined by H2DCFDA fluorescence, was significantly higher in TDP-43$^{wt}$ (1.5-fold, p<0.05), TDP-43$^{A315T}$ (1.8-fold, p<0.05) or TDP-43$^{G348C}$ (2-fold, p<0.05) as compared individually to non-transgenic control. (C) Nitrite production was significantly higher in TDP-43$^{wt}$ (1.5-fold, p<0.05), TDP-43$^{A315T}$ (2.3-fold, p<0.05) or TDP-43$^{G348C}$ (3-fold, p<0.01) as compared individually to non-transgenic control (FIG. 3C).

Figure 14:
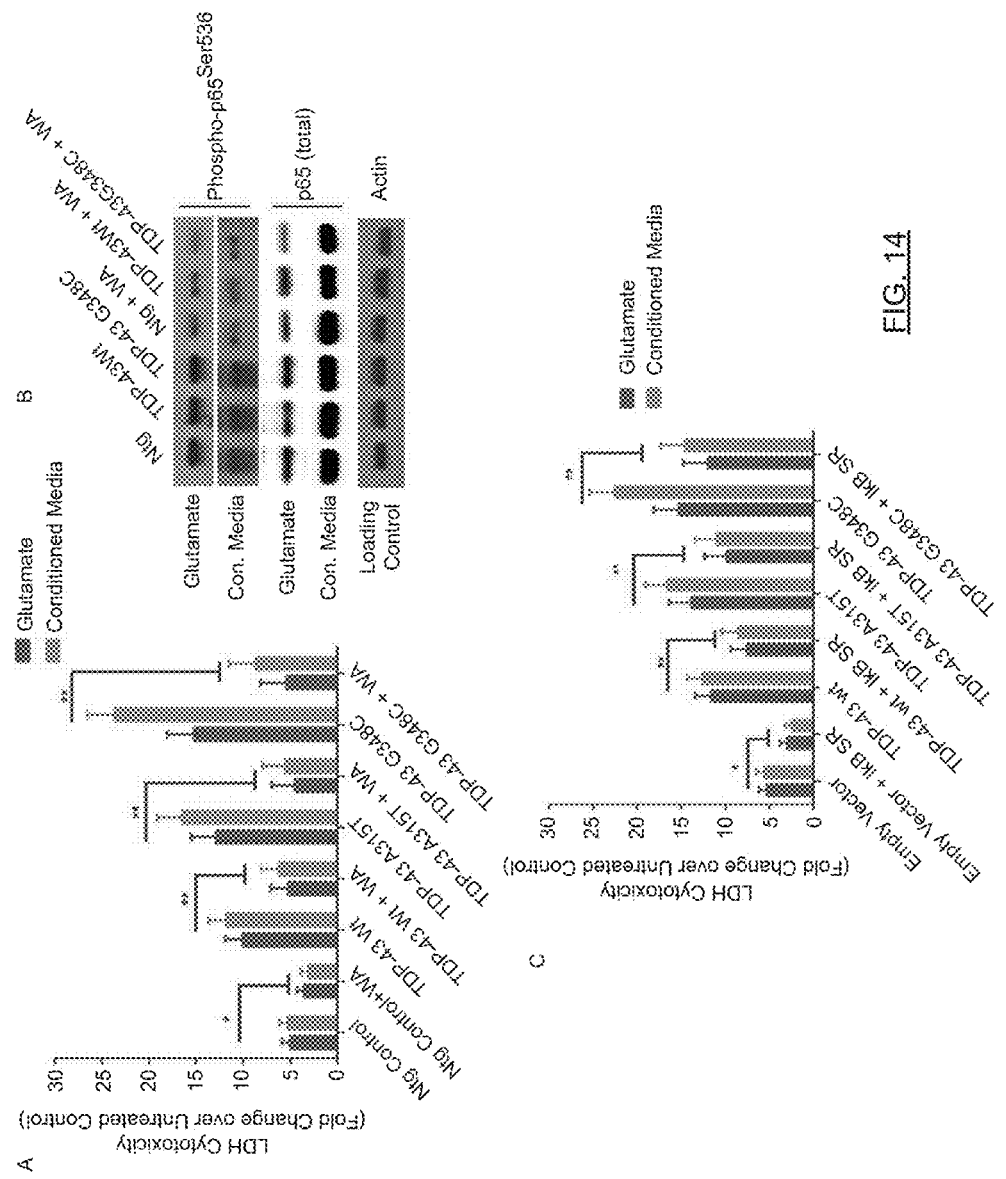
Figure 14:
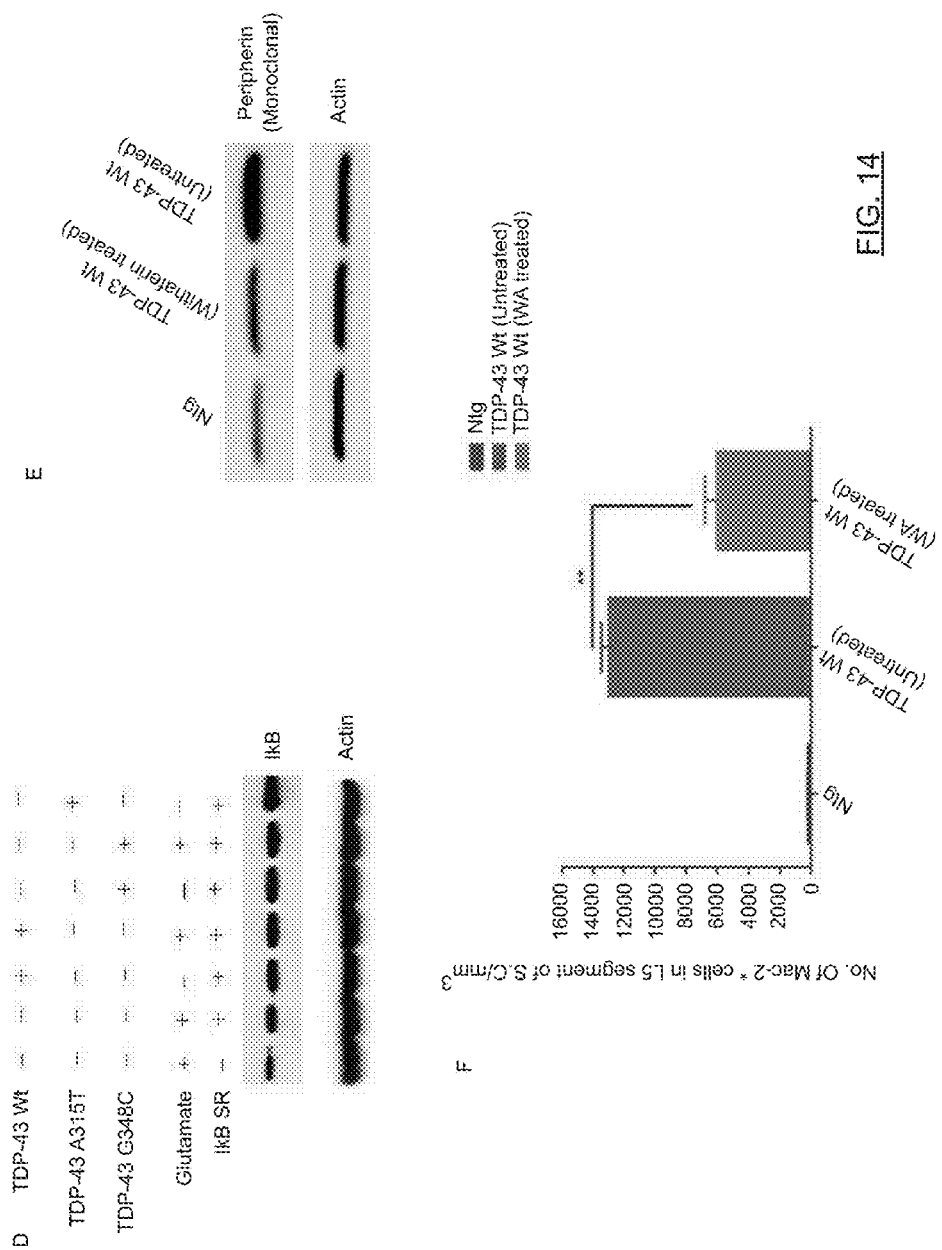

FIG. 14. Withaferin A ameliorates disease phenotypes in TDP-43 transgenic mice (A) (A) Primary cortical neurons were exposed to 10 µM glutamate for 15 min with or without 1 µM withaferin A (WA) and were evaluated for LDH cytotoxicity 24 hrs later. There was a marked increase in glutamate cytotoxicity in TDP-43 (wt, A315T and G348C mutants) transgenic neurons as compared to C57Bl/6 non-transgenic (Ntg) control. Addition of WA resulted in marked decrease in cell death in TDP-43$^{wt}$ (2-fold, p<0.01), TDP-43$^{A315T}$ (3-fold, p<0.01), TDP-43$^{G348C}$ (3-fold, ** p<0.01) and Ntg (1.4-fold, *p<0.05) neurons compared to untreated neurons exposed to glutamate. Cortical neurons were also incubated with the conditioned media from primary microglial culture, which were challenged with LPS at a concentration of 50 ng/ml of media. Neuronal losses were detected in TDP-43$^{wt}$, TDP-43$^{A315}$, TDP-43$^{G348C}$ and Ntg neurons incubated in conditioned media from microglia of respective genotypes. However, treatment with WA resulted in significant decrease in neuronal death of TDP-43$^{wt}$ (2-fold, p<0.01), TDP-43$^{A315T}$ (3-fold,  p<0.01) and TDP-43$^{G348C}$ (3-fold, p<0.01) as compared to untreated neurons exposed to glutamate. (B) Treatment with WA resulted in inhibition of NF-κB as evident by reduced levels phospho-p65$^{Ser536}$ both in glutamate and conditioned media challenged neuronal cells. Total p65 for each condition is shown using p65 specific antibody and Actin is shown as loading control. (C) A stable mutant super-repressive form of IκB-α (IκB$^{SR}$) was expressed and its effects on neuronal death were evaluated. The phosphorylation-defective IκBαS32A/S36A acts by sequestering the cytoplasmic NF-κB pool in a manner that is insensitive to extracellular stimuli. Cultured cortical neurons (Ntg, TDP-43$^{wt}$, TDP-43$^{A315T}$ and TDP-43$^{G348C}$) were transfected with a plasmid construct, expressing IκBSR, and exposed to either 10 µM glutamate for 30 min or incubated in conditioned media from LPS-stimulated microglia of same genotype. IκB$^{SR}$ inhibits NF-κB activation causing reduced cell death of TDP-43$^{wt}$ (1.3-fold, p<0.01), TDP-43$^{A315T}$ (1.5-fold, p<0.01) and TDP-43$^{G348C}$ (2-fold,  p<0.01) as compared to untreated neurons exposed to glutamate. Similar results were obtained when neurons were incubated in conditioned media from LPS-stimulated microglial culture of corresponding genotypes. Data represent mean±SEM from three independent experiments, n=3 (D) IκB levels were measured by western blot analysis of the cell lysates from cortical neurons of various genotypes. Actin is shown as loading control. Various conditions are also shown. (E) Western blot analysis of spinal cord sections of non-transgenic (control), TDP-43$^{Wt}$ (untreated) and TDP-43$^{Wt}$ (Withaferin treated) mice with monoclonal peripherin antibody. Withaferin treated mice show reduced levels of peripherin in spinal cord. (F) Quantification of microglial Mac-2 positive cells in the spinal cord sections of non-transgenic (control), TDP-43$^{Wt}$ (untreated) and TDP-43$^{Wt}$ (Withaferin treated) mice showing reduced numbers of Mac-2 positive cells in withaferin treated mice. Mac-2$^+$ cells in TDP-43$^{Wt}$ (untreated) L5 spinal cord 13000±500/mm$^3$ and TDP-43$^{Wt}$ (Withaferin treated) L5 spinal cord 6000±300/mm$^3$ **p<0.001.

Figure 15:
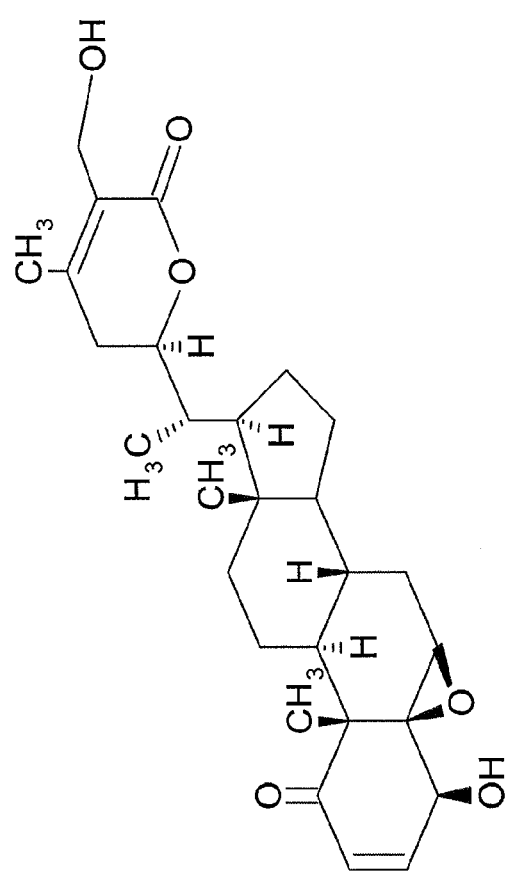
Figure 15:
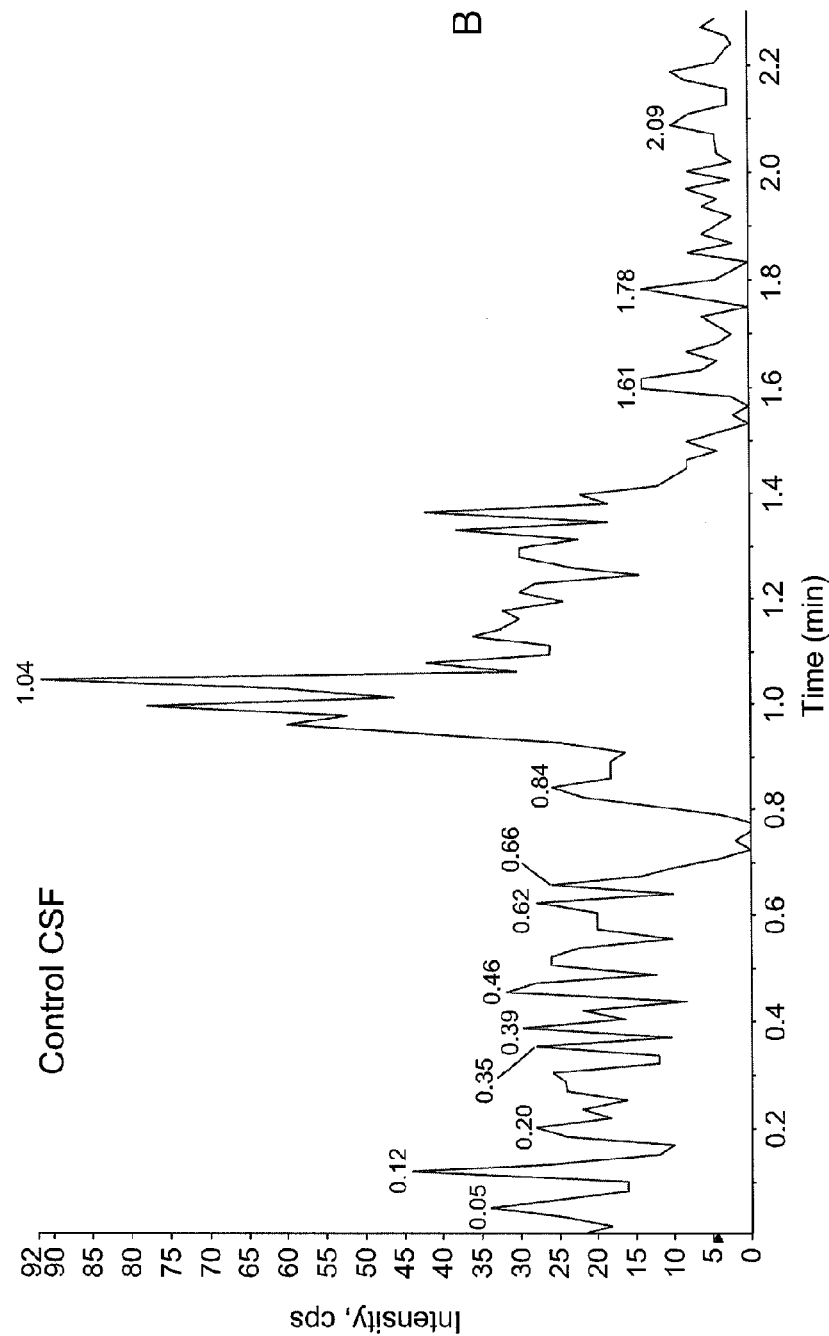
Figure 15:
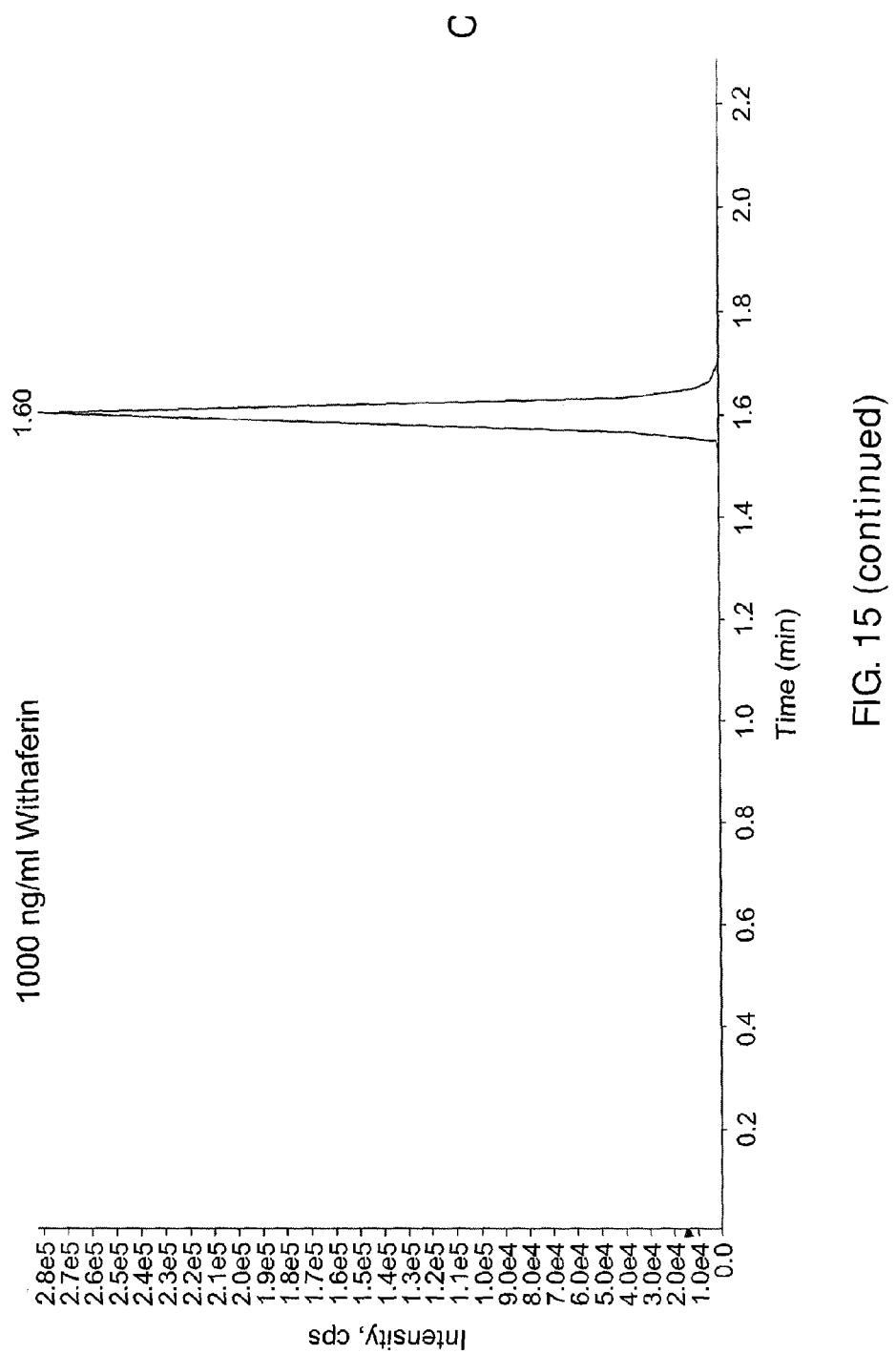
Figure 15:
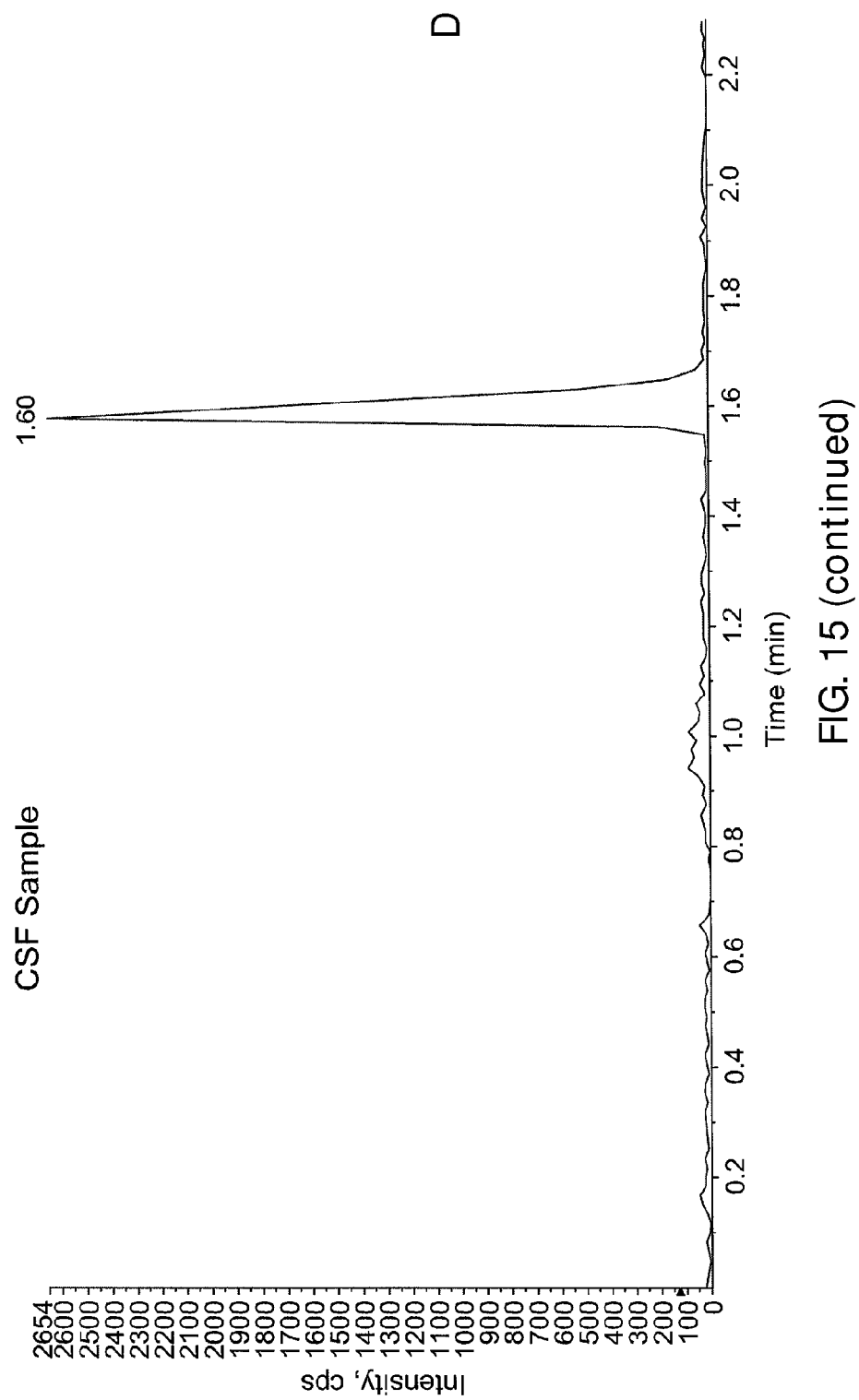

FIG. 15. Detection of Withaferin A in the CSF of mice using HPLC. (A) Chemical structure of withaferin A. (B-D) Withaferin A was injected (3 mg/kg body weight) intraperitoneally in 8-months old control non-transgenic and TDP-43$^{Wt}$ mice. For blank samples (B), 0.9% saline was injected in non-transgenic mice. 1.5 hrs after injection, CSF samples from the mice were obtained using stereotaxic injection into the cistern magna. 50 µl of the sample was mixed with 60% ACN 0.1% formic acid, centrifuged and the supernatant was injected into HPLC. Blank CSF sample showing absence of Withaferin-A and drug injected CSF samples showing presence of Withaferin-A (D). 1000 ng/ml withaferin-a chemical served as a standard (C). Withaferin retention time was 1.6 mins.

Figure 16:
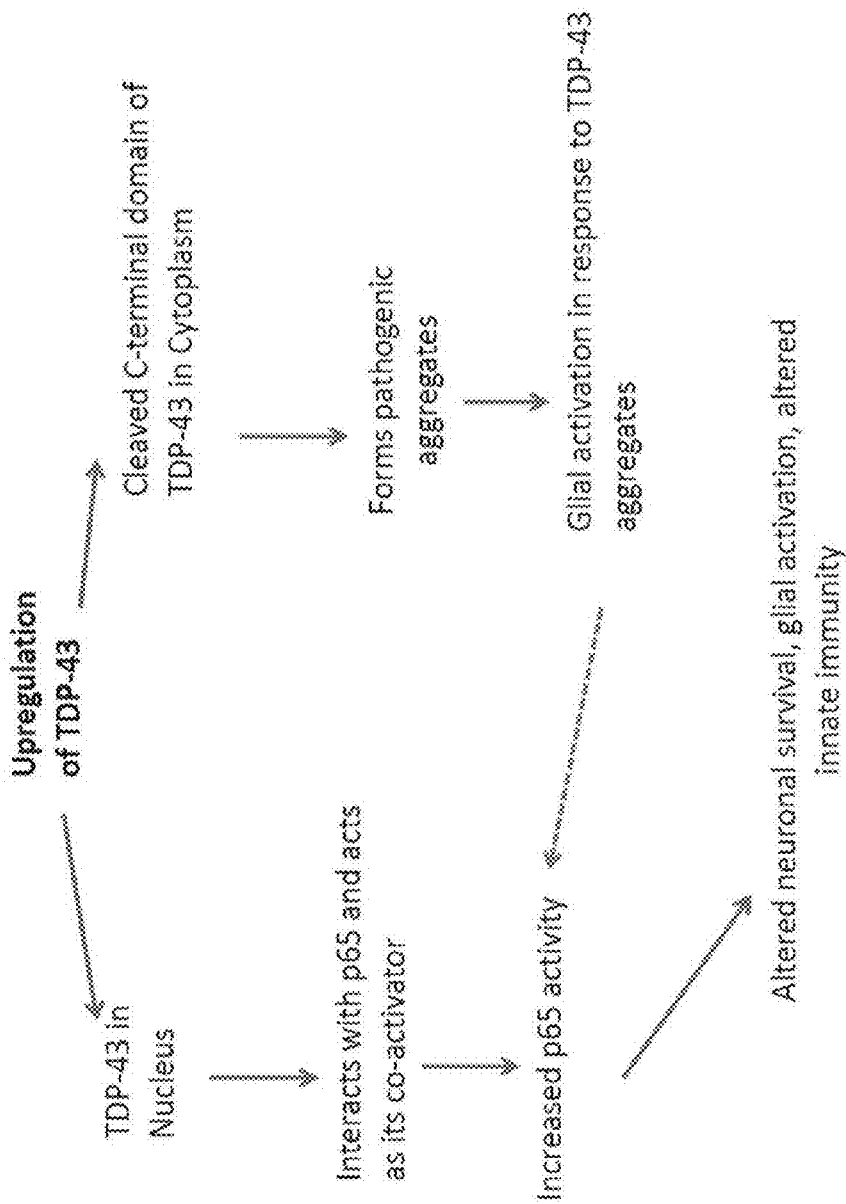

FIG. 16. Pathogenic Mechanism of TDP-43 mediated NF-kB toxicity. Model showing TDP-43 mediated toxicity of NF-kB. Nuclear upregulation of TDP-43 causes aberrant p65 NF-kB activation resulting in neurotoxicity, increased glial response and altered innate immune response. Concomitantly, in ALS, TDP-43 forms cytoplasmic aggregates prompting glial response to TDP-43 aggregates. Glial responses follow a cascading chain event by activating p65 NF-kB.

Figure 17:
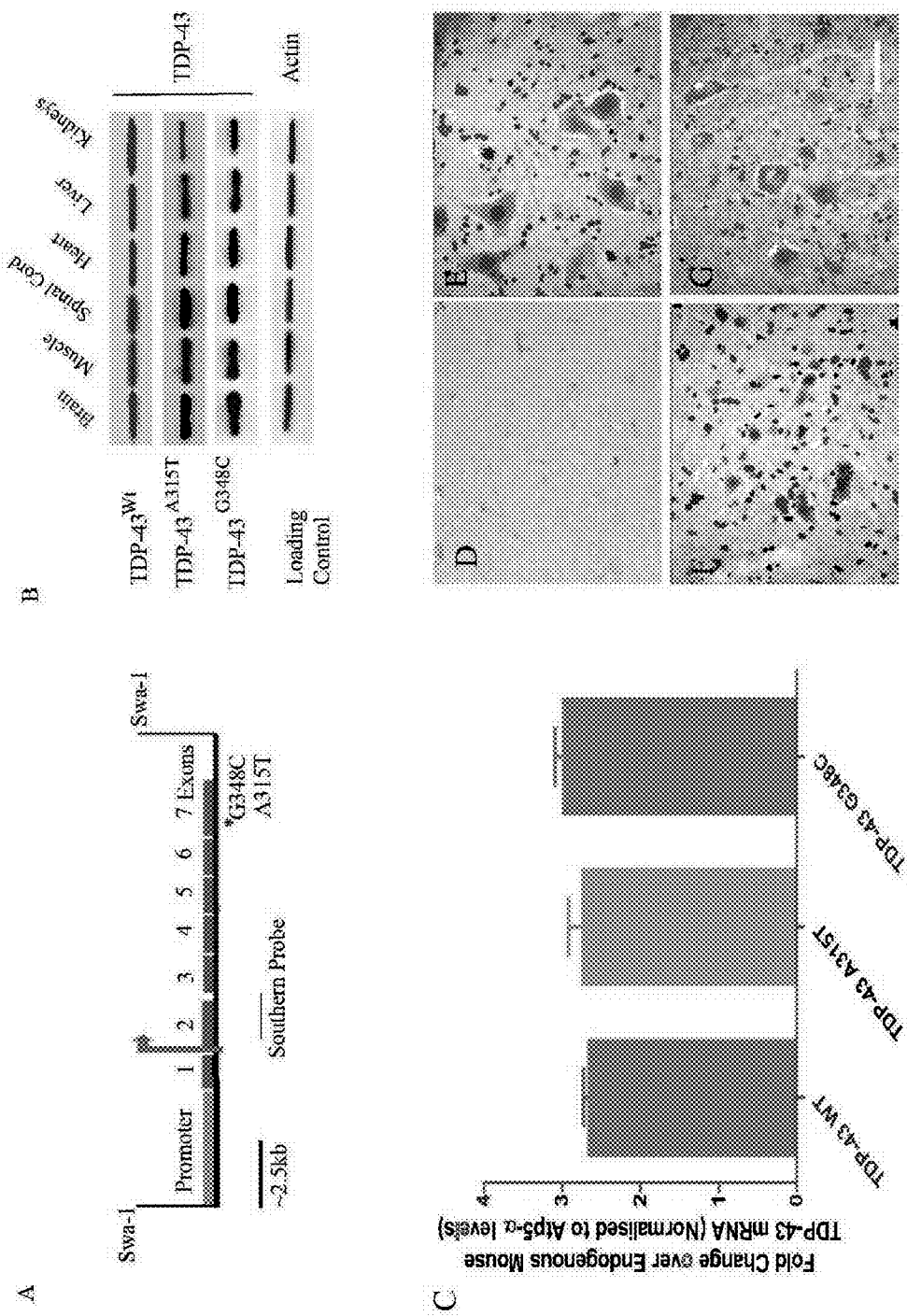

FIG. 17. Generation and characterisation of TDP-43 transgenic mice. (A) Map of human TARDBP gene (Gene ID: 23435) showing upstream ~4 kb promoter (un-characterized) and various exons (numbered 1-7) and introns. The orientation of transcription is shown by arrow. * showing position of 2 mutations—G348C (1176 G>T) and A315T (1077 G>A). The approximate locations of the Southern blotting probes are also indicated. (B) Western blots from lysates of various tissues from TDP-43$^{Wt}$, TDP-43$^{A315T}$ and TDP-43$^{G348C}$ transgenic mice at 2-months age using mouse monoclonal TDP-43 antibody that detect hTDP-43 only. Actin is shown as loading control. (C) Quantitative real-time PCR analysis of hTDP-43 mRNA expression in the spinal cord of TDP-43$^{Wt}$, TDP-43$^{A315T}$ and TDP-43$^{G348C}$ transgenic mice at 2-months age compared individually to their wild-type littermates and normalized to Atp-5α levels. Data shown are means±SEM of 5 different mice from each group. (D-G) Immunohistochemistry shows hTDP-43 expression pattern in the spinal cord of ~8-months old TDP-43$^{Wt}$, TDP-43$^{A315T}$ and TDP-43$^{G348C}$ transgenic mice using TDP-43 monoclonal antibody. It is noteworthy that the expression of TDP-43 is mostly nuclear in TDP-43$^{Wt}$ mice (E), but TDP-43 is localized in the cytoplasm in TDP-43$^{G348C}$ mice (G), and to a lesser extent in TDP-43$^{A315T}$ mice (F). TDP-43 monoclonal antibody does not recognize endogenous mouse TDP-43 in non-transgenic control mice (D). Scale bar=20 µm.

Figure 18:
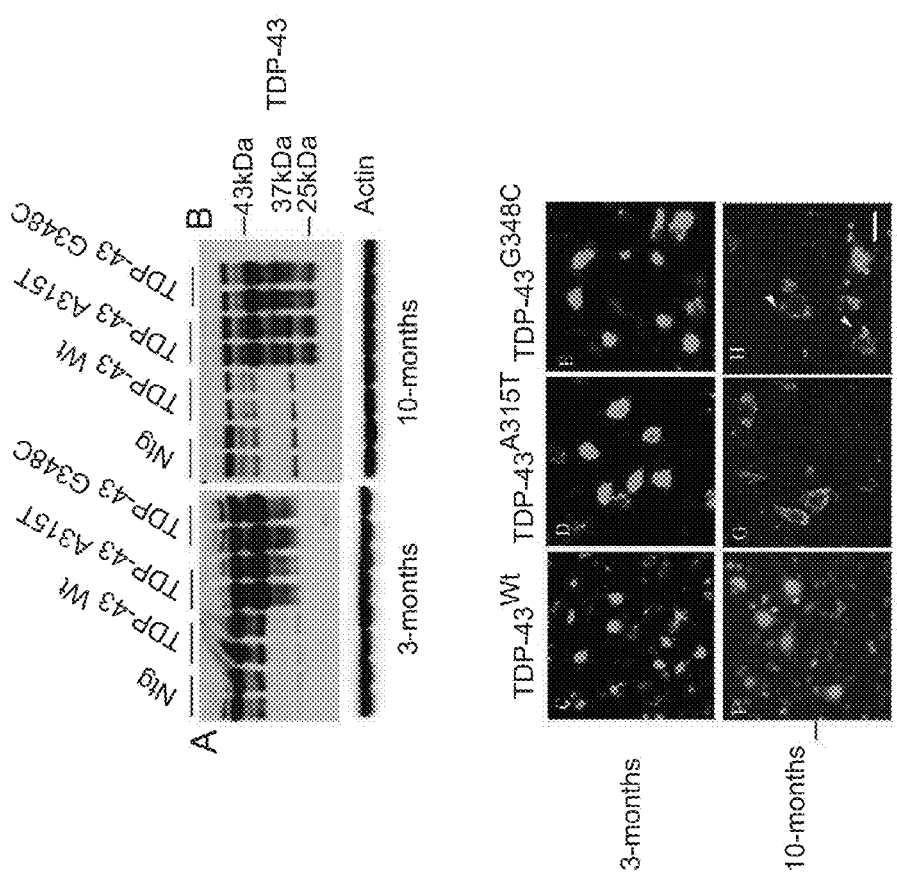
Figure 18:
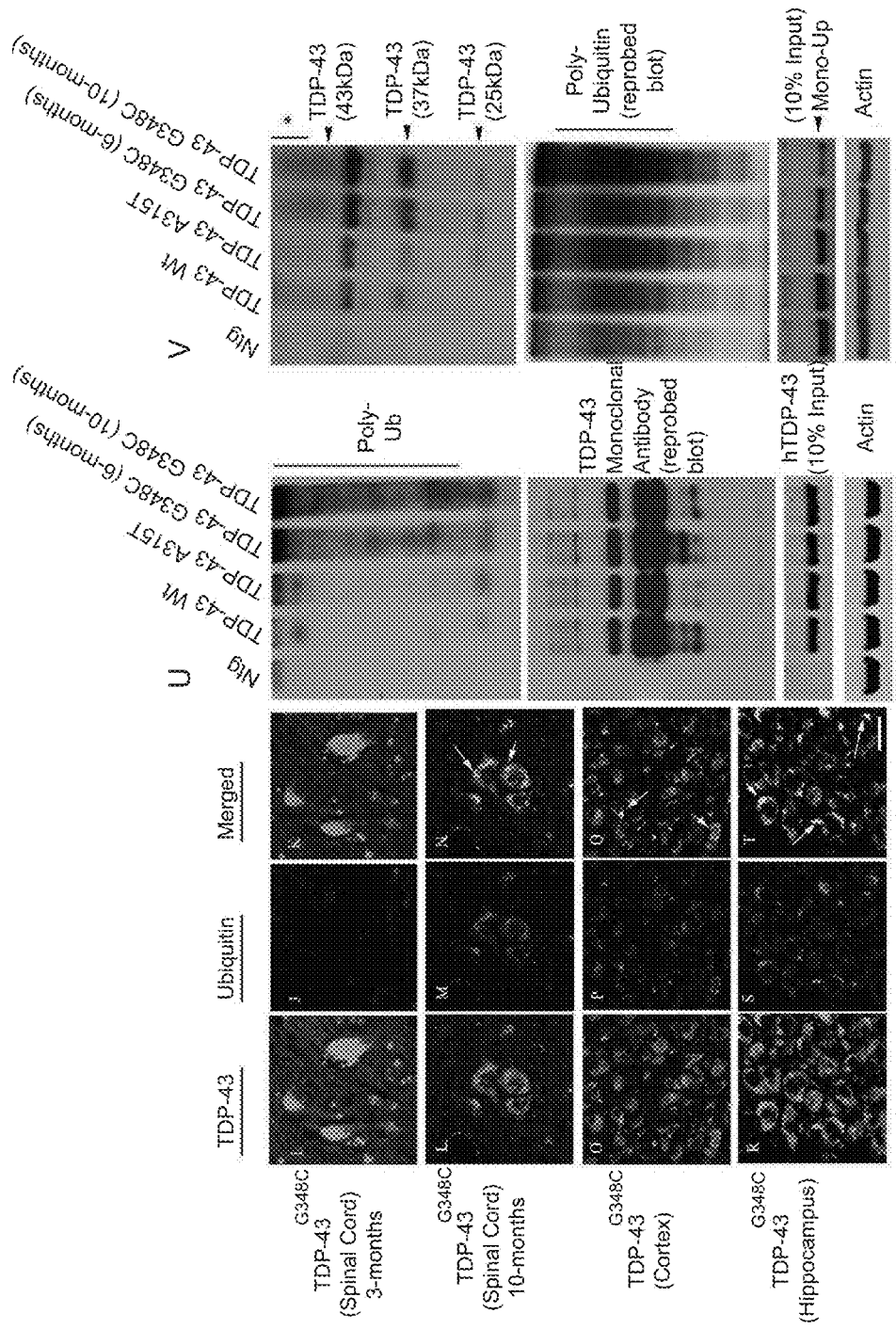

FIG. 18. Biochemical and pathological features of ALS/FTLD in TDP-43 transgenic mice. (A-B) Western blot of spinal cord lysates from Ntg (non-transgenic), TDP-43$^{Wt}$, TDP-43$^{A315T}$ and TDP-43$^{G348C}$ mice using polyclonal TDP-43 antibody at 3 and 10-months show that TDP-43 (both G348C and A315T mutants) have ~35 and ~25 kDa fragments which increase with age. Actin is shown as a loading control. (C-H) Immunofluorescence of the spinal cord of 10-month old TDP-43$^{Wt}$ (F), TDP-43$^{A315T}$ (G) and TDP-43$^{G348C}$ mice (H) using TDP-43 monoclonal antibody show cytoplasmic hTDP-43 aggregates (arrow-heads) especially in the spinal cord sections of TDP-43$^{G348C}$ transgenic mice. Some of the TDP-43 is still in nucleus (asterisk). On the other hand, spinal cord sections of 3-month old transgenic mice show nuclear staining exclusively (C-E). (I-T). Double immunofluorescence of the brain and spinal cord sections of 10-months old TDP-43$^{G348C}$ mice using monoclonal TDP-43 antibody and anti-ubiquitin antibody show ubiquitinated TDP-43 aggregates (arrows) in spinal cord (L-N), cortex (O-Q) and hippocampal (R-T) regions. (I-K) Spinal cord sections of 3-months old TDP-43$^{G348C}$ mice do not show intense ubiquitination. Background intensities were matched with 10-month old mice for consistency. (U) Co-immunoprecipitation of ubiquitin using mouse monoclonal TDP-43 from spinal cord lysates of transgenic mice show that proteins associated with hTDP-43 are poly-ubiquitinated (Poly-Ub), more in TDP-43$^{G348C}$ mice. Note that the ubiquitination is more in 10-months old mice than in 6-months old TDP-43$^{G348C}$ mice. Reprobed western blot is shown for TDP-43 using monoclonal antibody. Western blot of hTDP-43 using monoclonal antibody is shown as 10% input and actin as loading control. (V) Reverse co-immunoprecipitation with anti-ubiquitin antibody shows that TDP-43 was co-immunoprecipitated with anti-ubiquitin. However, only small amount of high molecular weight forms of TDP-43 (i.e. poly-ubiquitinated) could be detected. Western blot of ubiquitin using polyclonal antibody is shown as 10% input and actin as loading control. Scale bar: C-H, 50 µm; I-T, 25 µm.

Figure 19:
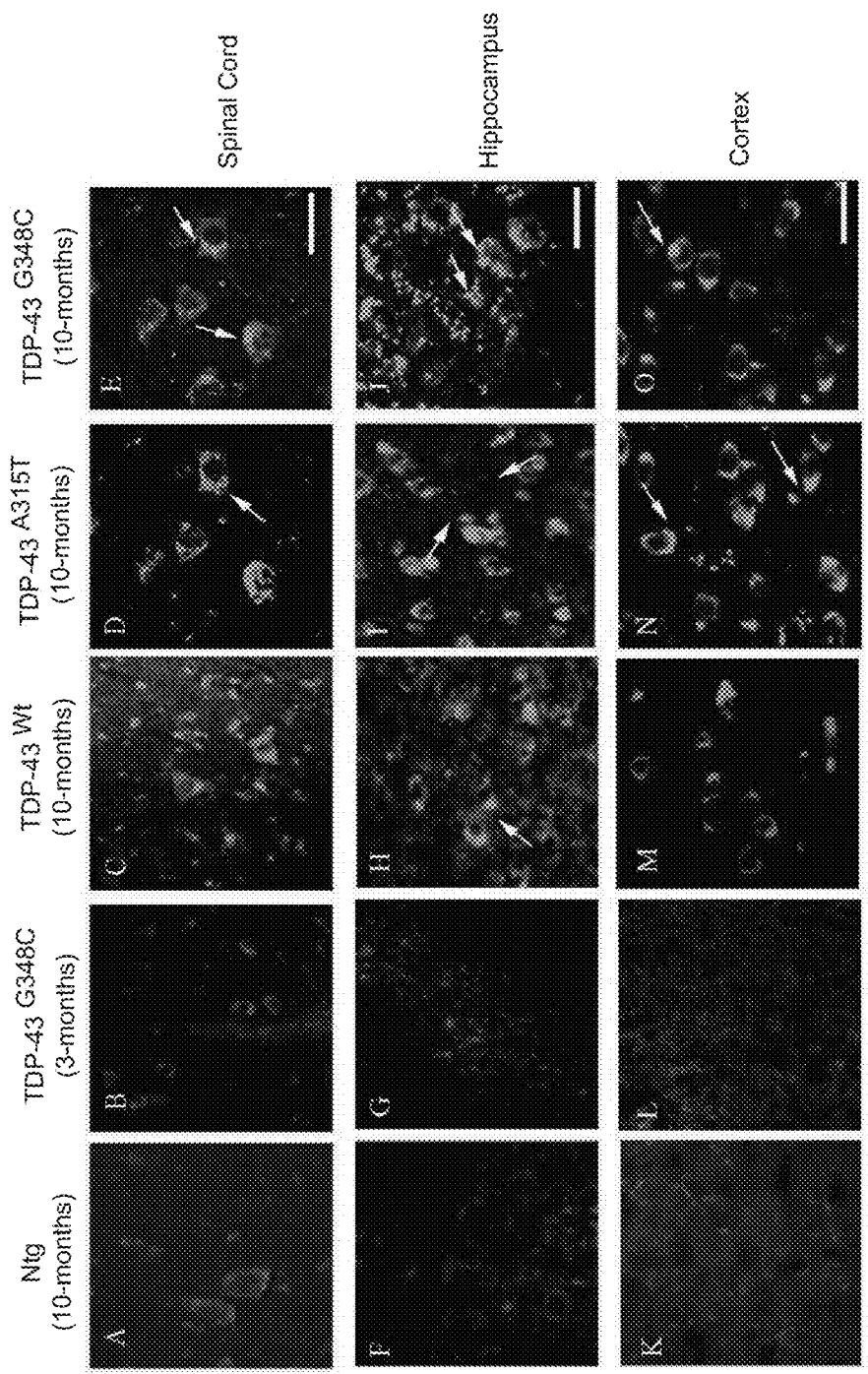
Figure 19:
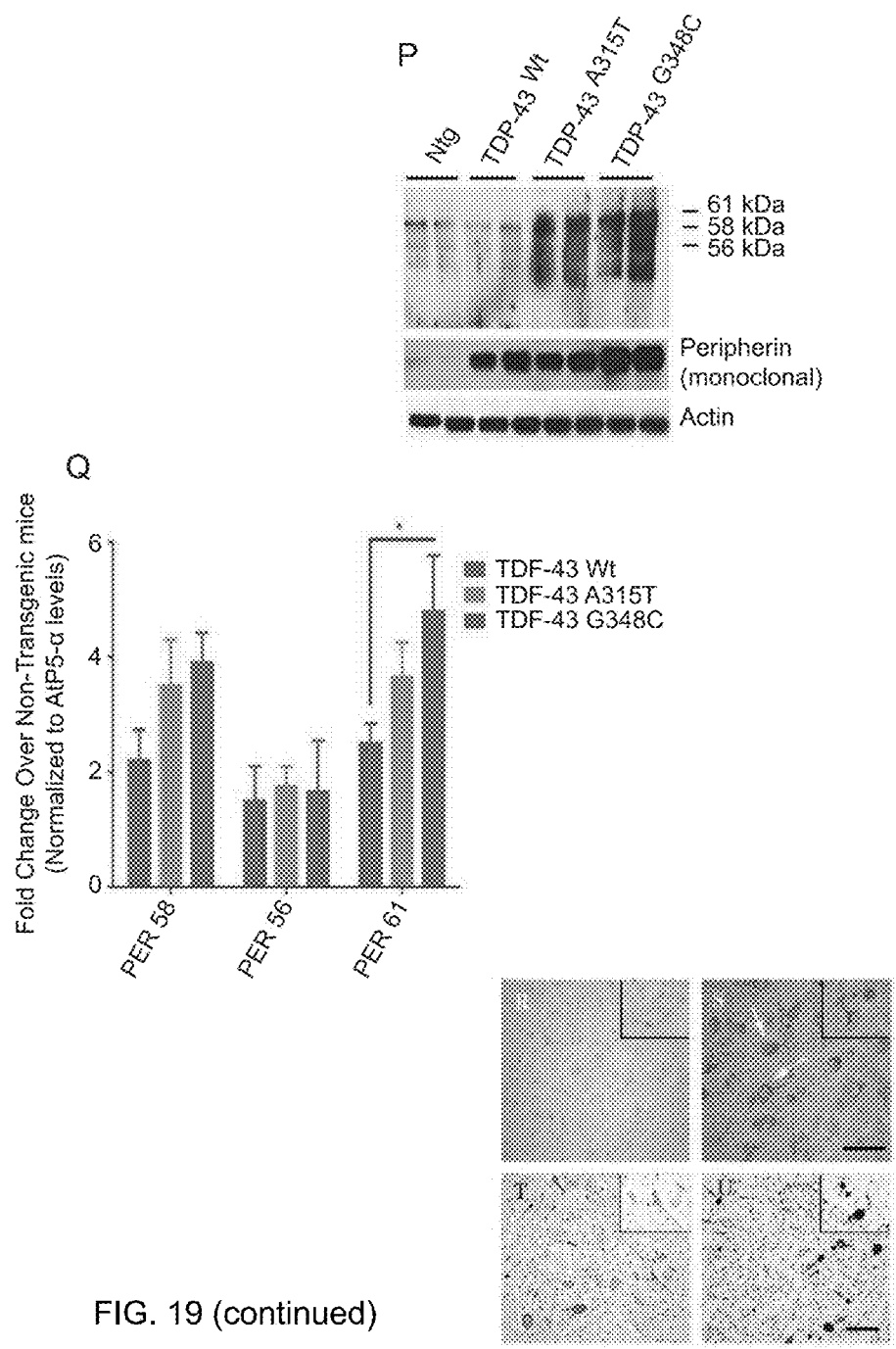
Figure 20:
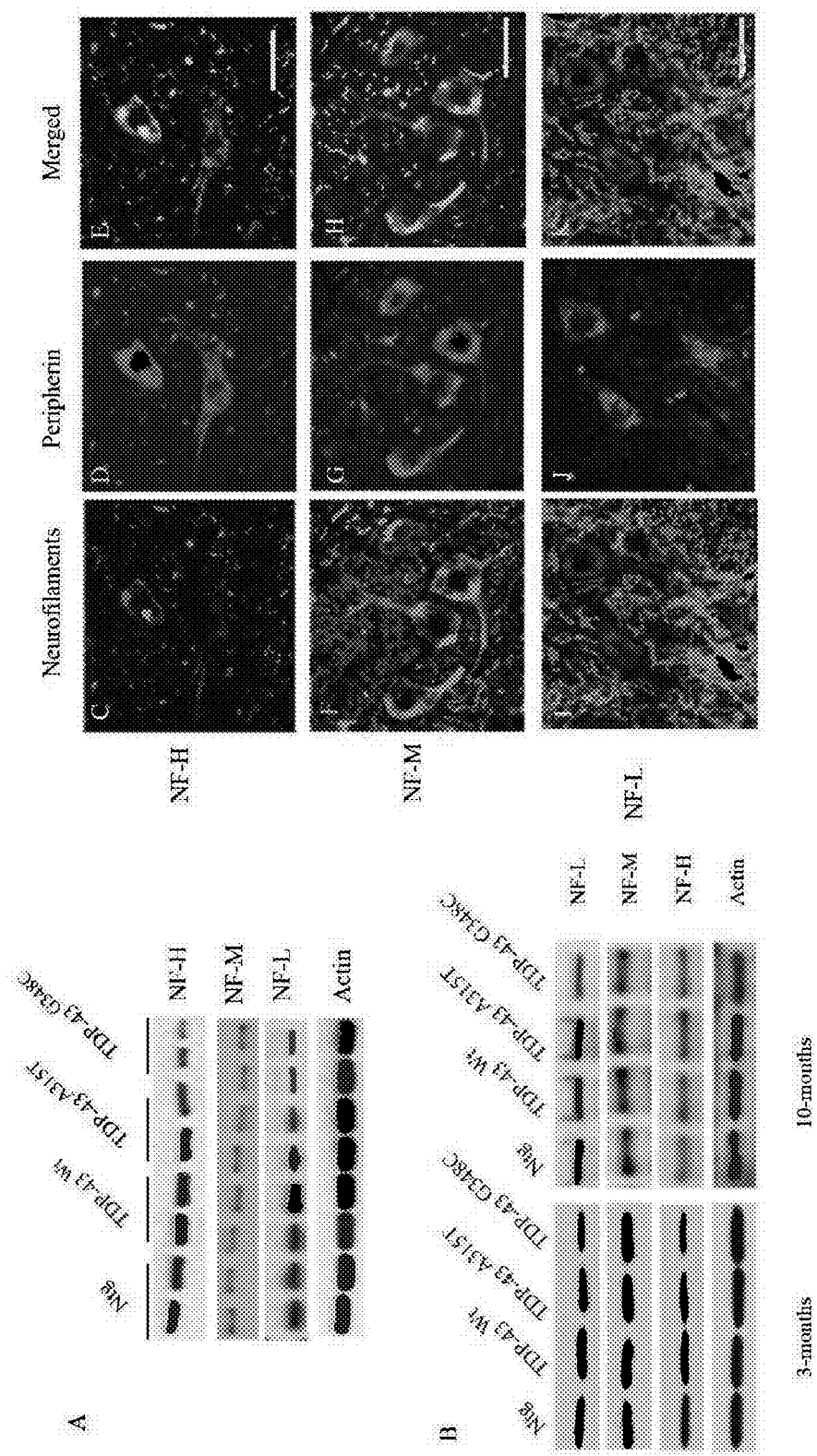

FIG. 19. Peripherin abnormalities in TDP-43 transgenic mice. A-O. Immunofluorescence of the brain (F-O) and spinal cord (A-E) sections of 10-months old Ntg (non-transgenic), TDP-43$^{Wt}$, TDP-43$^{A315T}$ and TDP-43$^{G348C}$ transgenic mice using polyclonal anti-peripherin antibody. Peripherin immunofluorescence of the spinal cord sections show peripherin aggregates more in TDP-43$^{G348C}$ mice (E) (arrow), but also some in TDP-43$^{A315T}$ mice (C) and very less in TDP-43$^{Wt}$ mice (C) as compared to non-transgenic control (A). Spinal cord sections of 3-months old TDP-43$^{G348C}$ mice do not show peripherin overexpression or aggregates (B). (F-J) Hippocampal region of the brain of 10-month old TDP-43$^{G348C}$ mice show abundant peripherin aggregates (J). Peripherin aggregates are also seen to a lesser extent in TDP-43$^{A315T}$ mice (I) and very less in TDP-43$^{Wt}$ mice (H) as compared to non-transgenic control (F) and 3-months old TDP-43G348C mice (G). (K-O) Similarly, peripherin immunofluorescence in 10-months old TDP-43$^{G348C}$ mice (O) in the cortical region of the brain show peripherin aggregates. These aggregates are also seen to a lesser extent in TDP-43$^{A315T}$ mice (N) and very less in TDP-43$^{Wt}$ mice (M) as compared to non-transgenic control (K) and 3-months old TDP-43G348C mice (L). (P) Western blot analysis of the brain lysates of 10-months old Ntg, TDP-43$^{Wt}$, TDP-43$^{A315T}$ and TDP-43$^{G348C}$ transgenic mice using polyclonal peripherin antibody reveal various peripherin splice variants including the Per61, Per58 and Per56 fragments especially in TDP-43$^{G348C}$ mice. Monoclonal peripherin antibody revealed overexpression of peripherin in TDP-43$^{G348C}$, TDP-43$^{A315T}$ and to a lesser extent in TDP-43$^{Wt}$ mice as compared to non-transgenic control. Actin is shown as loading control. (Q) Quantitative real-time PCR analysis of mRNA levels of peripherin splice variants—Per61, Per58 and Per56 in the spinal cord lysates show that TDP-43$^{G348C}$ mice had ~2.5-fold higher Per61 transcript levels than in TDP-43$^{Wt}$ spinal cord. Per58 levels are also higher in TDP-43$^{G348C}$ mice compared to TDP-43$^{Wt}$ mice, but no significant differences are observed in Per56 levels between different transgenic mice. Peripherin transcript levels are expressed as fold change over non-transgenic controls normalized to Atp-5α levels. One-way ANOVA was used with Tukey's post-hoc comparison for statistical analysis (n=3), *p<0.01 (R-U) Immuno-histochemistry on spinal cord tissues using Per61 specific antibody reveal Per61 specific aggregates in TDP-43$^{G348C}$ mice (S) similar to sporadic ALS spinal cord tissues (U). In contrast, Per61 antibody yielded weak staining of the spinal cord in human control (T) and in TDP-43$^{Wt}$ transgenic mice (R). Inset showing higher magnification images. Scale bars: A-O 25 µm; R-U 50 µm FIG. 20. Neurofilament abnormalities in TDP-43 transgenic mice. (A) Western blots of various neurofilament proteins on the spinal cord lysates of 10-months old Ntg (non-transgenic), TDP-43$^{Wt}$, TDP-43$^{A315T}$ and TDP-43$^{G348C}$ transgenic mice using NF-H, NF-M and NF-L specific antibodies. Note the sharp reduction in the protein levels of NF-L and NF-H in TDP-43$^{G348C}$ spinal cord lysates as compared to TDP-43$^{Wt}$ lysates. Actin is shown as loading control. (B) Western blots of various neurofilament proteins on the spinal cord lysates of 3-months and 10-months old Ntg (non-transgenic), TDP-43$^{Wt}$, TDP-43$^{A315T}$ and TDP-43$^{G348C}$ transgenic mice using NF-H, NF-M and NF-L specific antibodies. Actin is shown as loading control. C-K. Double immuno-fluorescence of various neurofilaments (green)—NF-H (C), NF-M (F) and NF-L (I) with polyclonal peripherin antibody (red) on the TDP-43$^{G348C}$ spinal cord sections reveal that NF-H is recruited to peripherin aggregates (arrows, E), and to a lesser extent NF-H (H), but not NF-L (K). Scale bar: 25 µm.

Figure 21:
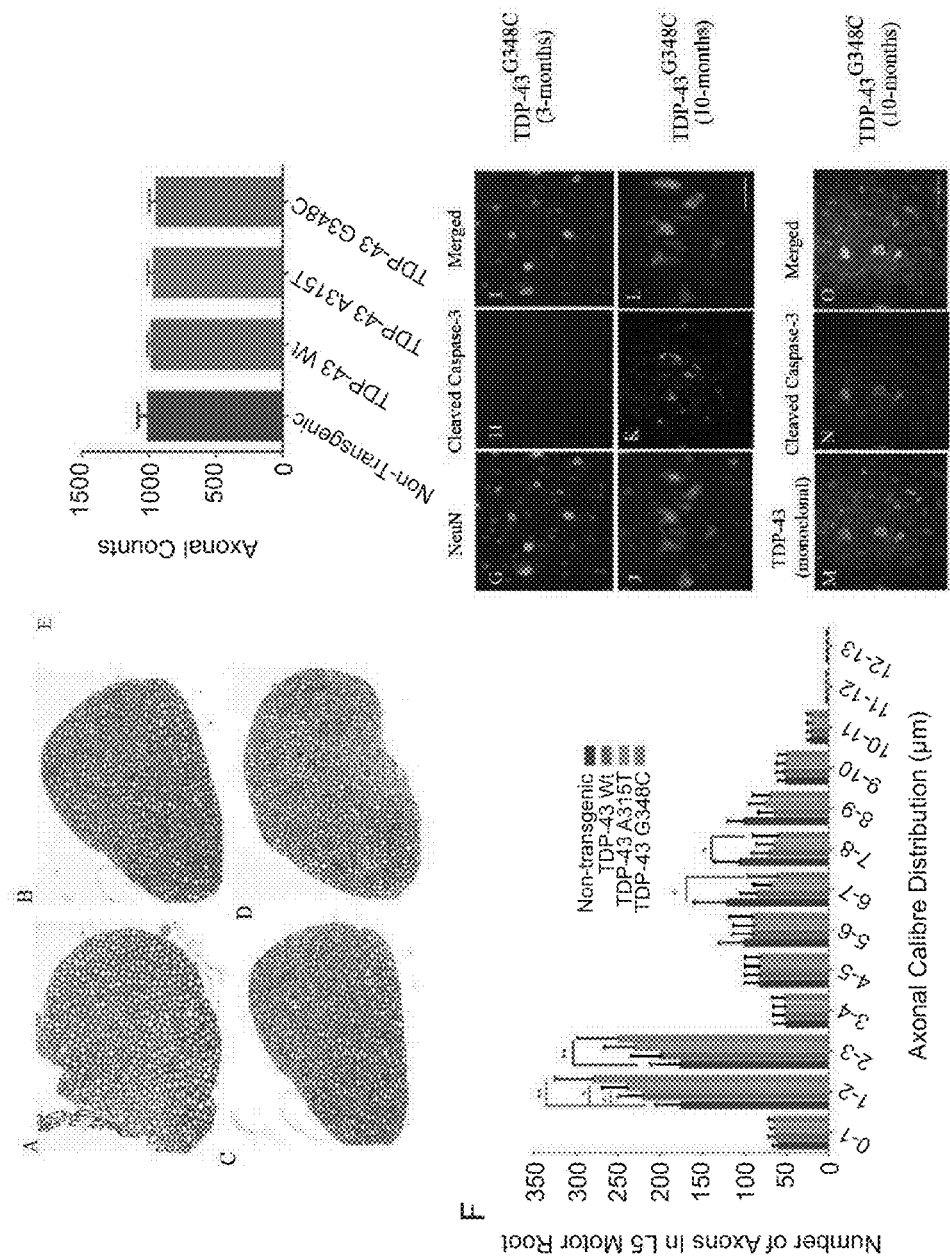
Figure 22:
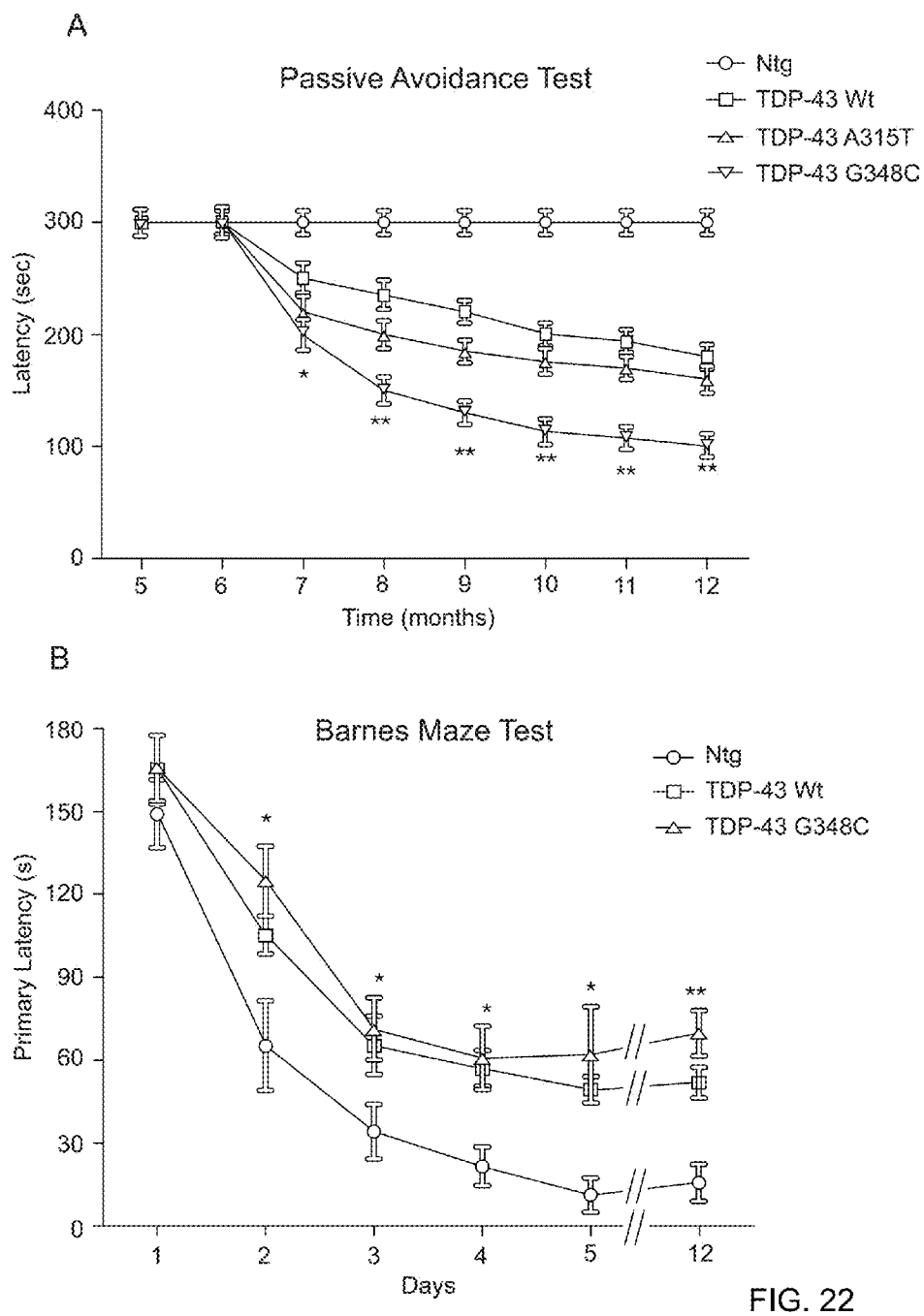
Figure 22:
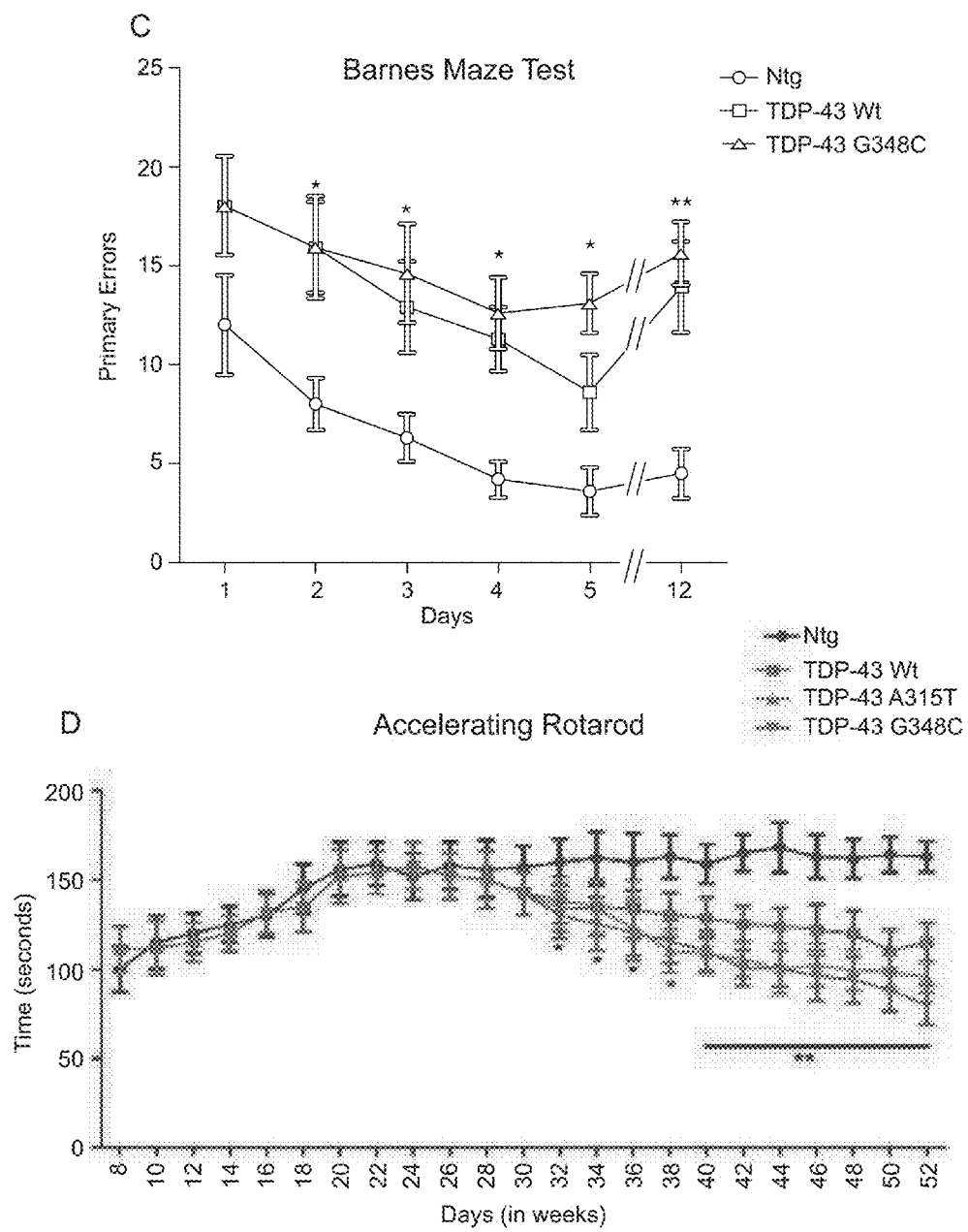

FIG. 21. Reduced axonal calibre in ventral roots of TDP-43 transgenic mice. (A-D) Toluidine blue staining of thin sections of L5 ventral root axons from non-transgenic (A), TDP-43$^{Wt}$ (B), TDP-43$^{A315T}$ (C) and TDP-43$^{G348C}$ (D) mice showing no significant differences in the motor neuron count. (E) Axonal counts of transgenic mouse at 10-months age failed to reveal any significant differences in the number of motor axons in the L5 ventral root. (F) Cumulative axon calibre distribution of axons at L5 ventral root of 10-months old non-transgenic and transgenic mice showing increased number of 1- to 3-µm axons and reduced number of 6- to 9-µm axons in TDP-43$^{G348C}$ mice. A two-way ANOVA with repeated measures was used to study the effect of group (transgenic and non-transgenic mice) on axonal calibre distribution. Pairwise comparisons were made using Bonferroni adjustment *p<0.01 and **p<0.001. Data shown are means±SEM of 5 different mice from each group. (G-L) Double immunofluorescence using NeuN (a neuronal marker) and cleaved caspase-3 show many cleaved caspase-3 positive neurons in the spinal cord of TDP-43$^{G348C}$ mice at 10-months age (L) compared to 3-months old TDP-43$^{G348C}$ mice (I). (M-O) Double immunofluorescence using human specific TDP-43 and cleaved caspase-3 show many cleaved caspase-3 positive neurons in the spinal cord of TDP-43$^{G348C}$ mice at 10-months age. Scale bar: 25 µm FIG. 22. TDP-43 transgenic mice develop cognitive defects and motor dysfunction. A. Passive avoidance test of various transgenic mice was performed every month from 5 up to 12-months. Mice were placed in the light chamber, and mice entering in the dark chamber received a small shock. Each test set lasted for 2 days and on the 3$^{rd}$ day, contextual learning/memory of the mice was evaluated based on latency (in seconds) to enter the dark chamber. A two-way ANOVA with repeated measures was used to study the effect of group (transgenic and non-transgenic mice) and time (in months) on latency to go to the dark chamber. Pairwise comparisons were made using Bonferroni adjustment. TDP-43$^{G348C}$ mice showed significant deficits in contextual learning/memory at 7-months age (*p<0.01), while TDP-43$^{A315T}$ and TDP-43$^{Wt}$ mice showed significant deficiencies at 9-months age (**, p<0.001) as compared to non-transgenic control (Ntg). The cut-off time was 300 sec; data shown are means±SEM of 10 different mice from each group. (B) Barnes maze test was performed on 10-months old mice (TDP-43$^{Wt}$, TDP-43$^{G348C}$ and Ntg). The spatial learning/memory capabilities are expressed as the primary latencies (latency to enter the target quadrant) exhibited in five consecutive sessions and one session at Day 12 of the test for long-term learning/memory analysis. A two-way ANOVA with repeated measures followed by bonferroni adjustment was used for statistical analysis. TDP-43$^{G348C}$ and to a lesser extent TDP-43$^{Wt}$ transgenic mice have severe spatial learning/memory deficits even at Day 2, which became increasingly prominent at Day 5. Long-term memory of TDP-43$^{G348C}$ and TDP-43$^{Wt}$ mice are also severely impaired as assessed at Day 12 (*p<0.01, **p<0.001). Results represent means±SEM of three independent trials (n=6 mice/group). (C) The spatial learning/memory capabilities are also expressed as the primary errors (number of errors before entering the target quadrant) exhibited in five consecutive sessions and one session at Day 12 of the test for long-term learning/memory analysis. TDP-43$^{G348C}$ and to a lesser extent TDP-43$^{Wt}$ transgenic mice have severe spatial learning/memory deficits even at Day 2, which became increasingly prominent at Day 5. Long-term memory of TDP-43$^{G348C}$ and TDP-43$^{Wt}$ mice are also severely impaired as assessed at Day 12 (*p<0.01, **p<0.001). Results represent means±SEM of three independent trials (n=6 mice/group). (D) Accelerating rotarod analysis of mice at various ages from 8-weeks to 52-weeks reveal that TDP-43$^{G348C}$ mice had significant differences in rotarod latencies at 36-weeks of age, TDP-43$^{A315T}$ at 38-weeks and TDP-43$^{Wt}$ at 42-weeks of age as compared to non-transgenic control mice. A two-way ANOVA with repeated measures followed by bonferroni adjustment was used for statistical analysis, *p<0.01, **p<0.001. Data represent means±SEM of three independent trials (n=12 mice/group).

FIG. 23. Neuroinflammation in TDP-43 transgenic mice. (A-H). Immunofluorescence of the spinal cord (A-E) and brain (F-J) sections of Ntg (non-transgenic), TDP-43$^{Wt}$, TDP-43$^{A315T}$ and TDP-43$^{G348C}$ mice was performed using anti-Iba-1 antibody. In the spinal cord microglial proliferation was abundant in 10-months old TDP-43$^{G348C}$ mice (E), followed by age-matched TDP-43$^{A315T}$ (D) and TDP-43$^{Wt}$ mice (C) as compared to non-transgenic control mice (A) and 3-months old TDP-43$^{G348C}$ mice (B). In brains sections also, microgliosis was intense in TDP-43$^{G348C}$ mice (J) as well as in age-matched TDP-43$^{A315T}$ (I) and TDP-43$^{Wt}$ (H) as compared to non-transgenic control mice (F) and 3-months old TDP-43$^{G348C}$ mice (G). K-T. Immuno-fluorescence of the spinal cord (K-O) and brain (P-T) sections of Ntg, TDP-43$^{Wt}$, TDP-43$^{A315T}$ and TDP-43$^{G348C}$ mice was performed using anti-GFAP antibody. In the spinal cord astroglial proliferation was abundant in 10-months old TDP-43$^{G348C}$ mice (O), followed by age-matched TDP-43$^{A315T}$ (N) and TDP-43$^{Wt}$ (M) as compared to non-transgenic control mice (K) and 3-months old TDP-43$^{G348C}$ mice (L). In brains sections also, microgliosis was abundant in TDP-43$^{G348C}$ mice (T) followed by age-matched TDP-43$^{A315T}$ (S) and TDP-43$^{Wt}$ (R) as compared to non-transgenic control mice (P) and 3-months old TDP-43$^{G348C}$ mice (Q). (U). Quantitative real-time PCR was performed on spinal cord tissue samples from 10-months old TDP-43$^{Wt}$, TDP-43$^{A315T}$ and TDP-43$^{G348C}$ transgenic mice and expressed as fold change over non-transgenic control littermates normalized to Atp-5a levels. One-way ANOVA was used with Tukey's post-hoc comparison for statistical analysis (n=5 mice/ group), *p<0.01, p<0.001. The levels of TNF-α (2.7-fold, p<0.001), IL-6 (2-fold, *p<0.01), and MCP-1 (2.5-fold, **p<0.001) were upregulated in TDP-43$^{G348C}$ mice as compared to TDP-43$^{Wt}$ mice. Data represent means±SEM of three independent experiments. Scale bars: A-T 50 μm.

Figure 24:
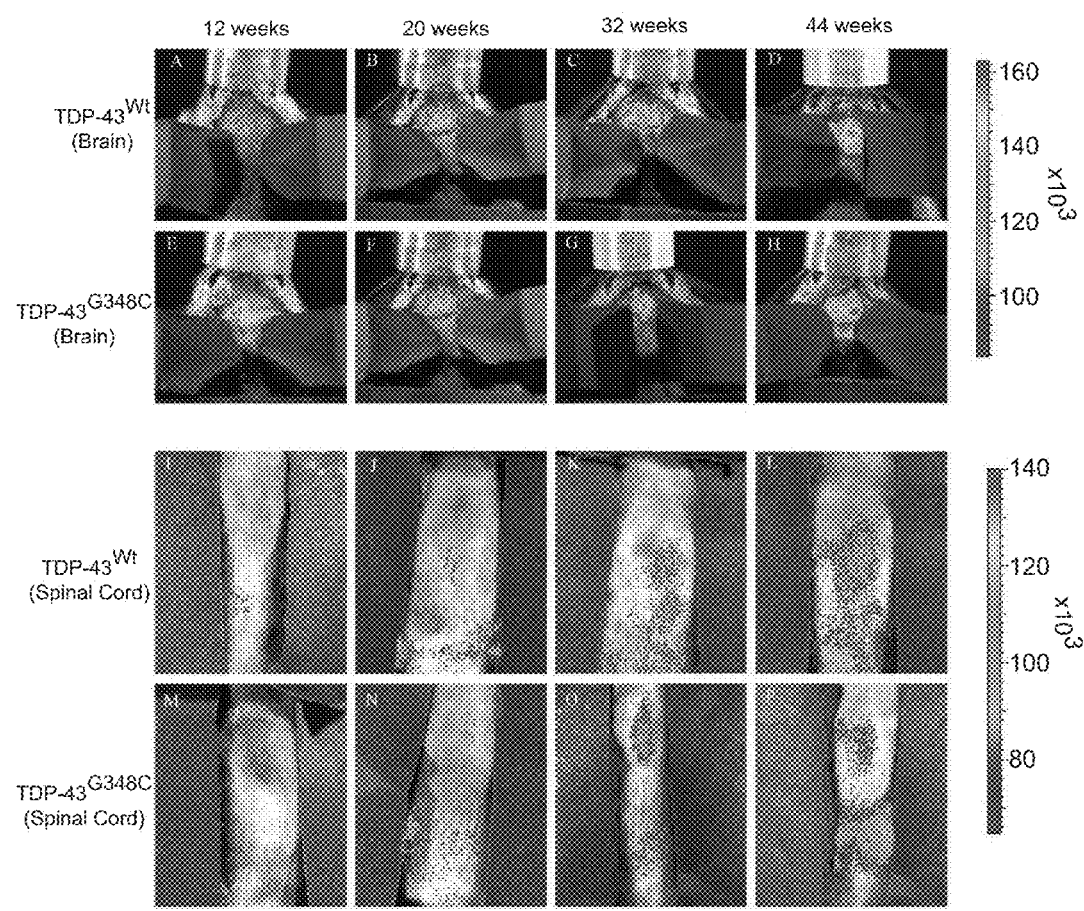
Figure 24:
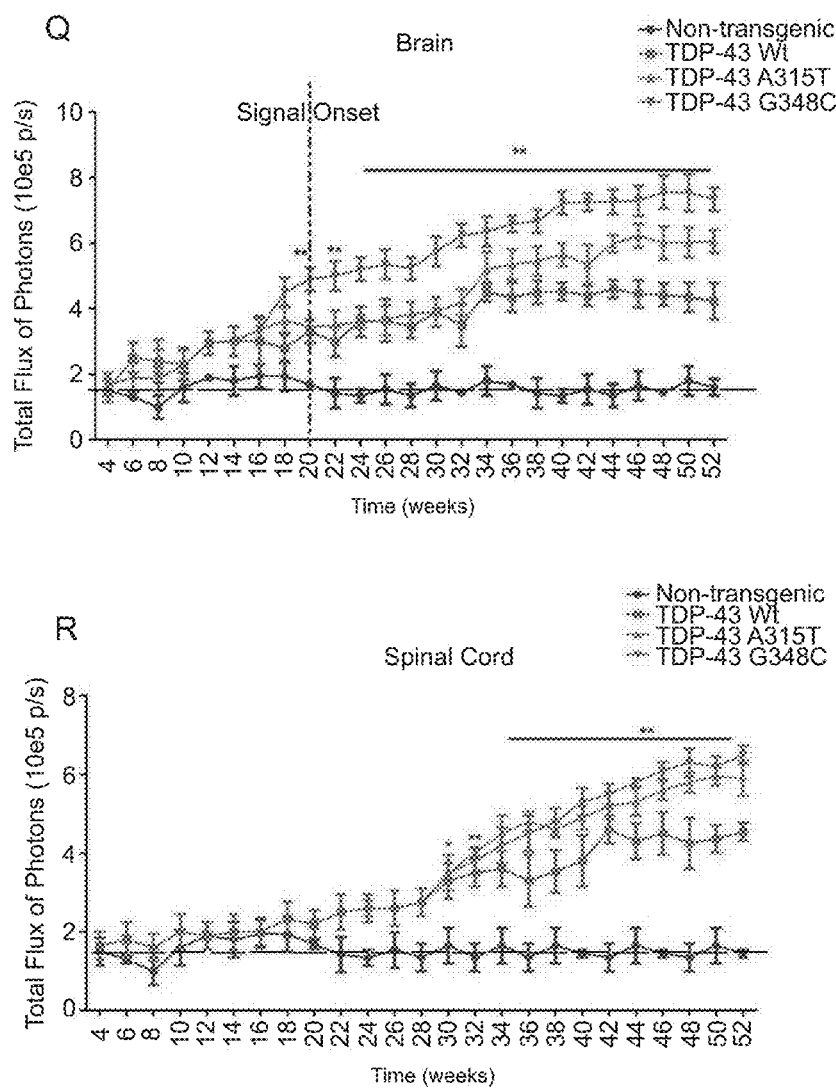

FIG. 24. In vivo imaging revealed onset of astrocytosis before onset of behavioural impairments in doubly transgenic mice TDP-43/GFAP-luc. A-H. In vivo bioluminescence imaging of astrocytes activation was studied at various time points in the brain of GFAP-luc/TDP-43$^{Wt}$ (A-D) and GFAP-luc/TDP-43$^{G348C}$ (E-H) mice. Note that the GFAP-luc/TDP-43$^{G348C}$ (F) mice had significant increase of GFAP promoter activity at 5-months (20-weeks) age compared to GFAP-luc/TDP-43$^{Wt}$ (B) mice. I-P. Typical sequence of images of the spinal cord area obtained from of GFAP-luc/TDP-43$^{Wt}$ (I-L) and GFAP-luc/TDP-43$^{G348C}$ (M-P) mice at different time points by in vivo imaging. Significant GFAP promoter activity can be observed in GFAP-luc/TDP-43$^{Wt}$ (K) and GFAP-luc/TDP-43$^{G348C}$ (O) mice at 8-months (32-weeks) age. Q-R: Longitudinal quantitative analysis of the total photon GFAP-signal/bioluminescence (total flux of photon/s) in GFAP-luc/TDP-43$^{Wt}$, GFAP-luc/TDP-43$^{A315T}$ and GFAP-luc/TDP-43$^{G348C}$ mice in the brain (Q) and spinal cord (R). A two-way ANOVA with repeated measures followed by bonferroni adjustment was used for statistical analysis, *p<0.01, **p<0.001. Data represent means±SEM of three independent experiments (n=12 mice/group).

Figure 25:
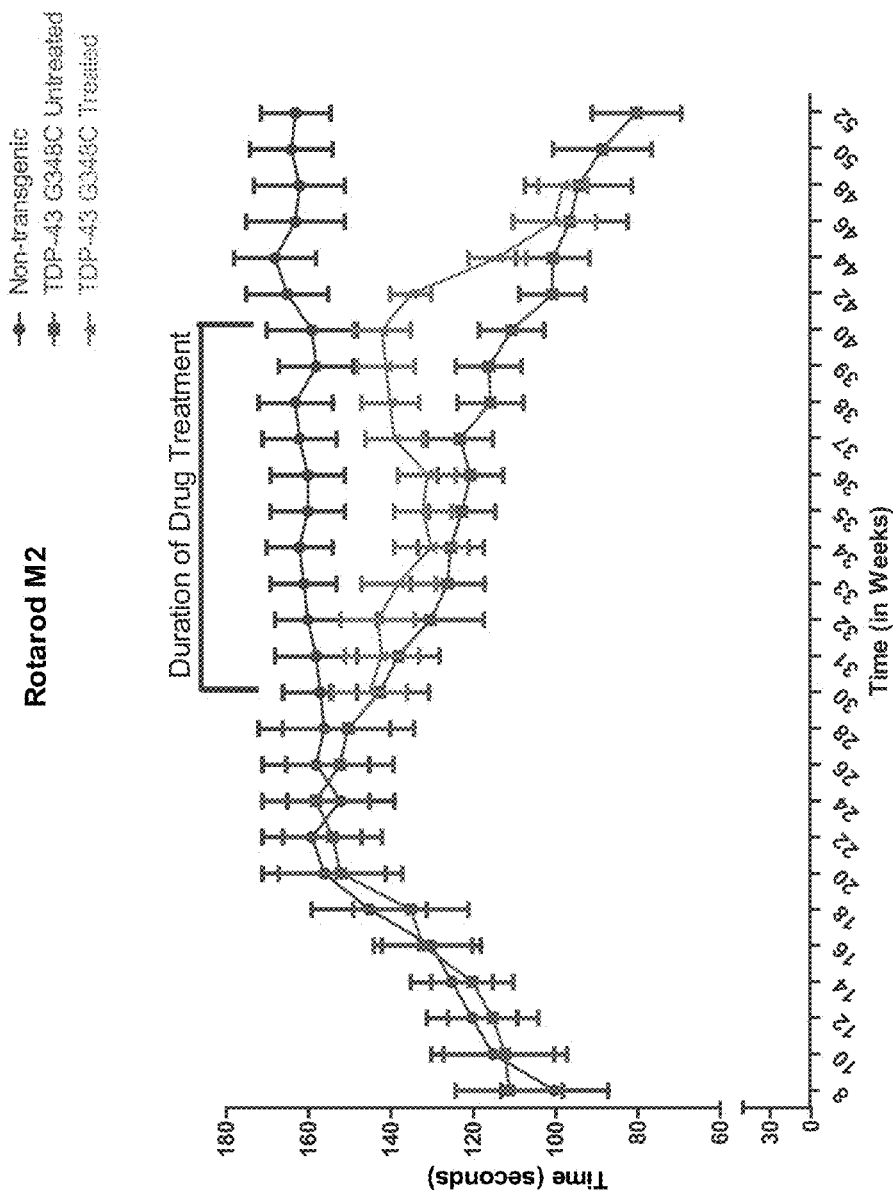

FIG. 25. Withaferin A ameliorates motor defects in TDP-43$^{G348C}$ mice

The term "subject" refers to any subject susceptible of suffering or suffering from neurodegenerative disease. Specifically, such a subject may be, but not limited to, human, an animal (e.g. cat, dog, cow, horse, etc.). More specifically, the subject consists of a human.

The terms "predisposed" and "suspected" refer to a subject who does not yet experience or display the pathology or symptomatology of the disease but who may has increased probability or increased risk of developing neurodegenerative disease.

The expression "neurodegenerative disease" refers to the progressive loss of structure or function of neurons such as ALS, frontotemporal lobar degeneration, Alzheimer, motor neuron disease or Parkinson. Neurodegenerative disease also relates to disease in which TDP-43 is involved. In one embodiment, the neurodegenerative disease is associated with TDP-43 proteinopathy.

TDP-43 polypeptides as well as polynucleotides are well known in the art. For example see NM_007375.3, Gene Bank AK222754.1 or UniProt Q13148 Representative polypeptide sequence (SEQ ID NO:1) and polynucleotide sequence (SEQ ID NO: 2).

In one aspect, TDP-43 may comprise 2 RRM domains (RNA Recognition Motif) (amino acids 106-176 and 191-262 as shown in the examples), a NLS (Nuclear Localization Signal) domain, a N-terminal domain (amino acids 1-105) and a C-terminal domain (amino acids 274-414).

In one embodiment, TDP-43 polypeptide includes a sequence at least 65% to 95% identical, at least 65%, 70%, 75%, 80%, 85%, 90% identical or at least 95% identical to part or all of the sequence shown in SEQ ID NO. 1 or fragment thereof.

In one embodiment, TDP-43 polynucleotide includes a sequence at least 65% to 95% identical, at least 65%, 70%, 75%, 80%, 85%, 90% identical or at least 95% identical to part or all of the sequence shown in SEQ ID NO. 2 or fragment thereof.

p65 polypeptides as well as polynucleotides are well known in the art. For example see M62399.1. Representative polypeptide sequence (SEQ ID NO:3) and polynucleotide sequence (SEQ ID NO:4).

In another aspect, p65 may comprise RRM1 (amino acids 104-200), RRM2 (amino acids 191-262) and Glycine rich domains (amino acids 275-413) as well as a NLS domain (amino acids 82-98).

In another embodiment, p65 polypeptide includes a sequence at least 65% to 95% identical, at least 65%, 70%, 75%, 80%, 85%, 90% identical or at least 95% identical to part or all of the sequence shown in SEQ ID NO. 3 or fragment thereof.

In one embodiment, p65 polynucleotide includes a sequence at least 65% to 95% identical, at least 65%, 70%, 75%, 80%, 85%, 90% identical or at least 95% identical to part or all of the sequence shown in SEQ ID No. 4 or fragment thereof.

Techniques for determining nucleic acid and amino acid "sequence identity" are also known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity which can be used in the context of the present invention is the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix BLOSUM62; Descriptions=50 sequences; sort by=HIGH SCORE;

Databases=non-redundant, GenBank+EMBL+DDBJ+PDB+GenBank CDS translations+Swiss protein+Spupdate+PIR.

The term "polypeptide or fragments thereof" as used herein refers to peptides, oligopeptides and proteins. This term also does not exclude post-expression modification of polypeptides. For example, polypeptides that include the covalent attachment of glycosyl groups, acetyl groups, lipid groups and the like are encompassed by the term polypeptide. The term "fragment thereof", as used herein, refers to polypeptide that may comprise for example 50%, 60%, 70%, 80%, 90%, 95% or more of the polypeptide sequence of the full length reference polypeptide. In one aspect the fragment is a fragment that is functional (e.g. retains the activity of the complete polypeptide or polynucleotide)

TDP-43 polypeptide functional fragments that interact with p65 include TDP-43 fragments spanning the RRM-I domain (amino acids 98-176) and/or the N-terminal domain (amino acids 31-81) of TDP-43 polypeptide.

The term "antibody" is intended herein to encompass monoclonal antibody and polyclonal antibody.

The term "mRNA" refers to mRNA or cDNA sequence of more than one nucleotide in either single or duplex form. The mRNA in accordance with the invention may be isolated by any known method. TDP-43 mRNA and p65 mRNA refer to mRNA sequences encoding TDP-43 and p65 polypeptides, respectively.

As used herein, the term "sample" refers to a variety of sample types obtained from a subject and can be used in a diagnostic assay. The definition encompasses blood, urine, cerebrospinal fluid and other liquid samples of biological origin. The definition also encompass solid tissue samples such as a biopsy of specimen or tissue culture or cells derived therefrom such as cortical neurons, microglial cells, myeloid cells or spinal cord extract.

As used herein, the interaction of TDP-43 with p65 refers to an interaction sufficient to activate NF-κB p65 pathway. The interaction may be for example, ionic, non-covalent or covalent binding of TDP-43 with p65. The level of interaction between TDP-43 and p65 may be detected and quantified within the biological sample. The detection of TDP-43 interacting with p65 may involve a detecting agent, which may be for instance, a specific antibody such as a purified monoclonal or polyclonal antibody raised against TDP-43. In such a case, the determination of interaction between TDP-43 and p65 is achieved by contacting a TDP-43 specific antibody with the biological sample under suitable conditions. As known in the art a second detecting agent, which may be, for instance a specific antibody such as a purified monoclonal or polyclonal antibody raised against p65 is needed to measure the interaction between TDP-43 and p65 within the biological sample. In such a case, the determination of interaction between TDP-43 and p65 is achieved by contacting a p65 specific antibody with TDP-43-antibody complex under suitable conditions to obtain a TDP-43-antibody-p65-antibody complex. The determination of interaction between TDP-43 and p65 in the biological sample may also be performed by contacting a p65 specific antibody with the biological sample under suitable conditions prior to contacting the biological sample with a TDP-43 specific antibody. Techniques for determining or measuring interaction between polypeptides are well known in the art and may include for example SDS-PAGE, ELISA, immunoprecipitation, co-immunoprecipitation, Western Blot assay, immunostaining, EMSA supershift or radioimmunoassay.

In one aspect, p65 interacts with the N-terminal portion of TDP-43. In another aspect, p65 polypeptide interacts with one of the RRM domain of TDP-43 such as RRM domain of amino acids 106-176.

As used herein, the expression "reference level" of a given polypeptide or polynucleotide refers to a level of polypeptide or polynucleotide present in a healthy subject i.e. not suffering from a neurodegenerative disease or as the case may be the level of the subject at different points for evaluating the progression of the disease.

In accordance with this invention, an elevated level of interaction between TDP-43 and p65 is indicative of the subject's risk of being predisposed to developing a neurodegenerative disease or suffering from a neurodegenerative disease or as the case may be is indicative of the progression of the disease in the subject. When the level of interaction between TDP-43 and p65 in the subject to be tested and the level of interaction between TDP-43 and p65 in a healthy subject are substantially identical, the subject's risk of being predisposed to developing a neurodegenerative disease or suffering from a neurodegenerative disease may be low. When the difference in the levels of interaction between TDP-43 and p65 in the subject to be tested and the level of interaction between TDP-43 and p65 in healthy subject increases, the risk of the subject being predisposed to developing a neurodegenerative disease or suffering from a neurodegenerative disease also increases. For example, an elevated level of interaction between TDP-43 and p65 could be at least 1.8 fold higher than the reference level.

In accordance with this invention, an elevated level of TDP-43 and/or p65 mRNA is indicative of the subject's risk of being predisposed to developing a neurodegenerative disease or suffering from a neurodegenerative disease or as the case may be is indicative of the progression of the disease in the subject. When the levels of TDP-43 and/or p65 mRNA in the subject to be tested and the level of TDP-43 and/or p65 mRNA in a healthy subject are substantially identical, the subject's risk of being predisposed to developing a neurodegenerative disease or suffering from a neurodegenerative disease is low. When the difference in the levels of TDP-43 and/or p65 mRNA in the subject to be tested and the level of TDP-43 and/or p65 mRNA in the healthy subject is increased, the risk of being predisposed to developing a neurodegenerative disease or suffering from a neurodegenerative disease is also increased. For example an elevated level of TDP-43 mRNA could be at least 2.5 folds higher than the reference level and the elevated level of p65 mRNA could be at least 4-folds higher than the reference level.

In accordance with this invention, the level of mRNA in the biological sample can be determined by methods well known in the art, for example by PCR or hybridization assays. Primers used for determining the level of TDP-43 mRNA may be the nucleic acid sequences set forth in SEQ ID NOs. 5 and 6 (SEQ ID NO. 5: GCGGGAAAAG-TAAAAGATGTC, SEQ ID NO. 6: ATTCCTGCAGC-CCGGGGGATCC) and primers used for determining the level of p65 mRNA may be the nucleic acid sequences set forth in SEQ ID NOs. 7 and 8 (SEQ ID NO. 7: GAGC-GACTGGGGTTGAGAAGC, SEQ ID NO. 8: CCCATAG-GCACTGTCTTCTTTCACC).

As used herein, the expressions "TDP-43-specific antibody" and "p65-specific antibody" refer to antibodies that bind to one or more epitopes of TDP-43 or p65 respectively, but which do not substantially recognize and bind to other molecules in a sample containing a mixed population of antigenic molecules.

The term "primer" is used herein to denote a specific oligonucleotide sequence which is complementary to a target nucleotide sequence and used to hybridize to the target nucleotide sequence. As known in the art, a primer is used as an initiation point for nucleotide polymerization catalyzed by DNA polymerase, RNA polymerase, or reverse transcriptase.

The expression "TDP-43 specific primers" or "p65 specific primer" refers to primers that bind to a TDP-43 cDNA or p65 cDNA, respectively but which do not substantially recognize and/or bind to other molecules in a sample containing a mixed population of polynucleotide sequences.

The present invention further provides kits for use with the diagnostic methods of the present invention. Such kits typically comprise two or more components necessary for performing a diagnostic assay. Components may be compounds, appropriate reagents, containers, buffer and/or equipment. For example, one container within a kit may contain at least two specific antibodies wherein one antibody specifically binds to TDP-43 and the other antibody specifically binds to p65 as described herein. One or more additional containers may enclose elements, such as reagents or buffers, to be used in the assay.

Alternatively, a kit may be designed to detect the level of mRNA or cDNA encoded by TDP-43 polypeptide in a biological sample. Such kits generally comprise at least one set of oligonucleotide primers, as described herein, that hybridizes to a polynucleotide encoding TDP-43 polypeptide. Such an oligonucleotide may be used, for example, within a PCR or hybridization assay. Additional components that may be present within such kits include a reagent or container to facilitate the detection or quantification of mRNA encoding TDP-43 polypeptide.

In another aspect, the kit designed to detect the level of mRNA or cDNA encoded by TDP-43 polypeptide may further comprise a second set of oligonucleotide primers that hybridizes to cDNA encoding p65 polypeptide, as described herein.

In another aspect of the present invention, there is provided a method of identifying a candidate compound to determine whether the compound is useful for preventing or treating neurodegenerative diseases. The observation that TDP-43 interacts with p65 (e.g. as a co-activator) in subject strongly indicates a role for NF-κB signaling in neurodegenerative disease as shown herein. Therefore compounds capable of modulating, preventing or reducing activation of NF-κB p65 may be useful in preventing or treating neurodegenerative disease. The methods of the present invention are also useful for screening libraries of compounds in order to identify compounds that may be used as compounds for preventing or treating neurodegenerative disease.

The expression "candidate compound" includes compounds such as small molecules, nucleic acids, antibodies or polypeptides capable of interacting with a biological target molecule, in particular with a protein, in such a way as to modify the biological activity thereof. The expression includes compounds capable of interacting with TDP-43 or p65 in such a way that the interaction between TDP-43 and p65 is modified. In one aspect the compounds are capable of reducing or inhibiting the activation of NF-κB p65.

The expression "biological system" refers to a suitable biological assay or biological model. The biological assay can be an in vitro assay wherein the interaction between p65 and TDP-43 is measured, or the activation of NF-κB p65 is measured. The biological model can be any suitable model allowing the evaluation of the interaction between p65 and TDP-43 or the activation of NF-κB p65. The model can be an organism that has been modified in order to over-express TDP-43 and/or p65. In one embodiment, the model is TDP-43 transgenic mouse. In one embodiment, the TDP-43 transgenic mouse is the transgenic mouse described herein. In another embodiment, the model can be any cell types wherein NF-κB p65 is activated (translocated to the nucleus).

The ability of the compound to modulate, reduce and/or inhibit the activation of NF-κB p65 can be measured by method well known in the art such as ELISA assay, immunoprecipitation assay, coimmunoprecipitation assay, Western Blot assay, immunostaining or radioimmunoassay. NF-κB is known to be involved in pro-inflammatory and innate immune response. Therefore, level of gene activation such as TNF-α, Il-1β, IL-6, or NADPH oxidase 2 could be assessed in order to determine whether or not the candidate compound modulates, reduces and/or inhibits activation of NF-κB p65. Techniques to assess level of gene activation are well known in the art such as reporter gene assays.

In another aspect of the present invention, there is provided a method for monitoring the progression or the regression of a neurodegenerative disease. A higher level of interaction between TDP-43 and p65 over time indicates that the disease progresses whereas a lower level of interaction between TDP-43 and p65 over time indicates that the disease regresses. Monitoring the level of interaction between TDP-43 and p65, over time may be useful in clinical screening wherein a compound is tested on a subject. Therefore, the ability of a compound to modulate, reduce and/or inhibit the activation of NF-κB p65 in a subject can be monitored over a desired period.

Monitoring the level of interaction between TDP-43 and p65 over time can be measured by method well known in the art and as described herein. The interaction levels between TDP-43 and p65 in samples can be monitored during a desired period. For example, a sample can be obtained from a subject at different time such as hourly, daily, weekly, monthly or yearly and the interaction levels between TDP-43 and p65 are determined for each different time. In another embodiment, the level of mRNA of TDP-43 and/or p65 can be monitored during a desired period to determine the progression or the regression of the disease.

Another aspect of the present invention is to provide the use of the interaction level between TDP-43 and p65 as a biochemical marker. The term "biochemical marker" is known to the person skilled in the art. In particular, biochemical markers are gene expression products which are differentially expressed, i.e., upregulated or downregulated, in presence or absence of a certain disease. A biochemical marker can be a protein or peptide and can be for example the level of interaction between TDP-43 and p65 and/or the mRNA level of TDP-43 and/or p65. The level of a biochemical can indicate the presence or absence of the disease and thus allow diagnosis. The biochemical marker can then be used to monitor the progression or the regression of a disease over a desired period.

In one aspect of the present invention, there is provided use of at least one TDP-43 interacting compound or a pharmaceutically acceptable salt thereof or a pharmaceutical composition comprising at least one TDP-43 interacting compound or a pharmaceutically acceptable salt thereof and a pharmaceutical acceptable carrier for treating a subject suffering from a neurodegenerative disease.

In another aspect, there is provided a method for treating a subject suffering from a neurodegenerative disease. The method comprises the step of administering at least one TDP-43 interacting compound or a pharmaceutically acceptable salt thereof or administering a pharmaceutical composition comprising at least one TDP-43 interacting compound or a pharmaceutically acceptable salt and a pharmaceutical acceptable salt thereof to the subject.

The expression "TDP-43 interacting compound" includes compounds such as small molecules, nucleic acids, antibodies or polypeptides capable of interacting with TDP-43 such that the activation of p65 NFκB pathway is reduced or inhibited. The interaction may be for example electrostatic interactions, dipolar interactions, entropic effects or dispersion forces. In one embodiment, the compound may interact with the RRM1 and/or RRM2 domain (amino acids 106-176 and 191-262) of TDP-43 polypeptide. The level of interaction between TDP-43 and the compound may be detected and quantified by known methods such as ELISA, radioimmunoassay, immunoprecipitation assay, Western blot assay, immunostaining assay, EMSA assay, EMSA super shift assay, Chromatin Immunoprecipitation Assay, DNA Pulldown Assay, Microplate Capture and Detection Assay, Reporter Assay or AlphaScreen technology[63].

In one aspect, the compound is a nucleic acid molecule. The expression "nucleic acid molecule" is intended to include DNA molecule (e.g. cDNA or genomic DNA) and RNA molecules (e.g. mRNA). The nucleic acid molecule can be single-stranded or double-stranded. The nucleic acid molecule can be genomic DNA or can be synthesized by known techniques.

In another aspect of the present invention, the nucleic acid molecules comprise the following single-stranded DNA molecules disclosed by Cassel et al.[65]: TG12 (TGTGTGTGTGTGTGTGTGTGTG) (SEQ ID NO:21), TG8 (TGTGTGTGTGTGTGTG) (SEQ ID NO:22), TAR-32 (CTGCTTTTTGCCTGTACTGGGTCTCTGTGGTT) (SEQ ID NO: 23), TG6 (TGTGTGTGTGTG) (SEQ ID NO:24), TG4 (TGTGTGTG) (SEQ ID NO:25) or dAC12 (ACACACACACACACACACACACAC) (SEQ ID NO:26) and the following double-stranded RNA molecules also disclosed by Cassel et al[65]: UG12 (UGUGUGUGUGUGUGUGUGUGUGUG) (SEQ ID NO:27), UG8 (UGUGUGUGUGUGUGUG) (SEQ ID NO:28), UG6 (UGUGUGUGUGUG) (SEQ ID NO:29), UCUU3 (UCUUUCUUUCUU) (SEQ ID NO:30) and rAC12 (ACACACACACACACACACACACAC) (SEQ ID NO:31).

The expression "treating a subject" refers to treatment that halts the progression of, reduces the pathological manifestations of, or entirely eliminates a condition in a patient. Following TDP-43 polypeptide interaction with the nucleic acid molecule, TDP-43 is less likely to interact with p65 thus reducing p65 NFκB activation. As shown herein by reducing p65 NFκB activation, the motor impairment is ameliorated in a subject suffering from a neurodegenerative disease. For instance, the motor impairment can be improved by at least 4% compared to the untreated subject. Methods for qualification and quantification of a reduction in pathological manifestations in a subject suffering from neurodegenerative disease are known in the art such as rotarod performance test, motor control test, postural evoked response, adaptation test or balance strategy analysis, barnes maze task and step-through passive avoidance test.

Nucleic acid molecule can be administered to the subject in an encapsulated form such as liposome, virus, nanocapsule or microsphere as known in the art. Methods for encapsulating nucleic acid molecule are also known in the art.

Another aspect of the invention provides the use of at least one withanolide compound or a pharmaceutically acceptable salt thereof or a pharmaceutical composition comprising at least one withanolide compound or a pharmaceutically acceptable salt thereof and a pharmaceutical acceptable carrier for treating a subject suffering from a neurodegenerative disease.

In another aspect, there is provided a method for treating a subject suffering from a neurodegenerative disease. The method comprises the step of administering at least one withanolide compound or a pharmaceutically acceptable salt thereof or administering a pharmaceutical composition comprising at least one withanolide compound or a pharmaceutically acceptable salt thereof and a pharmaceutical acceptable carrier to the subject.

The term "at least one withanolide compound" refers to steroidal compounds with an ergosterol skeleton in which C-22 and C-26 are oxidized to form a δ-lactone. Withanolide can be isolated from *Withania somnifera* or another *Withania* species. Withanolide can also be semi-synthetically produced from withanolide natural products or can be produced by total synthesis. Examples of known withanolide are: withaferin A, withanolide N, withanolide O, withanolide D, withanolide E, withanolide P, withanolide S, withanolide Q, withanolide R, withanolide G, withanolide H, withanolide I, withanolide J, withanolide K, withanolide U, withanolide Y, analogs or pharmaceutically salt thereof.

In one aspect, the withanolide is withaferin A, an analog, or a pharmaceutically acceptable salt thereof.

The term "analog" includes analogs of withaferin A described in WO2010/053655 and WO2010/030395.

As described herein, withanolide compound such as withaferin-A-treated TDP-43$^{WT}$ or TDP-43$^{G348C}$ transgenic mice show an ameliorated motor impairment of at least 4% compared to their untreated TDP-43$^{WT}$ or TDP-43$^{G348C}$ transgenic mice. Motor behavior can be analysed with known techniques such as rotarod performance test, motor control test, postural evoked response, adaptation test or balance strategy analysis, barnes maze task and step-through passive avoidance test.

As used herein, the term "pharmaceutical composition" refers to the combination of an active agent (e.g., withanolide) with a carrier, inert or active, making the composition especially suitable for therapeutic use.

It is noted in that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers.

The expression "pharmaceutically acceptable salts" are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene p sulphonic, tartaric, acetic, trifluoroacetic, citric, methanesulphonic, formic, benzoic, malonic, naphthalene 2 sulphonic and benzenesulphonic acids. Salts derived from amino acids are also included (e.g. L-arginine, L-Lysine). Salts derived from appropriate bases include alkali metals (e.g. sodium, lithium, potassium) and alkaline earth metals (e.g. calcium, magnesium).

With regards to pharmaceutically acceptable salts, see also the list of FDA approved commercially marketed salts listed in Table I of Berge et al., Pharmaceutical Salts, J. of Phar. Sci., vol. 66, no. 1, January 1977, pp. 1-19.

It will be appreciated by those skilled in the art compounds can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will be appreciated that the amount of compounds required for use in treatment will vary not only with the particular compound selected but also with the route of administration, the nature of the condition for which treatment is required and the age and condition of the patient and will be ultimately at the discretion of the attendant physician.

The desired dose may conveniently be presented in a single dose or as divided dose administered at appropriate intervals, for example as two, three, four or more doses per day. While it is possible that, for use in therapy, the compounds may be administered as the raw chemical it is preferable to present the active ingredient as a pharmaceutical composition. The invention thus further provides a pharmaceutical combination or composition of the compounds as described herein or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The compositions may, where appropriate, be conveniently presented in discrete dosage units and may be prepared by any of the methods well known in the art of pharmacy. All methods include the step of bringing into association the active with liquid carriers or finely divided solid carriers or both and then, if necessary, shaping the product into the desired composition.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds or combinations may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds or combinations are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds or combinations may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

As used herein, the expression "an acceptable carrier" means a vehicle for the combinations and compounds described herein that can be administered to a subject without adverse effects. Suitable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

It will be appreciated that the amount of a compound required for use in treatment will vary not only with the particular compound selected but also with the route of administration, the nature of the condition for which treatment is required and the age and condition of the patient and will be ultimately at the discretion of the attendant physician. In general however a suitable dose will be in the range of from about 0.001 to about 100 mg/kg of body weight per day, for example, in the range of 0.01 to 50 mg/kg/day, or, for example, in the range of 0.1 to 40 mg/kg/day. The compound is conveniently administered in unit dosage form; for example containing 1 to 2000 mg, 10 to 1500 mg, conveniently 20 to 1000 mg, most conveniently 50 to 700 mg of active ingredient per unit dosage form.

In another embodiment of the present invention, dosages may be estimated based on the results of experimental models, optionally in combination with the results of assays of the present invention. Generally, daily oral doses of active compounds will be from about 0.01 mg/kg per day to 2000 mg/kg per day. Oral doses in the range of 10 to 500 mg/kg, in one or several administrations per day, may yield suitable results. In the event that the response of a particular subject is insufficient at such doses, even higher doses (or effective higher doses by a different, more localized delivery route) may be employed to the extent that patient tolerance permits. Multiple doses per day are also contemplated in some cases to achieve appropriate systemic levels of the composition In another aspect, the present invention provides a non-human transgenic animal model suffering from a neurodegenerative disease which can be used as a model for testing therapeutic approaches.

The expression "non-human transgenic animal model" refers to an animal whose genetic material has been altered. In one embodiment, the genome of the animal has been altered to introduce therein a DNA sequence such as human TDP-43 polynucleotide. Methods for creating transgenic animal are known in the art such as DNA microinjection, embryonic stem cell-mediated gene transfer and retrovirus-mediated gene transfer.

The animal model can be a rodent, rat, sheep, monkey, goat, mouse, cat, dog or pig. In one embodiment, the animal model is a mouse.

The term "genome" as used herein refers to an organism's hereditary information. The genome includes both the genes and the non-coding sequences of the DNA/RNA molecule.

The expression "human TDP-43 genomic fragment operably linked to a human TDP-43 promoter" refers to a TDP-43 nucleic acid sequence fragment comprising TDP-43 coding sequence, the introns, the 3' sequence autoregulating TDP-43 synthesis as described by Polymenidou et al 2011 and the human TDP-43 promoter as described in Swamp et al. Brain, 2011, 134, p. 2610-2626. The genomic fragment can be obtained from a library composed of genomic fragments. In one embodiment the TDP-43 genomic fragment linked to its endogenous promoter is obtained from a human bacterial artificial chromosome clone. In another embodiment, the human TDP-43 promoter is ligated upstream of the TDP-43 genomic fragment. Thus the expression of TDP-43 polypeptide is driven by its endogenous promoter. The TDP-43 genomic fragment comprises the 3' auto-regulating TDP-43 synthesis sequence within an alternatively spliced intron in the 3'UTR of the TDP-43 pre mRNA. Methods for obtaining genomic fragments, generating libraries, ligating promoters to nucleic acid sequences are known in the art such as molecular cloning.

The expression "expresses human TDP-43 polypeptide in a moderate level" refers to the animal model expressing human TDP-43 at a level that allows the animal to develop signs of neurological dysfunction. For instance, neurological sign of dysfunction can include increasing TDP-43 polypeptide or mRNA expression, ubiquitinated TDP-43 inclusion, transactive response TDP-43 cleavage fragments, intermediate filament abnormalities, axonopathy, neuroinflammation, memory capabilities, impaired learning and memory capabilities or motor dysfunction. In one embodiment, the animal model develops the neurological dysfunction at about 10 months of age. In one embodiment, the RNA expression level of the human TDP-43 in the transgenic animal model is about 3 fold higher as compared with the RNA level of the animal endogenous TDP-43. Methods for quantifying RNA level expression are known in the art such as quantitative real time PCR or northern blot.

In another embodiment, the human TDP-43 genomic fragment operably linked to the human TDP-43 promoter comprises TDP-43$^{WT}$ sequence isolated from clone RPCI-11, number 829B14, TDP-43$^{A315T}$ sequence having a known mutation at position 315, or TDP-43$^{G348C}$ sequence having a known mutation at position 348 as described in Swamp et al Brain, 2011, 134, p. 2610-2626. The sequences comprising the mutations (TDP-43$^{A315T}$ and TDP-43$^{G348C}$) can be derived from a human genome as mentioned above or the mutations can be inserted within the TDP-43 wild type sequence using site-directed mutagenesis as known in the art.

The expression "amyotrophic lateral sclerosis" is used herein to refer to any neurodegenerative disease that usually attacks both upper and lower motor neurons and causes degeneration throughout the brain and spinal cord.

The expression "frontotemporal lobar degeneration disease" refers to a group of disorders associated with atrophy in the frontal and temporal lobes. Frontotemporal lobar degeneration disease (FTLD) can include FTLD-tau characterized by tau inclusion, FTLD-TDP43 characterized by ubiquitin and TDP-43 inclusion (FTLD-U), FTLD-FUS characterized by FUS cytoplasmic inclusions and dementia lacking distinctive histology (DLDH).

The expression "TDP-43 proteinopathy" refers to neurodegenerative disease associated with the accumulation and/or aggregation of abnormal or misfolded TDP-43 polypeptide.

In another embodiment, the present invention provides an expression cassette comprising the sequence of TDP-43$^{WT}$, TDP-43$^{A315T}$ or TDP-43$^{G348C}$ as described above.

The expression "expression cassette" as used herein refers to the combination of promoter elements with other transcriptional and translational regulatory control elements which are operably linked. A heterologous gene sequence can be inserted into the expression cassette for the purpose of expression of said gene sequence. The expression cassette is capable of directing transcription which results in the production of an mRNA for the desired gene product. The expression cassette is inserted into a plasmid to produce an expression vector. Such an expression vector directs expression of the heterologous protein in host cells.

In another embodiment, there is provided a transgenic cell transformed with the expression cassette as described above. The term "transformed" refers to the DNA-mediated transformation of cells referring to the introduction of the expression cassette DNA into the cells.

In one embodiment, the transgenic cell is obtained from a mouse.

In another embodiment, the present invention provides a method for identifying or confirming whether a compound candidate is useful for preventing and/or treating a neurodegenerative disease. The candidate compound is administered to the non-human transgenic model as defined herein. The effect of the compound on the non-transgenic model is measured by assessing a behavioral task test or by in vivo bioluminescence imaging. When the non-human transgenic model shows an improved behavioral task test or a decrease of neurological dysfunction observed by in vivo bioluminescence it strongly indicates that the candidate compound is useful for preventing or treating the neurodegenerative disease.

The expression "behavioral task test" refers to an experimental task which assesses the capacity of an organism to process environmental cues and respond accordingly. For instance, spatial learning, memory, motor skill, balance, coordination or physical condition of the organism can be measured. Methods for measuring behavioral task are known in the art such as Barnes maze task test, Morris water navigation task, Radial arm task, step-through passive avoidance test and accelerating rotorod test.

In one embodiment, the behavioral task test is the Barnes maze task which refers to a test for measuring spatial learning and memory. The test is described in (Prut et al., 2007).

In a further embodiment, the behavioral task test is the step-through passive avoidance test which refers to an aversive conditioning paradigm in which the subject learns to associate a particular context with the occurrence of an aversive event. For instance, passive avoidance behavior in rodents is the suppression of the innate preference for the dark compartment of the test apparatus following exposure to an inescapable shock.

In another embodiment, the behavioral task test is the accelerating rotorod test which refers to a test for measuring riding time, endurance, balance or coordination. In the test, a subject is placed on a horizontally oriented, rotating cylinder (rod) suspended above a cage floor, which is low enough not to injure the animal, but high enough to induce avoidance of fall. Subjects naturally try to stay on the rotating cylinder, or rotarod, and avoid falling to the ground. The length of time that a given animal stays on this rotating rod is a measure of their balance, coordination, physical condition, and motor-planning. The speed of the rotarod is mechanically driven, and may either be held constant, or accelerated.

The expression <<in vivo bioluminescence imaging>> as used herein refers to the process of light emission in living organism. For instance, 11C-PiB PET could be used to assess change in fibrillar amyloid-beta load in vivo. As also known, luciferase can be used to assess the progression and/or the regression of neurological dysfunction in vivo.

From the data presented here, it is proposed that a TDP-43 deregulation in ALS may contribute to pathogenic pathways through abnormal activation of p65 NF-κB. Several lines of evidence support this scheme: (i) proof of a direct interaction between TDP-43 and p65 NF-κB was provided by immunoprecipitation experiments using protein extracts from cultured cells, from TDP-43 transgenic mice and from human ALS spinal cord samples, (ii) reporter gene transcription assays and gel shift experiments demonstrated that TDP-43 was acting as co-activator of p65 NF-κB through binding of its N-terminal domain to p65, (iii) the levels of mRNAs for both TDP-43 and p65 NF-κB were substantially elevated in the spinal cord of ALS subjects as compared to non-ALS subjects whereas immunofluorescence microscopy of ALS spinal cord samples revealed an abnormal nuclear localization p65 NF-κB, (iv) cell transfection studies demonstrated that an overexpression of TDP-43 can provoke hyperactive innate immune responses with ensuing enhanced toxicity on neuronal cells whereas in neurons TDP-43 overexpression increased their vulnerability to toxic environment, (v) in vivo treatment of TDP-43 transgenic mice with an inhibitor of NF-κB reduced inflammation and ameliorated motor deficits.

This is the first report of an upregulation of mRNAs encoding TDP-43 in post-mortem frozen spinal cords of sporadic ALS. A recent study has provided evidence of increased TDP-43 immuno-detection in the skin of ALS patients[38] but it failed to demonstrate whether this was due to upregulation in TDP-43 mRNA expression. The process that underlies a 2.5-fold increase in TDP-43 mRNA levels in ALS, whether it is transcriptional or mRNA stability remains to be investigated. It seems unlikely that copy number variants could explain an increase of TDP-43 gene transcription as variations in copy number of TARDBP have not been detected in cohorts of ALS[39-41]. Actually, the pathogenic pathways of TDP-43 abnormalities in ALS are not well understood. To date, much attention has been focused of cytoplasmic C-terminal TDP-43 fragments that can elicit toxicity in cell culture systems[42-45]. However, it is noteworthy that neuronal overexpression at high levels of wild-type or mutant TDP-43 in transgenic mice caused a dose-dependent degeneration of cortical and spinal motor neurons but without massive cytoplasmic TDP-43 aggregates[10]. This suggests that an upregulation of TDP-43 in the nucleus rather than TDP-43 cytoplasmic aggregates may contribute to neurodegeneration in these mouse models. As shown here, an overexpression of TDP-43 can trigger pathogenic pathways via NF-κB activation.

The transcription factor NF-κB is a key regulator of hundreds of genes involved in innate immunity, cell survival and inflammation. Since the nuclear translocation and DNA binding of NF-κB are not sufficient for gene induction[46, 47], it has been suggested that interactions with other protein molecules through the transactivation domain[48-50] as well as its modification by phosphorylation[51] might play a critical role. It has been reported that transcriptional activation of NF-κB requires multiple co-activator proteins including CREB-binding protein (CBP)/p300[48,49], CBP-associated factor, and steroid receptor coactivator 1[52]. These coactivators have histone acetyltransferase activity to modify the chromatin structure and also provide molecular bridges to the basal transcriptional machinery. NF-κB p65 was also found to interact specifically with Fused in Sarcoma (FUS) protein, another DNA/RNA binding protein which is involved in ALS[53-55].

The results revealed robust effects of TDP-43 on the activation of NF-κB and innate immune responses. After transfection with TDP-43 species, microglial cells challenged with LPS exhibited much higher mRNA levels for pro-inflammatory cytokines, Nox-2 and NF-κB mRNA when compared to untransfected cells after LPS stimulation. TDP-43 overexpression makes microglia hyperactive to immune stimulation resulting in enhanced toxicity toward neighbouring neuronal cells with involvement of reactive oxygen species (ROS) and increased nitrite levels (NO). Moreover, the adverse effects of TDP-43 upregulation are not limited to microglial cells. Primary cortical neurons overexpressing TDP-43 transgenes by ~3-fold exhibited increased susceptibility to the toxic effects of excess glutamate or LPS-activated microglia (FIG. 13A).

Figure 4:
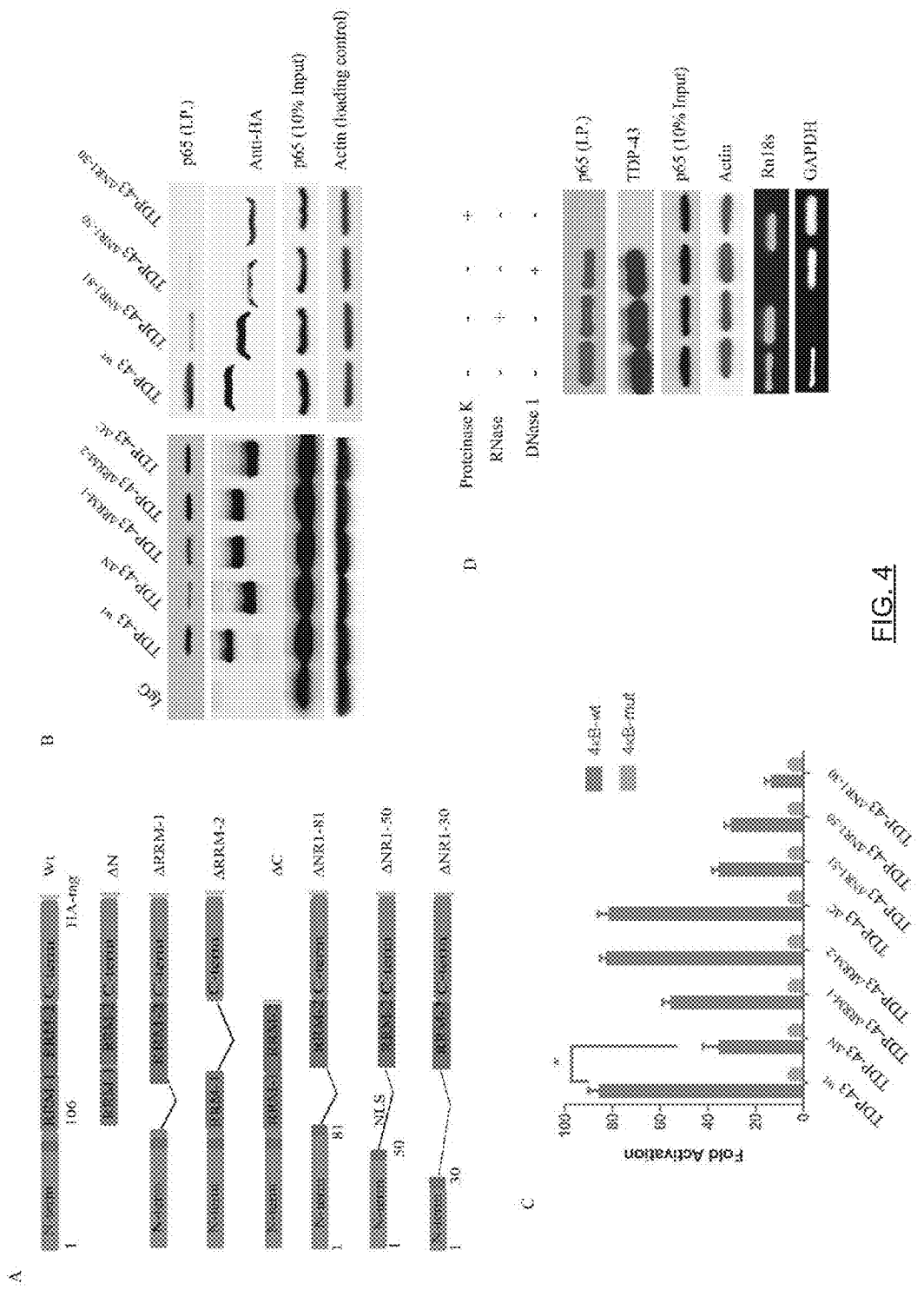
FIG. 4. The N-terminal and RRM-1 domains of TDP-43 are crucial for interaction with p65. (A) 2-dimensional cartoon of TDP-43 protein showing various deletion mutants used in this study. Deletion mutants TDP-43$^{\Delta N}$ (1-105AAs), TDP-43$^{\Delta RRM-1}$ (106-176AAs), TDP-43$^{\Delta RRM-2}$ (191-262AAs) and TDP-43$^{\Delta C}$ (274-414AAs) and full-length TDP-43 (TDP-43$^{wt}$) are shown. Serial N-terminal and RRM-1 domain deletion mutants are also shown. TDP-43$^{NR1-81}$ (98-176AAs), TDP-43$^{\Delta NR1-50}$ (51-81 and 98-176 AAs) and TDP-43$^{\Delta NR1-30}$ (31-81 and 98-176 AAs) were generated. (B) All constructs (Wt and deletion mutants) were cloned in pcDNA3.0 with HA tag at extreme C-terminal of the encoded protein. BV-2 cells were transfected with TDP-43$^{Wt}$ or deletion constructs and pCMV-p65. 24 hrs after transfection, cells were harvested and immunoprecipitated with anti-HA antibody. The immunoprecipitates were fractionated by SDS-PAGE and immunoblotted with mouse monoclonal anti-p65 antibody. TDP-43$^{\Delta N}$ could immunoprecipitate p65 to much lower levels than TDP-43$^{Wt}$ indicating that N-terminal domain is important for TDP-43 interaction with p65. On the other hand, TDP-43$^{\Delta RRM-2}$ and TDP-43$^{\Delta C}$ had no effect on interaction with p65. TDP-43$^{\Delta RRM-1}$ could immunoprecipitate p65 partially suggesting that it also interacts with p65, but to a lesser extent. Further analysis reveals that TDP-43 interacts with p65 through its N-terminal domain (31-81 and 98-106 AAs) and RRM-1 (107-176 AAs) domain (C) Various deletion mutants of TDP-43 were co-transfected along with 4κB$^{wt}$-luc (containing wild type NF-κB binding sites) or 4κB$^{mut}$-luc (containing mutated NF-κB binding sites). 48 h after transfection, luciferase activity was measured. Unlike full length TDP-43$^{wt}$, TDP-43$^{\Delta N}$ had reduced effect (2-fold, * p<0.05) on the gene activation. TDP-43$^{\Delta RRM-1}$ had similar effects like that of TDP-43$^{\Delta N}$ but to a much lesser extent, while TDP-43$^{\Delta NR3}$ had the most prominent effect (6-fold) on gene activation. On the other hand, TDP-43$^{\Delta RRM-2}$ and TDP-43$^{\Delta C}$ deletion mutants had effects similar to full length TDP-43$^{wt}$. Error bars represent mean±SEM. (D) TDP-43 antibody was added to BV-2 transfected cell lysates and proteins were co-immunoprecipitated. After TDP-43 immunoprecipitation, samples were treated with either proteinase K, RNase or DNase 1. Proteinase K was added to a final concentration of 1 μg/ml, RNase A and RNase T1 (Roche) to 1 μg/ml final concentration or DNase 1 at a final concentration of 1 μg/ml. To monitor the effectiveness of RNase and DNase digestion, RNase or DNase were added to cell lysates before immunoprecipitation and subjected to PCR. GAPDH RT-PCR was used to monitor RNase digestion, while Rn18s gene (which codes for 18SrRNA) genomic PCR was used to monitor DNase digestion. Immunoprecipitation experiments were then carried out as usual.
Figure 6:
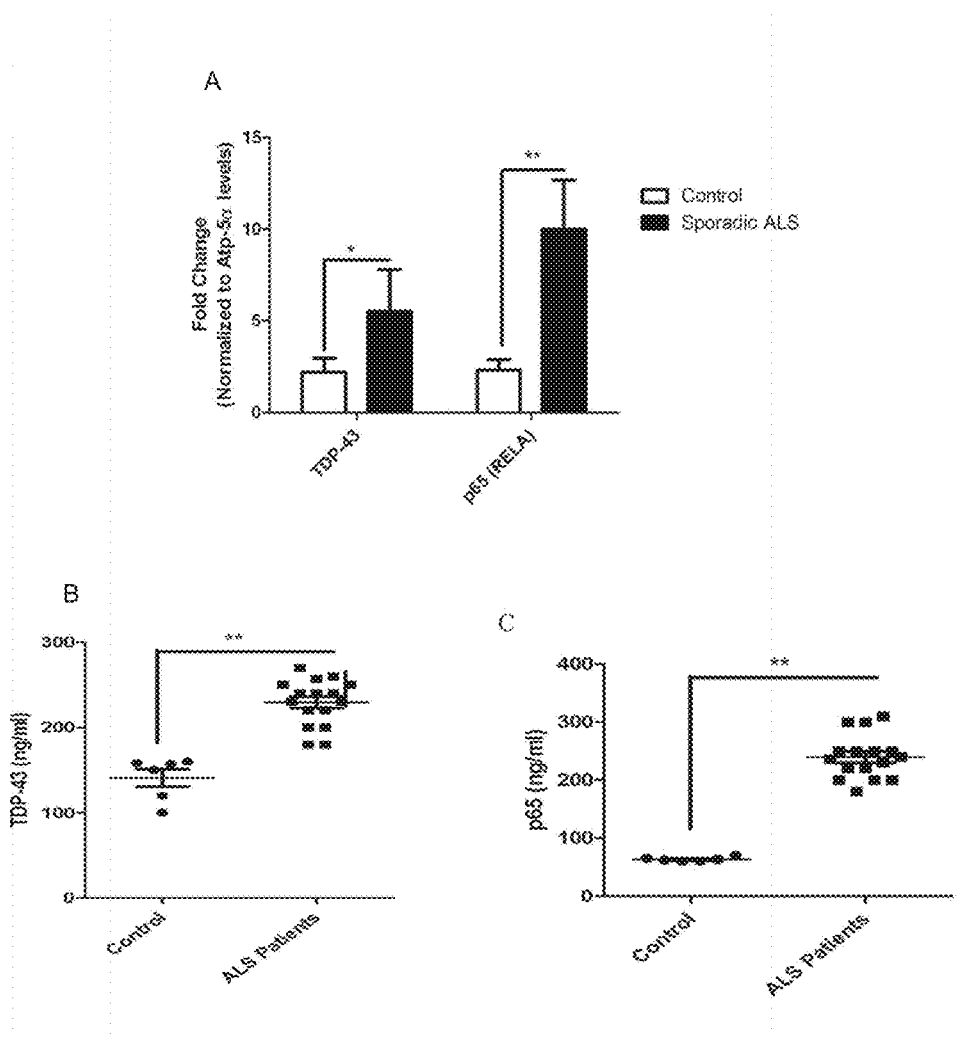
FIG. 6. Analysis of TDP-43 and NF-κB p65 mRNA expression in sporadic ALS spinal cord. Spinal cord tissue samples from 16 different sporadic ALS patients and 6 controls were subjected to real-time RT-PCR analysis using primers specific for TDP-43 (TARDBP) and p65 (RELA). TDP-43 mRNA levels are upregulated by ~2.5-fold (*, p<0.01) in ALS cases as compared to control cases. Similarly, p65 levels are upregulated by ~4-fold (, p<0.001) in ALS cases as compared to control. (B) We performed sandwich ELISA for TDP-43 using TDP-43 monoclonal and polyclonal antibodies. After coating the ELISA plates with TDP-43 monoclonal antibody, we incubated the plate with the protein lysates (containing both soluble and insoluble fragments in between) followed by TDP-43 polyclonal antibody and subsequent detection. The ELISA results suggest that TDP-43 protein levels are upregulated in total spinal cord protein extracts of ALS cases (n=16) by 1.8-fold (253.2±10.95 ng/ml, p<0.001) as compared to control cases (140.8±6.8 ng/ml, n=6). (C) For p65 ELISA, we used an ELISA kit from SABioscience, Qiagen. The levels of p65 were also upregulated in total spinal cord extracts of ALS cases (n=16) by 3.8-fold (242.8±9.5 ng/ml, **p<0.001) as compared to control cases (63.33±2.8 ng/ml, n=6) All real-time RT-PCR values are normalized to Atp-5α levels. Error bars represent mean±SEM.

The presence of ALS-linked mutations in TDP-43 (A315T or G348C) did not affect the binding and activation of p65 NF-κB. This is not surprising because the deletion mutant analysis revealed that a region spanning part of the N-terminal domain and RRM1 of TDP-43 is responsible for interaction with p65 whereas most TDP-43 mutations in ALS occur in the C-terminal domain, which is dispensable for p65 NF-κB activation (FIG. 4). In fact, the cytotoxicity assays with primary cells from TDP-43 transgenic mice revealed that, at similar levels of mRNA expression, the adverse effects of mutant TDP-43 were more pronounced than TDP-43$^{wt}$. These results could be explained by the observation that ALS-linked mutations in TDP-43 increase its protein stability[56]. From the data presented here, we propose the involvement in ALS of a pathogenic pathway due to nuclear increase in TDP-43 levels (FIG. 6). Recent TDP-43 studies with *Drosophila* suggested that the TDP-43 toxicity may occur in absence of inclusions formation and that neurotoxicity requires TDP-43 RNA-binding domain[57]. These results are consistent with the model presented here of TDP-43 toxicity and with data demonstrating interaction of TDP-43 with p65 via the RNA recognition motif RMM1.

Figure 1:
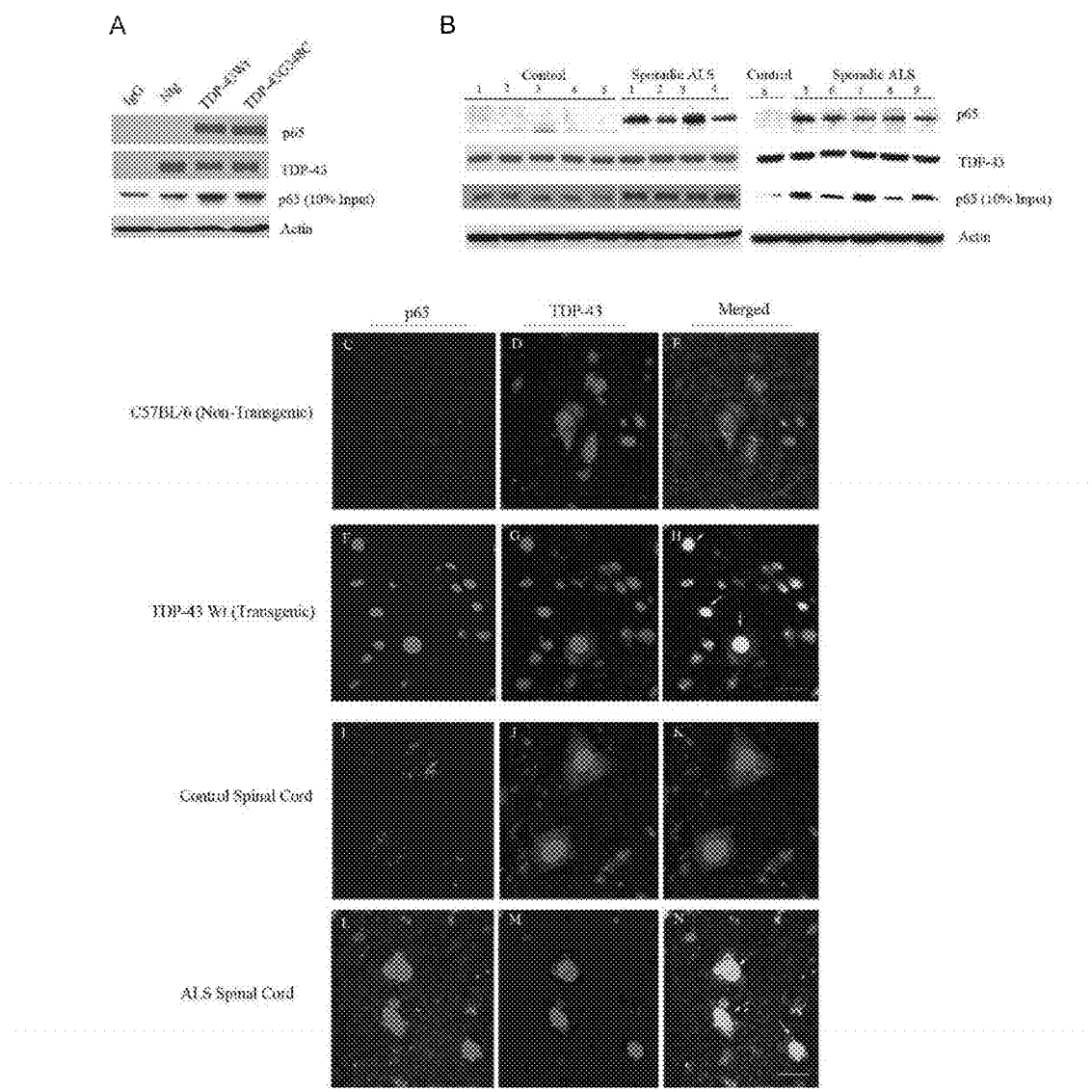
FIG. 1. TDP-43 interacts with NF-κB p65. (A) Total protein extract from spinal cords of TDP-43$^{wt}$, TDP-43$^{G348C}$ transgenic mice and C57Bl/6 non-transgenic (Ntg) mice were immunoprecipitated with anti-TDP-43 (polyclonal) antibody. TDP-43 could co-immunoprecipitate p65, but not IgG (a non-specific antibody). Parallel blot for p65 (Input) was run. (B) Protein extracts from the spinal cords of 9 different sporadic ALS subjects were used for the immunoprecipitation experiments. Using TDP-43 polyclonal antibody, p65 was immunoprecipitated in all the sporadic ALS cases. However, p65 was not immunoprecipitated with TDP-43 in 6 control samples. Western blotting against p65 is shown as 10% input, and Actin as a loading control. Western blots were performed in two sets—one consisting of 5 control cases and 4 ALS cases, while the other of 1 control case (No. 6) and 5 ALS cases (No. 5-9). Parallel blots for TDP-43 and p65 (Input) were run. (C-E) Double-immunofluorescence in the spinal cord of C57Bl/6 non-transgenic mice shows partial co-localization of TDP-43 with p65. (F-H) Spinal cord sections of TDP-43$^{wt}$ transgenic mice show co-localization of TDP-43 and p65 in the nucleus at 90× magnification. (I-K) Spinal cord sections from control subjects were stained for p65 and TDP-43 (polyclonal antibody). Note that TDP-43 only partly co-localizes with inactive p65 in the cytoplasm. (L-N) Spinal cord sections from ALS subjects were treated with immunofluorescent antibodies against p65 and TDP-43. Note the abnormal nuclear detection of p65 with TDP-43 in the nucleus. Brightness and contrast adjustments were made to the whole image to make background intensities equal in control and ALS cases. Shown at 60× magnification. Scale bar=20 µm.
Figure 2:
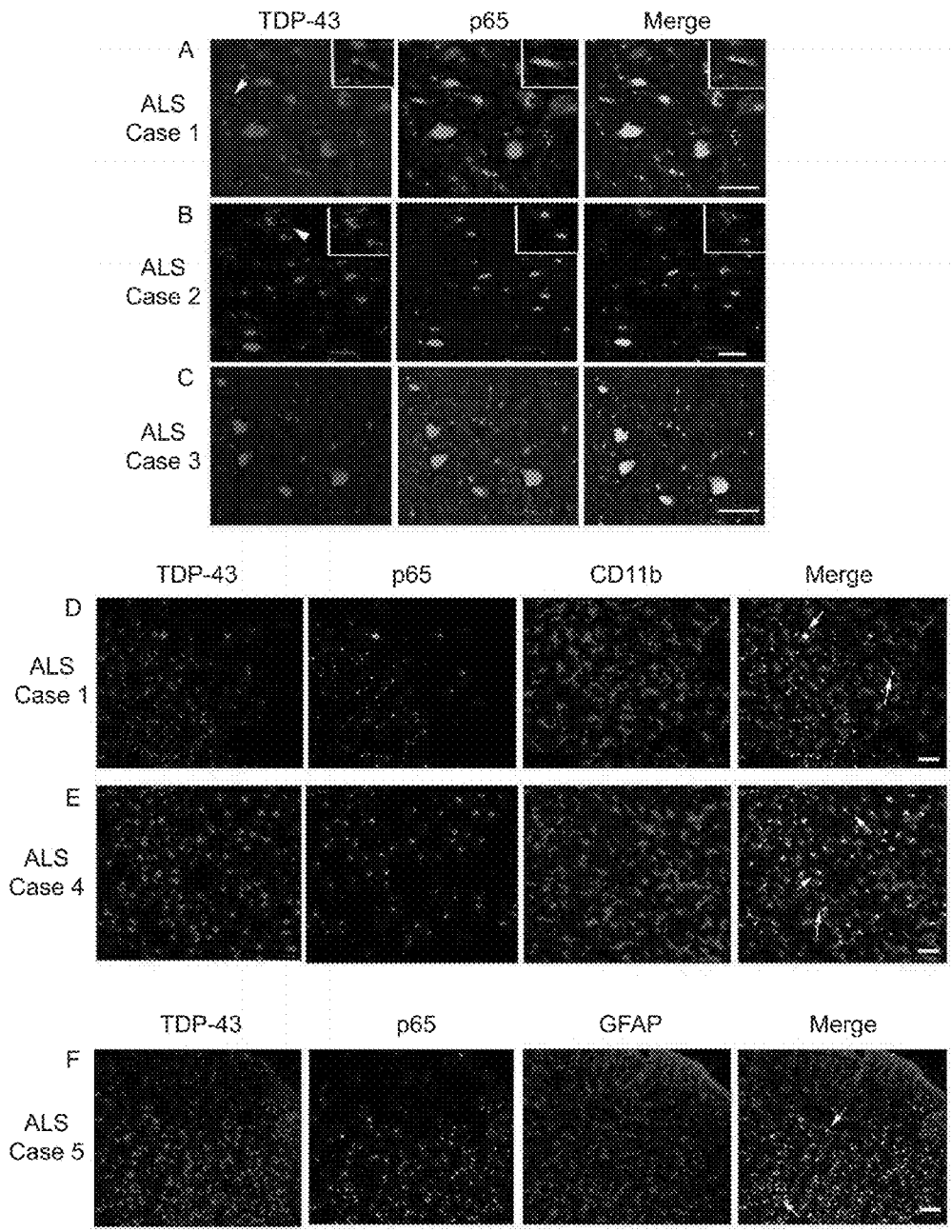
FIG. 2. TDP-43 co-localizes with p65 in neuronal and glial cells (A-C) TDP-43 and p65 double immunofluorescence was performed in 3 different ALS cases as indicated. Double immunofluorescence pictures were taken at various magnifications. The data suggests that TDP-43 co-localizes with p65 in many neuronal populations. In some neurons, where TDP-43 forms cytoplasmic aggregates, p65 is still in the nucleus (inset, arrow-heads). (D-E) A three-color immunofluorescence was performed using rabbit TDP-43, mouse p65 and rat CD11b as primary antibodies and Alexa Fluor 488 (Green), 594 (Red) and 633 (far-red, pseudo-color Blue) as secondary antibody. The triple immunofluorescence reveals that TDP-43 co-localizes with many CD11b+ microglia. Arrows indicating TDP-43, p65 co-localization in CD11b positive cells. (F) Similarly another three-color immunofluorescence was performed using rabbit TDP-43, mouse p65 and rat GFAP as primary antibodies and Alexa Fluor 488 (Green), 594 (Red) and 633 (far-red, pseudo-color Blue) as secondary antibody. The triple immunofluorescence reveals that TDP-43 co-localizes with many GFAP+ astrocytes. Arrows indicating TDP-43, p65 co-localization in GFAP positive cells. Scale bar=20 µm.
Figure 7:
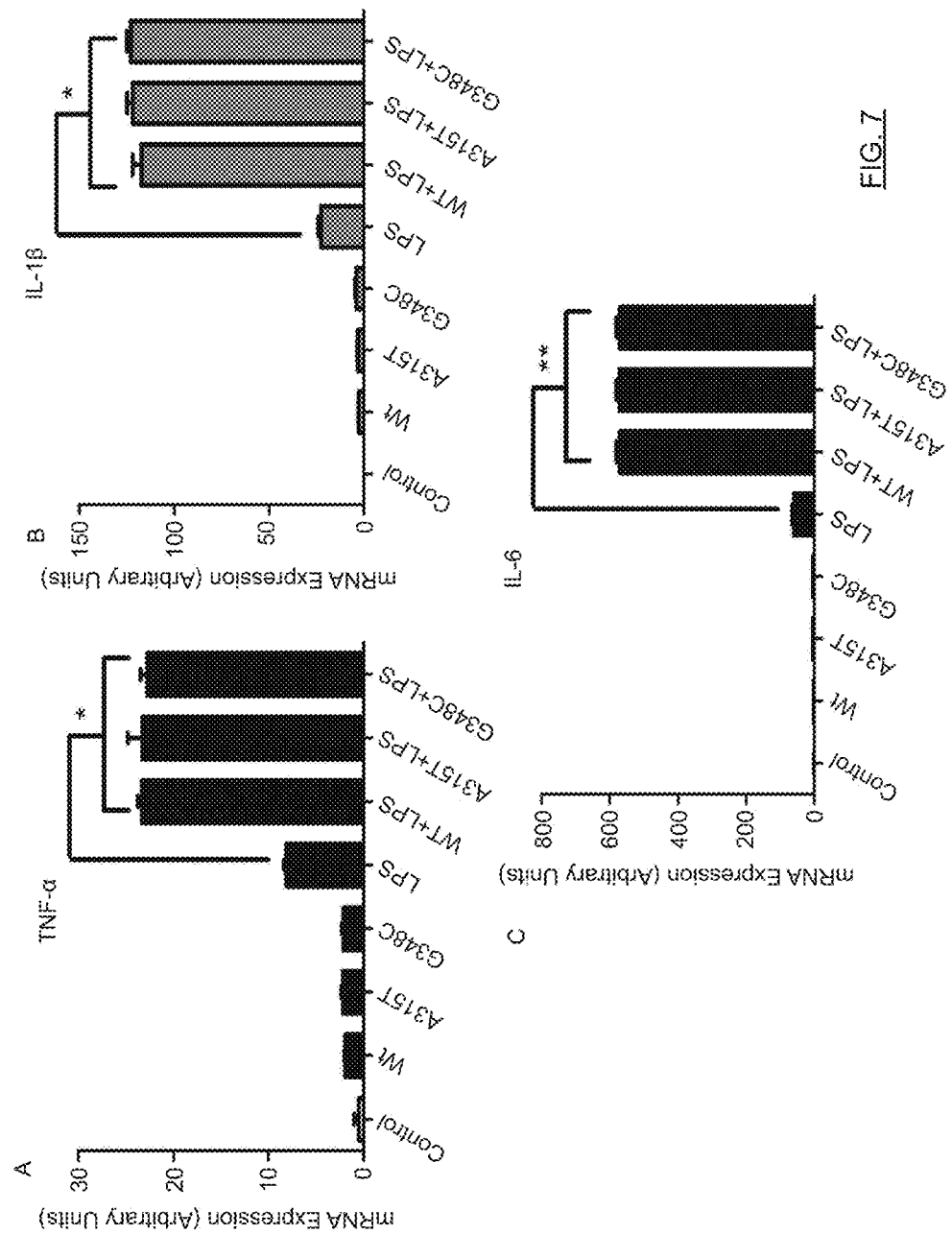
FIG. 7. Analysis of genes involved in inflammation of mouse microglial and macrophage cells overexpressing human TDP-43. Mouse microglial cells BV-2 were either transfected with pCMV-TDP43$^{wt}$, pCMV-TDP43$^{A315T}$, and pCMV-TDP43$^{G348C}$ or with empty vectors for 48 hrs. These cells were then either stimulated with LPS at a concentration of 100 ng/ml or mock-stimulated. 12 hrs after stimulation, the cells were harvested and total RNA extracted with Trizol. The total RNA samples were then subjected to real-time quantitative RT-PCR. (A) There was a 4-fold increase in mRNA levels of TNF-α following LPS stimulation of BV-2 cells compared to controls. In LPS treated cells transfected with wild-type TDP-43, there was an additional 3-fold (n=5.
Figure 7:
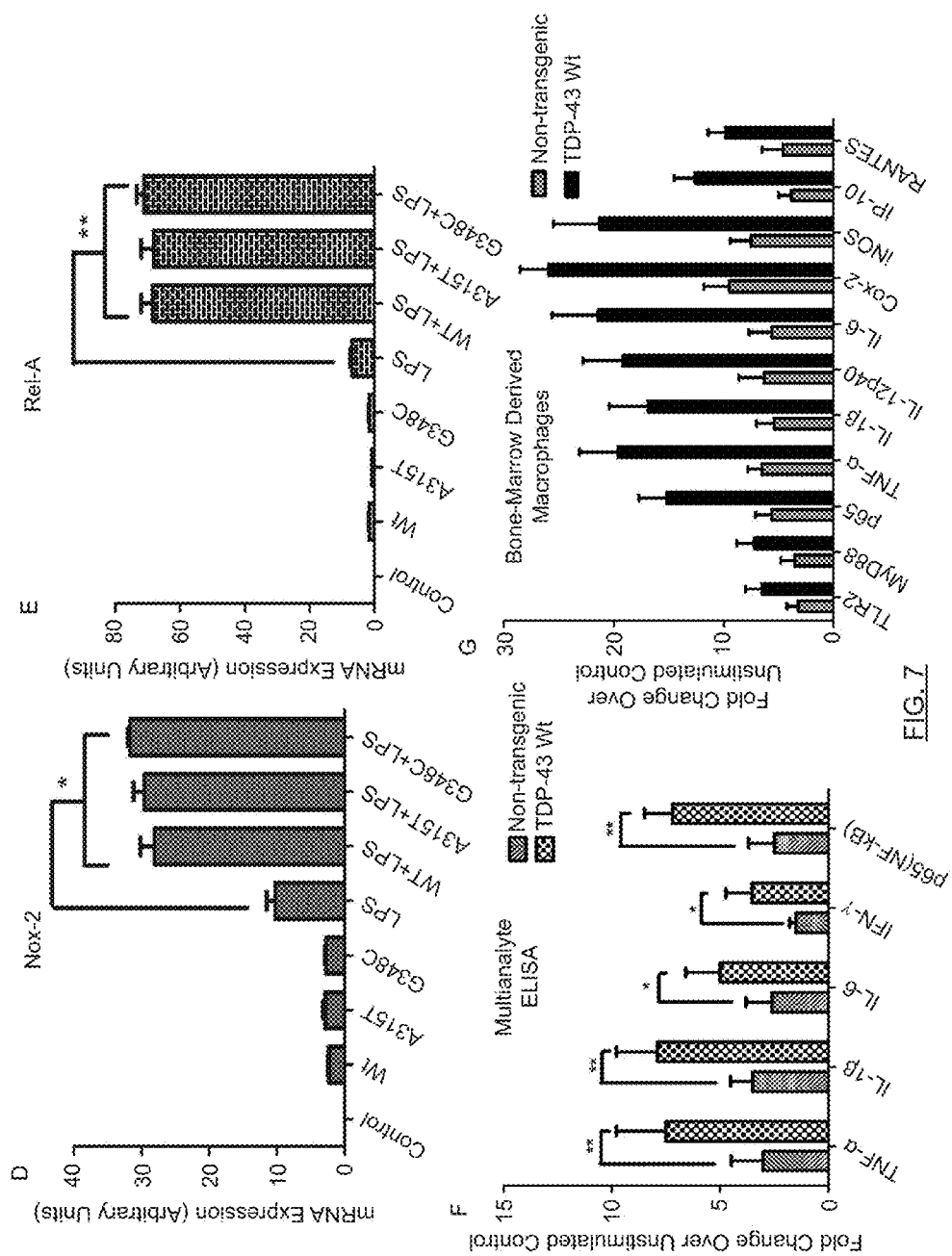

The finding that TDP-43 acts as co-activator of p65 suggests a key role for NF-κB signalling in ALS pathogenesis. This is corroborated by the abnormal 4-fold increase of p65 NF-κB mRNA in the spinal cord of human ALS (FIG. 6) and by the nuclear localization of p65 (FIG. 1L-N; FIG. 2). Remarkably, an overexpression of TDP-43 species by ~3-fold in transgenic mice, at levels similar to the human ALS situation (2.5-fold), was sufficient to cause during aging nuclear translocation of p65 NF-κB in the spinal cord (FIG. 1F-H). It should be noted that TDP-43 itself does not cause NF-kB activation (FIG. 7) and that it does not upregulate p65. It seems that a second hit is required. For example, LPS or other inducers such as pathogen-associated molecular patterns can trigger through TLR signalling p65 NF-kB nuclear localization. Cytokines such as TNF and IL-1 can also trigger p65 activation. In ALS, the second hit(s) triggering innate immune responses remain to be identified. There is recent evidence for involvement of LPS in ALS[20, 21] and of endogenous retrovirus (HEVR-K) expression[58]. Here we show that aging is associated with p65 nuclear translocation in the spinal cord of TDP-43 transgenic mice (FIG. 12) but the exact factors underlying this phenomenon remain to be defined.

There is a recent report of mutations in the gene coding for vasolin-containing protein (VCP) associated with 1-2% familial ALS cases[59]. It is well established that VCP is involved in the control of the NF-kB pathway through regulation of ubiquitin-dependent degradation of IκB-α. For instance, mutant VCP expression in mice resulted in increased TDP-43 levels and hyper-activation of NF-κB signalling[60, 61]. Moreover, some ALS-linked mutations have been discovered in the gene coding for optineurin, a protein which activates the suppressor of NF-κB[62], further supporting a convergent NF-κB-pathogenic pathway. Thus, the data presented in here as well as ALS-linked mutations in the VCP and optineurin genes[59, 61, 62] are all supporting a convergent NF-κB pathogenic pathway in ALS. The present invention shows that inhibitors of NF-κB activation are able to attenuate the vulnerability of cultured neurons overexpressing TDP-43 species to glutamate-induced or microglia-mediated toxicity. Moreover, pharmacological inhibition of NF-κB by WA treatment attenuated disease phenotypes in TDP-43 transgenic mice. From these results, it is proposed that NF-κB signalling should be considered as potential therapeutic target in ALS treatment (FIG. 16).

We report here the generation and characterization of novel transgenic mouse models of ALS-FTLD based on expression of genomic fragments encoding TDP-43 WT or mutants (A315T and G348C). The mouse models reported here carry TDP-43 transgenes under its own promoter resulting in ubiquitous and moderate expression (~3 fold) of hTDP-43 mRNA species. Most of the mouse models of TDP-43 reported previously have shown early paralysis followed by death. However, these mouse models are based on high expression levels of TDP-43 transgenes that can mask age-dependent pathogenic pathways. Mice expressing either wild-type or mutant TDP-43 (A315T and M337V) showed aggressive paralysis accompanied by increased ubiquitination (Wegorzewska et al., 2009; Stallings et al., 2010; Wils et al., 2010; Xu et al., 2010) but the lack of ubiquitinated TDP-43 positive inclusions raises concerns about their validity as models of human ALS disease. Another concern is the restricted expression of TDP-43 species with the use of Thy1.2 and Prion promoters. To better mimic the ubiquitous and moderate levels of TDP-43 occurring in the human context, it seems more appropriate to generate transgenic mice with genomic DNA fragments of TDP-43 gene including its own promoter. As in human neurodegenerative disease, our TDP-43 transgenic mice exhibited age-related phenotypic defects including impairment in contextual learning/memory and spatial learning/memory as determined by passive avoidance test and Barnes maze test. Long term memory of 10-months old TDP-43$^{G348C}$ transgenic mice was severely impaired according to Barnes maze test. The TDP-43$^{G348C}$, TDP-43$^{A315T}$ and to a lesser extent TDP-43$^{Wt}$ mice exhibited also motor deficits as depicted by significant reductions in latency in the accelerating rotarod test.

Cognitive and motor deficits in TDP-43 transgenic mice prompted us to test the underlying pathological and biochemical changes in these mice. Western blot analysis of spinal cord lysates of transgenic mice revealed ~25-kDa and ~35-kDa TDP-43 cleavage fragments which increased in levels with age. Previous studies demonstrated cytotoxicity of the ~25-kDa fragment (Zhang et al., 2009). Immunofluorescence studies with human TDP-43 specific monoclonal antibodies revealed TDP-43 cytoplasmic aggregates in the spinal cord of TDP-43$^{G348C}$, TDP-43$^{A315T}$ and to lesser extent in TDP-43$^{Wt}$ mice. The cytoplasmic TDP-43 positive inclusions were ubiquitinated. The TDP-43 positive ubiquitinated cytoplasmic inclusions along with ~25-kDa cytotoxic fragments are reminiscent of those described in studies on ALS and FTLD-U patients (Neumann et al., 2006). The co-immunoprecipitation of ubiquitin with anti-TDP-43 antibody and inversely of TDP-43 with anti-ubiquitin antibody (FIG. 18U&V) using spinal cord samples from TDP-43$^{G348C}$ mice further confirmed the association of TDP-43 with ubiquitinated protein aggregates. However, TDP-43 itself was not extensively ubiquitinated. A thorough survey of articles on TDP-43 led us to the conclusion that there is no compelling biochemical evidence in literature supporting the general belief that TDP-43 is the major poly-ubiquitinated protein in the TDP-43 positive inclusions. We could find only one blot from one ALS case in one paper (Neumann et al., 2006) that revealed a very weak detection of high molecular weight smear with anti-TDP-43 after TDP-43 immunoprecipitation. A subsequent paper by (Sanelli et al., 2007) has concluded from 3D-deconvolution imaging that TDP-43 is not in fact the major ubiquitinated target in ubiquitinated inclusions of ALS.

The TDP-43 transgenic mice described here exhibit perikaryal and axonal aggregates of intermediate filaments, another hallmark of degenerating motor neurons in ALS (Carpenter, 1968; Corbo and Hays, 1992; Migheli et al., 1993). Before the onset of behavioural changes in these mice, there is formation of peripherin aggregates in the spinal cord and brain sections of TDP-43$^{G348C}$ as well as in TDP-43$^{A315T}$ transgenic mice. These peripherin inclusions were also seen in the hippocampal region of the brain of TDP-43$^{G348C}$ mice. Normally peripherin is not expressed in brain. However, it is known that peripherin expression in the brain can be upregulated after injury or stroke (Beaulieu et al., 2002). The enhanced peripherin levels in these mice are probably due to an upregulation of IL-6, a cytokine that can trigger peripherin expression (Sterneck et al., 1996). Sustained peripherin overexpression by over 4 fold in transgenic mice was found previously to provoke progressive motor neuron degeneration during aging (Beaulieu et al., 1999). In addition, we detected in TDP-43 transgenic mice the presence of abnormal splicing variants of peripherin, such as Per 61, that can contribute to formation of IF aggregates (Robertson et al., 2003). Using Per61 specific antibodies we detected peripherin inclusions in the spinal cord sections of TDP-43$^{G348C}$ mice, but not in TDP-43$^{Wt}$ mice (FIG. 19). The occurrence of specific splicing peripherin variants has also been reported in human ALS cases (Xiao et al., 2008).

In addition we detected neurofilament protein anomalies in TDP-43$^{G348C}$ mice. Double immunofluorescence revealed the detection of neurofilament NF-H and NF-M in inclusion bodies with peripherin in the spinal cord of TDP-43$^{G348C}$ mice. Moreover, we found that neurofilament NF-L is downregulated in the spinal cord lysates of TDP-43$^{G348C}$ mice, a phenomenon which has also been observed in motor neurons of ALS cases (Wong et al., 2000). A decrease in NF-L levels may explain in part the age-related axonal atrophy detected in TDP-43 mice. Previous studies with NF-L knockout mice demonstrated that such substantial shift in calibres of large myelinated axons provokes a reduction of axon conduction velocity by ~3 fold (Kriz et al., 2000). In large animals with long peripheral nerves this would cause neurological disease. A loss of neurofilaments due to a homozygous recessive mutation in the NEFL gene was found recently to cause a severe early-onset axonal neuropathy (Yum et al., 2009).

Age-related neuroinflammation constitutes another striking feature of the TDP-43 transgenic mice. In vivo imaging of biophotonic doubly transgenic mice bearing TDP-43 and GFAP-luc transgenes showed that astrocytes are activated as early as 20 weeks in the brain of GFAP-luc/TDP-43$^{G348C}$ mice followed by activation in the spinal cord at ~30 weeks of age. The signal intensity for astrocytosis in GFAP-luc/TDP-43$^{A315T}$ and GFAP-luc/TDP-43$^{Wt}$ was less than in GFAP-luc/TDP-43$^{G348C}$ mice. It is noteworthy that the induction of astrogliosis detected in the brain and spinal cord in all three TDP-43 mouse models preceded by 6 to 8 weeks the appearance of cognitive and motor defects. This finding is in line with the recent view of an involvement of reactive astrocytes in ALS pathogenesis (Barbeito et al., 2004; Di Giorgio et al., 2007; Julien, 2007; Nagai et al., 2007; Di Giorgio et al., 2008).

In conclusion, the TDP-43 transgenic mice described here mimic several aspects of the behavioural, pathological and biochemical features of human ALS/FTLD including age-related development of motor and cognitive dysfunction, cytoplasmic TDP-43 positive ubiquitinated inclusions, intermediate filament abnormalities, axonopathy and neuroinflammation. Why there is no overt degeneration in our TDP-43 mouse models? Unlike previous TDP-43 transgenic mice, these transgenics were made with genomic fragment that contains 3' sequence autoregulating TDP-43 synthesis (Polymenidou et al., 2011). So, the TDP-43 levels remain moderate. The ubiquitous TDP-43 overexpression by about 3 folds in these mice mimics the 2.5-fold increase of TDP-43 mRNA measured in the spinal cord of human sporadic ALS by quantitative real-time PCR (our unpublished result). In human ALS cases carrying TDP-43 mutations, it takes many decades before ALS disease onset. The factors that trigger the onset are unknown but perhaps future studies with TDP-43 mouse models might provide some insights. In any case, our new TDP-43 mouse models should provide valuable tools for unraveling pathogenic pathways of ALS/FTLD and for preclinical drug testing.

The present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, the preferred methods and materials are described. The issued patents, published patent applications, and references that are cited herein are hereby incorporated by reference to the same extent as if each was specifically and individually indicated to be incorporated by reference. In the case of inconsistencies, the present disclosure will prevail.

EXAMPLES

Example 1 TDP-43 Interacts with p65 Subunit of NF-κB

Mass spectrometry analysis and co-immunoprecipitation experiments were carried out to identify proteins which interact with TDP-43 in mouse microglia (BV-2) cells after LPS stimulation, as described in Materials and Methods. Many proteins were co-immunoprecitated with TDP-43, including proteins responsible for RNA granule transport (kinesin), molecular chaperones (Hsp70) and cytoskeletal proteins (Data not shown). In addition, our analysis revealed p65 (REL-A) as a novel protein interacting with TDP-43. An interaction between TDP-43 with p65 NF-κB was confirmed by a co-immunoprecipation assay with a polyclonal antibody against TDP-43 using spinal cord extracts from transgenic mice overexpressing human TDP-43$^{wt}$ and TDP-43$^{348C}$ mutant by 3-fold (FIG. 1A). Additional co-immunoprecipitation experiments carried out using BV-2 cells which were transiently transfected with pCMV-TDP43$^{wt}$ and pCMV-p65 plasmids (FIG. 10A) clearly show that TDP-43 interacts with p65.

To further determine the significance of TDP-43 interaction with p65 in context of human ALS, TDP-43 was pulled down with the polyclonal anti-TDP43 antibody using spinal cord extracts from 9 sporadic ALS cases and 6 control subjects (FIG. 1B). In protein extracts from ALS cases, p65 NF-κB was co-immunoprecipitated with TDP-43. In contrast, no p65 was pulled down with TDP-43 using extracts of control spinal cords. To further validate, TDP-43:p65 interaction we performed reverse coimmunoprecipitation using p65 antibody to immunoprecipitate TDP-43 in human spinal cord tissues. Indeed p65 was able to co-immunoprecipitate TDP-43 in all 9 ALS cases, but not in 6 control cases (FIG. 11A). Immunofluorescence microscopy corroborated these results. In the spinal cord of sporadic ALS subjects p65 was detected predominantly in the nucleus of cells in co-localization with TDP-43 (FIG. 1L-N). On the contrary, in control spinal cord, there was absence of p65 in nucleus reflecting a lack of p65 activation (FIG. 1I-K and FIG. 2). It is remarkable that microscopy of the spinal cord from TDP-43$^{wt}$ transgenic mice revealed ALS-like immunofluorescence with active p65 that co-localized perfectly with TDP-43 in the nuclei of cells (FIG. 1F-H). To elucidate which cell types in the spinal cord of ALS cases express TDP-43 and p65, we carried out three-color immunofluorescence with CD11b as microglial specific marker and GFAP as astroglial marker. We found that TDP-43 and p65 co-localize in many microglial and astroglial cells (FIG. 2D-F). We have quantified our data and found that 20±5% of microglia and 8±3% of astrocytes have TDP-43:p65 co-localization. We also found that many of the TDP-43 p65 co-localisation was in neurons, some also in motor neurons in many ALS cases (FIG. 2A-C). In many ALS cases where TDP-43 forms aggregates in the cytoplasm, p65 is still in the nucleus (FIG. 2A-C, arrow-heads). In non-transgenic C57Bl/6 mice, the lack of p65 activation resulted in partial co-localization of TDP-43 with p65 mainly in cytoplasm (FIG. 1C-E). LPS-stimulated BV-2 cells transfected with pCMV-p65 and pCMV-TDP43$^{wt}$ had most p65 co-localized with nuclear TDP-43$^{wt}$ whereas in unstimulated cells p65 did not co-localize with nuclear TDP-43$^{wt}$ (FIG. 10B-I). While p65 was mainly cytoplasmic in 3-months old TDP-43$^{Wt}$ spinal cord, there was gradual age dependent p65 activation in 6-months and 10-months old TDP-43$^{Wt}$ spinal cord (FIG. 12).

Example 2 TDP-43 Acts as a Co-Activator of p65

A gene reporter assay was carried out to study the effect of TDP-43 on NF-κB-dependent gene expression. The effect of TDP-43 was studied on gene expression of the reporter plasmid 4κB$^{wt}$-luc by transfecting pCMV-TDP43$^{wt}$ in BV-2 cells with or without co-transfection of pCMV-p65 (FIG. 3A). When expressed alone, TDP-43 had no detectable effect on the basal transcription level of plasmid 4κB$^{wt}$-luc, suggesting that TDP-43 does not alter the basal transcription level of NF-κB. However, in co-expression with p65, TDP-43 augmented the gene expression of plasmid 4κB$^{wt}$-luc in a dose-dependent manner. pCMV-p65 (20 ng) alone activated gene expression of 4κB$^{wt}$-luc by 10-fold (FIG. 3A). However, upon co-transfection with pCMV-TDP-43$^{wt}$ (20 ng), the extent of gene activation was elevated to 22-fold (2.2-fold augmentation by the effect of TDP-43). Further increase in NF-κB-dependent gene expression was recorded as the levels of TDP-43$^{wt}$ were elevated to 50 ng (2.8-fold activation) and 100 ng (3.2-fold activation, n=4, p<0.05). When using a control luciferase reporter construct, 4κB$^{mut}$-luc, in which all four κB sites were mutated, neither the activation by pCMV-p65 nor the effect of co-transfection of pCMV-TDP43$^{wt}$ was detected.

The boosting effects of TDP-43 were not due to increased levels in p65 as shown by immunoblotting (FIG. 3B). Similarly, pCMV-TDP43$^{A315T}$ and pCMV-TDP43$^{G348C}$ augmented p65-mediated gene expression from the reporter plasmid 4κB$^{wt}$-luc (data not shown).

To further examine the effect of TDP-43 on the activation of p65, we performed p65 electrophoretic mobility shift assays (EMSA). Transfection in BV2 cells of pCMV-p65 with pCMV-TDP43$^{wt}$ or pCMV-TDP43$^{G348C}$ and LPS treatment was followed by extraction of nuclear proteins. Subsequently the interaction between p65 in the protein extract and DNA probe was investigated using EMSA kit from Panomics (Redwood City, Calif., USA) following the manufacturer's instructions. TDP-43 increased the binding of p65 to the NF-κB DNA probe in a dose-dependent manner. LPS alone induced the binding of p65 to the DNA probe by about 2-fold as compared to control (FIG. 3C). The co-transfection of TDP-43$^{wt}$ (50 ng and 100 ng) or of TDP-43$^{G348C}$ (100 ng) resulted in a significant dose-dependent increase in the DNA binding of p65. The specificity of the gel shift assay was assessed by adding a cold probe. TDP-43 alone does not bind to p65 EMSA probes (FIG. 11B). Moreover, adding an anti-HA antibody which recognizes the transfected TDP-43 or an anti-p65 antibody caused supershifts of bands in the p65 EMSA (FIG. 3D).

Example 3 P65 Interacts with the N-Terminal and RRM-1 Domains of TDP-43

To determine which domains of TDP-43 interacts with p65, we constructed a series of deletion mutants of various TDP-43 domains. Various pCMV-HA tagged deletion mutants like TDP-43$^{ΔN}$ (1-105AAs), TDP-43$^{ΔRRM-1}$ (106-176AAs), TDP-43$^{ΔRRM-2}$ (191-262AAs) and TDP-43$^{ΔC}$ (274-414AAs) were transfected in BV-2 cells with pCMV-p65 (FIG. 4A). TDP-43$^{ΔRRM-1}$ co-immunoprecipitated p65 partially whereas TDP-43$^{ΔRRM-2}$ and TDP-43$^{ΔC}$ interacted well with p65, suggesting that RRM-1 is important, but RRM-2 and C-terminal domains are dispensable for interaction with p65. Following transfection we found that TDP-43$^{ΔN}$ had much reduced interaction with p65 (FIG. 4B), thereby suggesting that N-terminal domain of TDP-43 is essential for the interaction of TDP-43 with p65. Since the nuclear localization signal (NLS) is in the N-terminal, the reduced interaction of TDP-43$^{ΔN}$ to p65 could have been the result of a mislocalization of TDP-43$^{ΔN}$. To address this issue and to further define the interacting domain, we constructed series of N-terminal and RRM-1 deletion mutants—TDP-43$^{ΔNR1-81}$ (98-176AAs), TDP-43$^{ΔNR1-50}$ (51-81 and 98-176 AAs) and TDP-43$^{ΔNR1-30}$ (31-81 and 98-176 AAs) with the NLS signal attached so that the mutant proteins are able to be directed to the nucleus. Co-immunoprecipitation with these constructs suggested that even though TDP-43$^{ΔNR1-30}$ is in the nucleus, it cannot effectively interact with p65, TDP-43$^{ΔNR1-81}$ and TDP-43$^{ΔNR1-50}$ whereas can interact with p65 (FIG. 4B). These results indicate that TDP-43 interacts with p65 through its N-terminal domain (31-81 and 98-106 AAs) and RRM-1 (107-176 AAs) domain.

To assess the effect of these deletion mutants on the activation of NF-κB gene, we used the gene reporter assay. Various deletion mutants of TDP-43 were co-transfected along with 4κB$^{wt}$-luc or 4κB$^{mut}$-luc. When compared to full length TDP-43$^{wt}$, TDP-43$^{ΔN}$ had reduced effect (2-fold, n=3, p<0.05) on the gene activation. TDP-43$^{ΔRRM-1}$ also exhibited attenuation of gene activation but to lesser extent than TDP-43$^{ΔN}$ (FIG. 4C). In contrast, TDP-43$^{ΔRRM-2}$ and TDP-43$^{ΔC}$ deletion mutants had effects similar to full length TDP-43$^{wt}$. As expected, because TDP-43$^{ΔNR1-30}$ does not effectively interact with p65, the level of NF-κB activation detected by the 4κB$^{wt}$-luc reporter assay was extremely low, 6-fold lower than full-length TDP-43$^{wt}$ (n=3, p<0.001) (FIG. 4C). Transfection of a control luciferase reporter construct, 4κB$^{mut}$-luc, in which all four κB sites were mutated, had no effect on the basal-level activation of p65. To determine, if the interaction between TDP-43 and p65 is a protein-protein interaction, we performed immunoprecipitation experiments by adding either proteinase K, RNase A or DNase 1 (FIG. 4D). Addition of proteinase K abolished TDP-43-p65 interaction, whereas RNase A or DNase 1 had no effect, suggesting that the interaction is not DNA/RNA dependent.

Example 4 TDP-43 siRNA Inhibits Activation of NF-κB

If correct that TDP-43 acts as a co-activator of p65, then reducing the levels of TDP-43 should attenuate p65 activation. To reduce the expression levels of TDP-43, microglial BV-2 cells were transfected with either TDP-43 siRNA or scrambled siRNA together with 4κB$^{wt}$-luc vectors. 72 hrs after transfection some of the cells were either stimulated with LPS (100 ng/ml) or mock stimulated for 12 hrs. As shown in (FIG. 5A), TDP-43 siRNA reduced the endogenous mouse TDP-43 levels significantly as compared to scrambled siRNA transfected cells in two different experiments. To examine the effect of reducing TDP-43 levels on NF-κB activation, BV-2 cells were transfected with pCMV-p65 and 4κB$^{wt}$-luc vectors. TDP-43 siRNA decreased activation of NF-κB reporter gene in transfected cells. The decrease in NF-κB activation was about 3-fold for 5 ng pCMV-p65 (n=4, $p<0.01$) and about 2.5-fold for 10 and 20 ng pCMV-p65 (n=4, $p<0.05$) and 2-fold for 50 ng pCMV-p65 (n=4, $p<0.05$) as compared to scrambled siRNA transfected cells (FIG. 5B). To examine the physiological significance of TDP-43 inhibition by siRNA, we transfected BV-2 cells with ICAM1-luc vector together with TDP-43 siRNA or scrambled siRNA. 72 hrs after transfection, cells were stimulated with varying concentrations of TNF-α. When stimulated at 0.5 ng/ml of TNF-α, TDP-43 siRNA transfected cells exhibited a 2-fold decrease in ICAM-1 luciferase activity (n=4, $p<0.05$) as compared to cells transfected with scrambled siRNA. Similarly, TDP-43 siRNA transfected BV-2 cells exhibited at 1.0 ng/ml and 1.5 ng/ml TNF-α concentrations decrease of 2.5-fold (n=4, $p<0.01$) and 2-fold (n=4, $p<0.05$) in ICAM-1 luciferase activity, respectively (FIG. 5C). We also tested the effect of TDP-43 siRNA transfected in bone-marrow derived macrophages (BMMs) from normal mice. We compared the level of innate immunity activation when stimulated with LPS. BMMs transfected with TDP-43 siRNA had reduced levels of TLR2 mRNA (1.5-fold, $p<0.05$), p65 (3-fold, $p<0.01$), TNF-α (3-fold, $p<0.01$), IL-1β (2-fold, $p<0.05$), IP-10 (2-fold, $p<0.05$), IL-6 (2.5-fold, $p<0.01$) and Cox-2 (2-fold, $p<0.05$) as compared to scrambled siRNA transfected BMMs (FIG. 5D).

Example 5 TDP-43 and P65 mRNA Levels are Upregulated in the Spinal Cord of Sporadic ALS Patients The findings that TDP-43 can interact with p65 and that TDP-43 overexpression in transgenic mice was sufficient to provoke abnormal nuclear co-localization of p65 as observed in sporadic ALS (FIG. 1 L-N), prompted us to compare the levels of mRNA coding for TDP-43 and p65 NF-κB in spinal cord samples from sporadic ALS cases and control individuals. Real-time RT-PCR data revealed that the levels of TDP-43 mRNA in the spinal cord of sporadic ALS cases (n=16) were upregulated by about 2.5-fold ($p<0.01$) compared to controls (n=6) (FIG. 6A). It is also noteworthy that the levels of p65 NF-κB mRNA were upregulated by about 4-fold ($p<0.001$) in ALS cases as compared to controls. Since TDP-43 forms many bands in western blot analysis, we quantified the total level of TDP-43 protein using sandwich ELISA as described in the materials and methods. The ELISA results suggest that TDP-43 protein levels are in fact upregulated in total spinal cord protein extracts of ALS cases (n=16) by 1.8-fold (253.2±10.95 ng/ml) as compared to control cases (140.8±6.8 ng/ml, n=6) (FIG. 6B). For human p65 ELISA, we used an ELISA kit from SABioscience, Qiagen. The levels of p65 were also upregulated in total spinal cord extracts of ALS cases (n=16) by 3.8-fold (242.8±9.5 ng/ml) as compared to control cases (63.33±2.8 ng/ml, n=6) (FIG. 6C).

Example 6 TDP-43 Overexpression in Microglia Causes Hyperactive Inflammatory Responses to LPS Since NF-κB is involved in pro-inflammatory and innate immunity response, we tested the effects of increasing TDP-43 mRNA expression in BV-2 cells. Because LPS is a strong pro-inflammatory stimulator[33], we used it to determine the differences in levels of pro-inflammatory cytokines produced by TDP-43-transfected or mock-transfected BV-2 cells. BV-2 cells were transiently transfected either with pCMV-TDP43$^{wt}$, pCMV-TDP43$^{A315T}$, pCMV-TDP43$^{G348C}$ or empty vector. 48 hrs after transfection and 12 hrs after LPS challenge (100 ng/ml), RNA extracted from various samples were subjected to real-time quantitative RT-PCR to determine the mRNA levels of various pro-inflammatory genes. As expected, there was a 4-fold increase in mRNA levels of TNF-α following LPS stimulation of BV-2 cells compared to controls (FIG. 7A). However in LPS treated cells transfected with wild-type TDP-43, there was an additional 3-fold (n=5, $p<0.05$) increase in TNF-α levels. TDP-43 harboring the A315T and G348C mutations had similar effects on boosting the levels of TNF-α upon LPS stimulation. Similarly, in response to LPS, the extra levels of TDP-43 species in transfected microglial cells caused a significant 5-fold increase (n=5, $p<0.001$) in the mRNA levels of IL-1β (FIG. 7B) and 9-fold increase in mRNA levels of IL-6 (FIG. 7C, n=5, $p<0.001$) as compared to LPS-treated mock-transfected cells. The levels of NADPH oxidase 2 (Nox-2 gene) was increased by about 2.8-fold (FIG. 7D, n=5, $p<0.05$) in LPS-challenged TDP-43 transfected cells as compared to LPS treated mock-transfected cells. Remarkably, overexpression of TDP-43 species resulted in 10-fold (n=5, $p<0.001$) increase in levels of p65 (RELA) mRNA in LPS-treated transfected cells as compared to LPS-treated mock-transfected cells (FIG. 7E). Note that, in absence of LPS stimulation, microglial cells transfected with TDP-43 species (both wild-type and mutants) exhibited no significant differences in levels of TNF-α, IL-1β, Nox-2 and NF-κB when compared to mock-transfected controls.

To further evaluate the effect of LPS stimulation in TDP-43 overexpressing microglia, we prepared primary microglial cultures from C57Bl/6 mice and from transgenic mice overexpressing by 3-fold TDP-43$^{wt}$ (FIG. 9A-D). Primary microglial cells were challenged with LPS at a concentration of 100 ng/ml of media. 12 hrs after LPS challenge, cells were harvested and total protein extracted and used for multi-analyte ELISA. LPS-treated TDP-43$^{wt}$ transgenic microglia had significantly higher levels of TNF-α (2.5-fold, $p<0.01$), IL-1β (2.3-fold, $p<0.01$), IL-6 (2-fold, $p<0.05$) and IFN-γ (2-fold, $p<0.05$) as compared to LPS-treated microglia from C57Bl/6 non-transgenic mice (FIG. 7F). However, in absence of LPS stimulation, no significant differences in cytokines levels were detected between microglia from TDP-43$^{wt}$ transgenic mice and from non-transgenic mice (Data not shown). The p65 level was significantly higher (3-fold; $p<0.01$) in LPS-treated TDP-43$^{wt}$ microglia as compared to non-transgenic microglia (FIG. 7F). To further evaluate the innate immune response in TDP-43$^{wt}$ transgenic mice, we isolated bone-marrow derived macrophages (BMM) from TDP-43$^{wt}$ transgenic mice and from C57Bl/6 non-transgenic mice. In LPS-stimulated TDP-43$^{wt}$ macrophages there was an increase of 2-fold ($p<0.05$) in TLR2 mRNA levels, 2-fold ($p<0.05$) in MyD88 levels, 2.8-fold ($p<0.01$) in p65 (RELA, $p<0.01$) levels as compared to LPS stimulated control (non-transgenic) macrophages (FIG. 7G). We also found in LPS-stimulated TDP-43$^{wt}$ macrophages that there was an increase of 3-fold ($p<0.01$) in TNF-α, IL-1β and IL-12p40 levels, 3.8-fold ($p<0.01$) in IL-6 levels, 2.7-fold ($p<0.01$) in Cox-2 and iNOS levels, 3-fold in IP-10 levels and 2-fold in RANTES mRNA levels as compared to LPS stimulated control (non-transgenic) macrophages (FIG. 7G).

Example 7 TDP-43 Upregulation Increases Microglia-Mediated Neurotoxicity

We then examined the effect of TDP-43 overexpression on toxicity of microglia towards neuronal cells. This was done with the use of primary microglia and of cortical neurons derived from transgenic mice overexpressing TDP-43 species (TDP-43$^{wt}$, TDP-43$^{A315T}$ or TDP-43$^{G348C}$) and C57Bl/6 non-transgenic mice. Primary cortical neurons were cultured for 12 hrs in conditioned media from LPS-stimulated microglial cells. All conditioned media from LPS-challenged microglia increased the death of cortical neurons in culture (FIG. 13A). The media from LPS-stimulated non-transgenic microglial cells increased the neuronal death of non-transgenic mice by 3.5-fold ($p<0.01$). However, there were marked increases of neuronal death caused by conditioned media from LPS challenged microglia (of same genotype) overexpressing TDP-43 species: 5.5-fold ($p<0.001$) for TDP-43$^{wt}$, 6.5-fold ($p<0.001$) for TDP-43$^{A315T}$ and 7.5-fold ($p<0.001$) for TDP-43$^{G348C}$. The increased neurotoxicity of the conditioned media was associated with increased ROS and NO production. The ROS production, as determined by H2DCFDA fluorescence, was significantly higher in conditioned media challenged neurons from TDP-43$^{wt}$ (1.5-fold, $p<0.05$), TDP-43$^{A315T}$ (1.8-fold, $p<0.05$) or TDP-43$^{G348C}$ (2-fold, $p<0.05$) as compared individually to conditioned media challenged non-transgenic control neurons (FIG. 13B). Similarly, the nitrite (NO) production was significantly higher in TDP-43$^{wt}$ (1.5-fold, $p<0.05$), TDP-43$^{A315T}$ (2.3-fold, $p<0.05$) or TDP-43$^{G348C}$ (3-fold, $p<0.01$) as compared individually to non-transgenic control (FIG. 13C).

Example 8 Inhibition of NF-κB Activation Reduces Vulnerability of TDP-43 Overexpressing Neurons to Toxic Injury The experiments above revealed also that the presence of TDP-43 transgenes in cortical neurons increased their vulnerability to microglia-mediated toxicity. NF-αB is known to modulate p53-p38MAPK dependent apoptosis in neurons, when treated with DNA damage inducing chemicals like camptothecin[34], glutamate excitotoxicity[35] or general bystander mediated killing of neurons by microglia[14]. To assess the potential contribution of NF-κB to the death of TDP-43 overexpressing neurons exposed to toxic injury, we prepared cultures of primary cortical neurons and microglia from transgenic mice overexpressing TDP-43$^{wt}$ or TDP-43 mutants. Cortical neurons were exposed to 10 μM glutamate for 15 min, with or without 1 μM withaferin A (WA), a known inhibitor of NF-κB[36]. The LDH cytotoxicity was determined 24 hrs later (FIG. 14A). We found that neurons overexpressing TDP-43 species were more vulnerable than non-transgenic neurons to glutamate cytotoxicity and that inhibition of NF-κB by WA resulted in marked decrease in cell death: TDP-43$^{wt}$ (2-fold, $p<0.01$), TDP-43$^{A315T}$ (3-fold, $p<0.01$) and TDP-43$^{G348C}$ (3-fold, $p<0.01$). The addition of WA inhibited NF-κB, as detected by reduced levels of phospho-p65$^{Ser536}$ (FIG. 14B). We then incubated cortical neurons with the conditioned media from primary microglial culture, which were challenged with LPS at a concentration of 50 ng/ml of media. Treatment of neuronal cultures with WA resulted in substantial decrease in microglia-mediated death of neurons overexpressing TDP-43$^{wt}$ (2-fold, $p<0.01$), TDP-43$^{A315T}$ (3-fold, $p<0.01$) or TDP-43$^{G348C}$ (3-fold, $p<0.01$). As WA might exert multiple pharmacological actions, we tested a more specific molecular approach for inhibiting NF-κB. Since, activation of NF-κB requires its dissociation from the inhibitory molecule, IκB, we expressed a stable mutant super-repressive form of IκB-α (Ser 32/Ser36-to-alanine mutant; IκB$^{SR}$) and evaluated its effects on neuronal death. Cultured cortical neurons from TDP-43 transgenic and non-transgenic mice were transfected with a plasmid construct, expressing IκB$^{SR}$, and exposed to either 10 μM glutamate for 30 min or incubated in conditioned media from LPS-stimulated microglia of same genotype. Similar to WA treatment, we found that IκB$^{SR}$ inhibited NF-κB activation and it attenuated the glutamate-induced or microglia-mediated death of neurons overexpressing TDP-43$^{wt}$ (1.3-fold, $p<0.01$), TDP-43$^{A315T}$ (1.5-fold, $p<0.01$) and TDP-43$^{G348C}$ (2-fold, $p<0.01$) (FIG. 14C-D).

Example 9 NF-κB Inhibition by Withaferin a Treatment Reduces Inflammation and Ameliorates Motor Impairment of TDP-43 Transgenic Mice To study the in vivo effect of NF-κB inhibition on disease progression, we injected TDP-43$^{wt}$; GFAP-luc double transgenic mice with 3 mg/kg body weight of WA twice a week for 10-weeks starting at 30-weeks. The pharmacokinetic parameters of withaferin A has been published recently[37] and we have determined here that this compound passes the blood-brain barrier (FIG. 15). We used TDP-43$^{wt}$; GFAP-luc double transgenic mice because the reporter luciferase (luc) allowed the longitudinal and non-invasive biophotonic imaging with CCD camera of the GFAP promoter activity which is a target of activated NF-κB. To analyse the spatial and temporal dynamics of astrocytes activation/GFAP induction in TDP-43 mouse model, we performed series of live imaging experiments. These live imaging experiments revealed that treatment of TDP-43$^{wt}$; GFAP-luc mice with WA caused progressive reduction in GFAP-luc expression in the spinal (FIG. 8A-B) compared to untreated TDP-43$^{wt}$ mice which continued to exhibit high GFAP-luc expression. The downregulation of GFAP promoter activity was further confirmed in these mice using GFAP immunofluorescence of spinal cord sections of TDP-43$^{Wt}$ mice (both drug-treated and untreated) (FIG. 8F). This downregulation of GFAP in withaferin-treated mice was actually caused by reduced amount of active p65 in the nucleus of cells as indicated by p65 EMSA (FIG. 8D). Down-regulation of GFAP along with reduction in active p65 levels in withaferin treated mice prompted us to analyse behavioural changes in these mice.

Analysis of motor behaviour using accelerating rotarod showed that withaferin-treated TDP-43$^{wt}$ mice had significantly better motor performance compared to untreated TDP-43$^{wt}$ mice as indicated by improved rotarod testing times (FIG. 8C). We performed peripherin immunofluorescence and found reduction of peripherin aggregates in withaferin treated TDP-43Wt mice (FIG. 8E). Peripherin levels were also reduced in withaferin treated TDP-43$^{Wt}$ mice as seen by immunoblot (FIG. 14E). Double immunofluorescence of activated microglial marker Mac-2 and cyclo-oxygenase-2 (Cox-2) shows a marked reduction in activated microglia in withaferin treated TDP-43$^{Wt}$ mice (FIG. 8E and FIG. 14F). The withaferin treated mice also had 40% reduction in the number of partially denervated neuromuscular junction (NMJ) (FIGS. 8E&G).

Example 10 Generation of Transgenic Mice Carrying Genomic TDP-43 Fragments

We generated three transgenic mouse models using genomic DNA fragments coding for either TDP-43$^{Wt}$, TDP-43$^{A315T}$ or TDP-43$^{G348C}$ carrying mutations linked to human FALS (Kabashi et al., 2008). The transgenic mice (Wt, A315T and G348C) were generated by injection into one-cell embryos of DNA fragments, subcloned from TARDBP BAC using the endogenous ~4 kB promoter. The A315T and G348C mutations were inserted using site directed mutagenesis (FIG. 17A). Founder TDP-43 transgenic mice were identified by the presence of the 1.8-kb EcoRV fragment on the Southern blot. RT-PCR analysis of the spinal cord lysates of TDP-43$^{Wt}$, TDP-43$^{A315T}$ and TDP-43$^{G348C}$ mice reveal bands corresponding to human TDP-43. As shown by immunoblot analysis the human TDP-43 transgenes (Wt and mutants) were expressed in all the tissues examined (FIG. 17B). Real-time RT-PCR showed that the mRNA expression of hTDP-43 in the spinal cord was elevated by ~3-fold in 3-months old TDP-43$^{Wt}$, TDP-43$^{A315T}$ and TDP-43$^{G348C}$ transgenic mice as compared to endogenous mouse TDP-43 (FIG. 17C). Whereas expression of human TDP-43 mRNA transcripts remained constant with age, the levels of endogenous mouse TDP-43 mRNA transcripts were decreased significantly in 10-months old transgenic mice (TDP-43$^{Wt}$, TDP-43$^{A315T}$ and TDP-43$^{G348C}$) as compared to 3-months old mice (*p<0.01). This is consistent with a TDP-43 autoregulation through TDP-43 binding and splicing-dependent RNA degradation as described as previously (Polymenidou et al., 2011). We next examined whether in our transgenic models we can detect pathological cytosolic TDP-43, characteristics of ALS. The immunohistochemical staining with anti-human TDP-43 antibodies of spinal cord sections from 10-months old transgenic mice revealed a cytoplasmic accumulation of TDP-43 in TDP-43$^{G348C}$ mice and to a lower extent in TDP-43$^{A315T}$ mice (FIG. 17D-G). In contrast, the TDP-43 localization remained mostly nuclear in TDP-43$^{Wt}$ and non-transgenic mice.

Example 11 Over-Expression of WT and Mutant TDP-43 is Associated with the Formation of Cytosolic Aggregates Biochemically, ALS and FTLD-U cases are characterized by 25 kDa C-terminal deposits which might contribute to pathogenesis (Cairns et al., 2007). Similar to ALS cases, TDP-43$^{G348C}$ and TDP-43$^{A315T}$ mice had ~25 kDa fragments in the spinal cord (FIG. 18A-B). This ~25 kDa fragment was more prominent at 10 months of age (FIG. 18B) than at 3 months of age (FIG. 18A). Blots probed with human TDP-43 specific monoclonal antibody reveal increased cytotoxic ~25-kDa TDP-43 fragment in the brain and spinal cord lysates of TDP-43$^{G348C}$ and TDP-43$^{A315T}$ mice at 10-months age as compared to 3-months old mice. Using immunofluorescence and monoclonal TDP-43 antibody, we detected the presence of cytoplasmic TDP-43 aggregates in TDP-43$^{G348C}$ mice (FIG. 18H) and TDP-43$^{A315T}$ (FIG. 18G) mice at around 10-months of age, but not in TDP-43$^{Wt}$ mice (FIG. 18F). Cytoplasmic localization as well as aggregates of TDP-43 were age dependent as they were absent in the spinal cord sections of 3-month old mice (FIG. 18C-E). In order to determine if the TDP-43 aggregates were ubiquitinated, we performed double immunofluorescence with TDP-43 and anti-ubiquitin antibodies. We found that ubiquitin specifically co-localized with cytoplasmic TDP-43 aggregates in the spinal cord (FIG. 18L-N), hippocampal (FIG. 22O-Q) and cortical sections (FIG. 18R-T) of 10-months old TDP-43$^{G348C}$ mice, but not in the spinal cord sections of 3-months old (FIG. 18I-K) TDP-43$^{G348C}$ mice. Ubiquitination of TDP-43 positive inclusions were further confirmed by the co-immunoprecipitation of ubiquitin (poly-ubiquitin) with hTDP-43. This immunoprecipitation experiment clearly demonstrates that proteins associated with TDP-43 inclusions especially in 10-months old TDP-43$^{G348C}$ and TDP-43$^{A315T}$ mice are massively ubiquitinated (FIG. 18U). However, probing the blot with anti-human TDP-43 monoclonal antibody (FIG. 18U) or with polyclonal antiTDP-43 (data not shown) did not reveal high molecular weight forms of TDP-43 suggesting that TDP-43 itself was not ubiquitinated. To further address this question, we have carried out immunoprecipitation of spinal cord extracts with anti-ubiquitin and probed the blot with anti-TDP-43 monoclonal antibody (FIG. 18U). As expected, TDP-43 was co-immunoprecipitated with anti-ubiquitin. However, only small amount of high molecular weight forms of TDP-43 (i.e. poly-ubiquitinated) could be detected (FIG. 18V). This result is consistent with a report that TDP-43 is not in fact the major ubiquitinated target in ubiquitinated inclusions of ALS (Sanelli et al., 2007).

Example 12 Peripherin Overexpression and Neurofilament Disorganization in TDP-43 Transgenic Mice A pathological hallmark of both sporadic and familial ALS is the presence of abnormal accumulations of neurofilament and peripherin proteins in motor neurons (Carpenter, 1968; Corbo and Hays, 1992; Migheli et al., 1993). Here, we investigated whether such cytoskeletal abnormalities appear in the large motor neurons of TDP-43 transgenic mice. Immunofluorescence analysis of the spinal cord sections by anti-peripherin polyclonal antibody, revealed presence of peripherin aggregates in large motor neurons of TDP-143$^{G348C}$, TDP-43$^{A315T}$ and to a lesser extent in TDP-43$^{Wt}$ mice at 10-months of age as compared to 3-months old mice (FIG. 19A-E). Further analysis revealed that peripherin aggregates were also present in the brain. The aggregates in TDP-43$^{G348C}$ and to a lesser extent in TDP-43$^{A315T}$ and TDP-43$^{Wt}$ mice were localized in the hippocampus (FIG. 19F-J) and in the cortex (FIG. 19K-O). Western blot analysis of the brain lysates of transgenic mice using polyclonal antibody against peripherin revealed abnormal splicing variants of peripherin in TDP-43$^{G348C}$ and TDP-43$^{A315T}$ transgenic mice, including a toxic Per61 fragment (FIG. 19P) along with other fragments like Per56 and the normal Per58. The use of anti-peripherin monoclonal antibody revealed overexpression of the peripherin ~58 kDa fragment in TDP-43$^{G348C}$, TDP-43$^{A315T}$ and to a lower extent in TDP-43$^{Wt}$ mice compared to non-transgenic mice.

Earlier reports have shown that Per61 is neurotoxic and is present in spinal cords of ALS patients (Robertson et al., 2003). We then determined the mRNA expression levels in the spinal cord extracts of various peripherin transcripts (Per61, Per58 and Per56) using real-time PCR. Though the levels of Per58 and Per56 are not significantly different between various transgenic mice, the levels of Per61 are significantly upregulated (~2.5 fold, p<0.01) in TDP-43$^{G348C}$ mice compared to TDP-43$^{Wt}$ mice (FIG. 19Q). Per61 was also upregulated in TDP-43$^{A315T}$ mice (~1.5 fold) compared to TDP-43$^{Wt}$ mice. Antibody specifically recognizing Per61 was used to detect Per61 in the spinal cord sections of TDP-43$^{G348C}$ mice (FIG. 19S) and in TDP-43Wt mice (FIG. 19R). As expected Per61 antibody stained Per61 aggregates in the axons and cell bodies in human ALS spinal cord sections (FIG. 19U) but not control spinal cord tissues (FIG. 19T).

The TDP-43 transgenic mice also exhibit altered levels of peripherin and neurofilament protein expression. As shown in FIG. 20A, western blotting revealed that NF-H is down-regulated by about 1.5-fold and NF-L by about 2-fold in the spinal cord extracts of 10 months old TDP-43$^{G348C}$ mice as compared to non-transgenic mice (FIG. 20A). The levels of NF-M on the other hand were not significantly altered in any of the transgenic mice. We determined neurofilament levels in the spinal cords of 10-months old transgenic and non-transgenic mice using ELISA technique. Usual ELISA methods are not suitable for the quantitative measurement of neurofilament proteins because of their insolubility. However, neurofilament proteins are dissolved in urea at high concentration. Standard curves of NF-L, NF-M and NF-H dissolved in various concentrations of urea diluted with the dilution buffer were prepared as described elsewhere (Lu et al., 2011). A suitable concentration of urea for detection was estimated to be around 0.3 mol/L, because the sensitivity was higher in 0.3 mol/L urea than in the other concentrations examined. Analysis of ELISA revealed that NF-L levels are significantly reduced in 10-months old TDP-43$^{G348C}$ mice as compared to age-matched non-transgenic controls (**p<0.001). 10-months old spinal cord samples were fractionated in detergent soluble and insoluble fractions. Though most of the neurofilament proteins were in detergent insoluble fraction, peripherin levels could be detected in both soluble and insoluble fractions. We also determined the NF-H, NF-M and NF-L levels in the sciatic nerve of 3 and 10-months old transgenic mice. We observed a slight decrease in NF-L levels in 3-months old TDP-43$^{G348C}$ mice as compared to age-matched TDP-43$^{Wt}$ and TDP-43$^{A315T}$ mice, which had levels similar to non-transgenic mice (FIG. 20B). At 10-months of age, TDP-43$^{G348C}$ mice had about 50% reduction in NF-L levels in the sciatic nerve (FIG. 20B) as compared to TDP-43$^{Wt}$ mice. We then used double immunofluorescence techniques to determine which neurofilament forms part of the aggregates with peripherin in TDP-43$^{G348C}$ spinal cord sections. We found that NF-H clearly forms part of the aggregates (FIG. 20C-E), followed by NF-M to a lesser extent (FIG. 20F-H) and NF-L (FIG. 20I-K) does not form part of the aggregates. TDP-43 aggregates co-localize partially with NF-H and NF-M, but not with NF-L.

Example 13 Smaller Calibre of Peripheral Axons in TDP-43 Transgenic Mice

Our previous work has demonstrated that over-expression of the wild type peripherin, especially in context of NF-L loss, leads to a late onset motor neurons disease and axonal degeneration (Beaulieu et al., 1999). To investigate whether similar pathology was associated with peripherin induction in TDP-43 transgenic mice, we analysed at different time points the number of axons, the distribution of axonal calibre and their morphology. Axonal counts of the L5 ventral root from TDP-43 transgenic mice at 10-months age failed to reveal any significant differences in the number of motor axons (FIG. 21A-E). Normal mice exhibit a bimodal distribution of axonal calibre with peaks at ~2 µm and ~7 µm in diameter (FIG. 21F). In contrast, a skewed bimodal distribution is observed in TDP-43 transgenic mice. There was a 10% increase (an increase of 100 axons, p<0.001) in the number of motor axons with 1- to 3-µm calibre and a 12% decrease (a decrease of 120 axons) in the number of motor axons with 6- to 9-µm calibre in 10-months old TDP-43$^{G348C}$ mice compared to non-transgenic mice. (FIG. 21F). There was similar 7% increase (an increase of 70 axons, p<0.01) in the number of motor axons with 1- to 3-µm calibre and a 8% decrease (a decrease of 80 axons) in the number of motor axons with 6- to 9-µm calibre in 10-months old TDP-43$^{A315T}$ mice as compared to non-transgenic mice. The increase in the number of motor axons with 1- to 3-µm calibre was less (about 5%) and a slight decrease of 6% in 10-month old TDP-43$^{Wt}$ mice compared to non-transgenic mice (FIG. 21F). We have quantified the functional neuromuscular junctions (NMJs) through fluorescence staining for pre- and postsynaptic markers. NMJ count revealed that 5±4% of the analyzed NMJs were denervated in 10-month old TDP-43$^{Wt}$ mice and 10±5% were denervated in age-matched TDP-43$^{G348C}$ mice as compared to non-transgenic controls. Furthermore, over 20% of NMJs were partially denervated in both TDP-43$^{Wt}$ mice and TDP-43$^{G348C}$ mice.

The severe alterations in motor axon morphology of TDP-43$^{G348C}$ mice prompted us to examine whether this phenomenon was associated with caspase-3 activation, a sign of neuronal damage. Using double immunofluorescence and antibodies against cleaved caspase-3 and NeuN (a neuronal marker), we found many cleaved caspase-3 positive neurons in the spinal cord of TDP-43$^{G348C}$ mice at 10-months age (FIG. 21J-L) compared to 3-months old TDP-43$^{G348C}$ mice (FIG. 21G). Cleaved caspase-3 positive cells were also positive for cytoplasmic TDP-43 (FIG. 21M-O). However, no caspase-3 positive neurons were detected in TDP-43$^{Wt}$ and TDP-43$^{A315T}$ mice at 10 months of age (data not shown).

Example 14 TDP-43 Transgenic Mice Develop Motor Dysfunction and Cognitive Deficits Behavioural analysis of the TDP-43 transgenic mice revealed age-related cognitive defects, particularly learning and memory deficits. We used passive avoidance test to detect deficiencies in contextual memory. No defects were detected until 7 months of age. However, after 7 months TDP-43$^{Wt}$, TDP-43$^{A315T}$ and TDP-43$^{G348C}$ mice exhibited severe cognitive impairments, especially in the 11$^{th}$ and 13$^{th}$ months (FIG. 22A). The most robust memory deficit occurred in TDP-43$^{G348C}$ mice. We then conducted Barnes maze test to specifically discern the spatial learning and memory deficits in these mice. The TDP-43$^{G348C}$ and to a lesser extent TDP-43$^{Wt}$ mice had significant learning impairment in the Barnes maze test at 10 months of age (FIG. 22B-C) as depicted by significant reduction in the time spent in the target quadrant and increased primary errors. In the probe trial (Day 5), TDP-43$^{G348C}$ and TDP-43$^{Wt}$ mice showed a significant reduction in the time spent in the target quadrant and increase in the total number of errors as compared to age-matched non-transgenic mice (FIG. 22B-C). Thus, 10-months old TDP-43$^{G348C}$ mice had severe spatial learning and memory deficits. Transgenic mice overexpressing TDP-43$^{G348C}$, TDP-43$^{A315T}$ or TDP-43$^{Wt}$ exhibited also age-related motor deficits as depicted by significant reductions in latency in the accelerating rotarod tests starting at about 42-weeks of age (FIG. 22D).

Example 15 Age-Related Neuroinflammatory Changes in TDP-43 Mice Precede Behavioural Defects The microgliosis and astrogliosis were assessed in spinal cord and brains sections of different transgenic mice at presymptomatic stage (3 months) and after appearance of behavioural and sensorimotor deficits (10 months). Antibodies against Iba-1, a marker for microglial ion channel, revealed the existence of microgliosis in the brain and spinal cord sections of 10-months old TDP-43 transgenic mice (FIG. 23A-J). The microgliosis in the brain and spinal cord sections of 10-months old TDP-43$^{Wt}$ and TDP-43$^{A315T}$ mice was less pronounced than in 10-months TDP-43$^{G348C}$ mice (FIG. 22E-H). Microgliosis was age-dependent as both spinal cord and brain sections of 3-months old TDP-43$^{Wt}$, TDP-43$^{A315T}$ (Data not shown) and TDP-43$^{G348C}$ mice (FIG. 23B&G) had far less microglial activation than 10-months old mice of same genotype. We also used antibodies against glial fibrillary acidic protein (GFAP) to detect astrogliosis in the brain (FIG. 23P-T) and spinal cord (FIG. 23K-O) sections of 10-months old TDP-43 transgenic mice. Again, astrogliosis in TDP-43$^{Wt}$ and TDP-43$^{A315T}$ mice was less severe than in TDP-43$^{G348C}$ mice. Similar to microgliosis, astrogliosis was also age-dependent as both spinal cord and brain sections of 3-months old TDP-43$^{Wt}$, TDP-43$^{A315T}$ (Data not shown) and TDP-43$^{G348C}$ mice (FIG. 23L&Q) had far less astroglial activation than 10-months old mice of same genotype. We then quantified mRNA levels of various pro-inflammatory cytokines and chemokines in the spinal cord of 10-months old transgenic mice using quantitative real-time PCR. The mRNA levels of all studied cytokines and chemokines were upregulated in TDP-43$^{Wt}$, TDP-43$^{A315T}$ and TDP-43$^{G348C}$ mice when compared to their non-transgenic littermates. For instance, the levels of TNF-α (2.7-fold), IL-6 (2-fold), and MCP-1 (2.5-fold) were all upregulated in TDP-43$^{G348C}$ mice as compared to TDP-43$^{Wt}$ mice (FIG. 23U).

We next asked the question whether neuroinflammatory signals can be detected in early, pre-onset staged of the disease. Previous results, using the sensitive live imaging approaches in SOD1 mutant models, revealed that one of the first signs of the disease is the transient induction of the GFAP signals (Keller et al., 2009). To investigate the temporal induction of gliosis and to relate it to sensorimotor and learning deficits, we generated by breeding double transgenic mice carrying a TDP-43 transgene and a GFAP-luc transgene consisting of the reporter luciferase (luc) driven by the murine GFAP promoter.

To analyse the spatial and temporal dynamics of astrocytes activation/GFAP induction in TDP-43 mouse model, we performed series of live imaging experiments, starting at early 4-5 weeks of age until 52-weeks. Quantitative analysis of the imaging signals revealed an early (~20 weeks) and significant upregulation of GFAP promoter activity (FIG. 24A-H) in the brain of TDP-43$^{G348C}$/GFAP-luc mice. Starting at 20 weeks of age, the light signal intensity from the brain of TDP-43$^{A315T}$/GFAP-luc mice and TDP-43$^{Wt}$/GFAP-luc mice was also significantly elevated when compared to wild-type littermates, but the intensity was less than in GFAP-luc/TDP-43$^{G348C}$ mice. The GFAP promoter activity in the brain progressively increased with age until it peaked at ~50 weeks for GFAP-luc/TDP-43$^{G348C}$, and at ~46 weeks for GFAP-luc/TDP-43$^{A315T}$ and GFAP-luc/TDP-43$^{Wt}$ mice (FIG. 24Q). It is noteworthy that the induction of gliosis at 20 weeks in the brain of TDP-43 transgenic mice preceded the cognitive deficits first detected at ~28 weeks (FIG. 26). Likewise, in the spinal cord of all three TDP-43 mouse models, the induction of GFAP promoter activity signals at ~30 weeks of age (FIGS. 24I-P & R) preceded the motor dysfunction first detected by the rotarod test at ~36 weeks of age. Hence, TDP-43 mediated pathogenesis is associated with an early induction of astrogliosis/GFAP signals and age dependent neuroinflammation.

Example 16 Analysis of Motor Behavior in WA-Treated Mice

Analysis of motor behavior using accelerating rotarod showed that WA-treated TDP-43$^{G348C}$ mice had significantly better motor performance compared with untreated TDP-43$^{G348C}$ mice. Accelerating rotarod analysis was performed in TDP-43$^{G348C}$ mice at various ages from 8 wk to 52 wk, and time taken by the mice to fall from the rotarod is used as rotarod performance. WA treatment period is marked as drug treatment period. Error bars represent mean±SEM (n=10 each group) (FIG. 25).

Materials and Methods

Human Subjects

The spinal cords of 16 subjects with sporadic ALS and 6 control cases were used in this study. The diagnosis of ALS was made on both clinical and pathological grounds. The ages at death ranged from 42 to 79 years, and the duration of illness ranged from 21 to 48 months (S-Table 3 Swamp et al. *J Exp Med* 2011, 208, 2429-2447). TDP-43-positive inclusions were found in all ALS cases. We also used spinal cord samples from 6 neurologically normal individuals (normal controls), aged between 55 and 84 years. For routine histological examination, the spinal cord of each subject was fixed with 10% buffered formalin for 3 weeks and then embedded in paraffin; 4-μm-thick sections were cut and stained with hematoxylin.

Generation of TDP-43 Transgenic Mice

TARDBP (NM_007375) was amplified by PCR from a human BAC clone (clone RPCI-11, clone number: 829B14) along with the endogenous promoter (~4 kB). A315T and G348C mutations in TDP-43 were inserted using site-directed mutagenesis (FIG. 9). The full-length genomic TARDBP (TDP-43$^{Wt}$ and TDP-43$^{G348C}$) was linearized by Swa-1 restriction enzyme and a 18 kb DNA fragment microinjected in one-day mouse embryos (having a background of C3HxC57Bl/6). The embryos were implanted in pseudo-pregnant mothers (having ICR CD1 background). Founders were bred with non-transgenic C57Bl/6 mice to establish stable transgenic lines (FIG. 9A-D). Transgene expression was analyzed in brain and spinal cord by real-time PCR and in brain, spinal cord, muscle, liver by western blot using monoclonal human TDP-43 antibody (Clone E2-D3, Abnova). The use and maintenance of the mice described in this article were performed in accordance to the Guide of Care and Use of Experimental Animals of the Canadian Council on Animal Care.

Withaferin a Treatment

Withaferin A (Enzo life sciences, Plymouth meeting, PA, USA) were injected intra-peritoneally twice a week for 10-consecutive weeks at 3 mg/kg body weight in 30-weeks old TDP-43$^{Wt}$ mice (n=10). Age matched control non-transgenic animals (n=10) and in TDP-43$^{Wt}$ (n=10) littermates were injected twice a week with 0.9% saline intra-peritoneally. All the behavioral and imaging experiments were conducted in a double blind manner as such the experimenter had no knowledge of the drug treatment or the genotype of animals.

Plasmids

Mammalian expression vector plasmids pCMV-p65, ICAM-luc (positions −340 to −25) and luciferase reporter plasmids 4κB$^{wt}$-luc or 4 κB$^{mut}$-luc, containing four tandem copies of the human immunodeficiency virus-B sequence upstream of minimal SV40 promoter and mutant IκB-α (IκB$^{SR}$) containing Ser$^{32}$ and Ser$^{36}$-to-alanine mutations were generous gifts from the lab of Dr. Michel J. Tremblay, CRCHUQ. To create a human pCMV-TDP43, the cDNA library from human myeloid cells was amplified by polymerase chain reaction (PCR) using primers as described in S-Table 1 (Swamp et al. *J Exp Med* 2011, 208, 2429-2447). These products were subcloned into TOPO-vector (Invitrogen, Carlsbad, Calif., USA) and later digested with Kpn1-BamHI restriction enzymes and subcloned in frame into pcDNA3.0 vector to form pCMV-TDP43$^{wt}$. The hemagglutinin (HA) tag was later added by PCR. HA tagged TDP-43$^{ΔN}$, TDP-43$^{ΔRRM-1}$, TDP-43$^{ΔRRM-2}$ and TDP-43$^{ΔC}$ deletion mutants were constructed by PCR amplification and cloned between Kpn1-BamHI sites using the primers described in S-Table 1 (Swarup et al. *J Exp Med* 2011, 208, 2429-2447). Point mutations (pCMV-TDP43$^{A315T}$ and pCMV-TDP43$^{G348C}$) were inserted by PCR using site directed mutagenesis.

Cell Culture and Transfection

Mouse microglial BV-2 and mouse neuroblastoma N2a cells were maintained in Dulbecco's modified Eagle's medium (Gibco, Carlsbad, Calif., USA) with 10% fetal bovine serum and antibiotics. Cells were transfected using Lipofectamine 2000 transfection reagent (Invitrogen, Carlsbad, Calif., USA) according to the manufacturer's instructions. At 48 h post-transfection, the cells were harvested, and the extracts were prepared for downstream assays.

Primary Cell Cultures

Primary microglial culture from brain tissues of neonatal (P0-P1) C57Bl/6, TDP-43$^{Wt}$, TDP-43$^{A315T}$ and TDP-43$^{G348C}$ mice were prepared as described previously[22]. Briefly, the brain tissues were stripped of their meninges and minced with scissors under a dissecting microscope in DMEM. After trypsinization (0.5% trypsin, 10 min, 37° C./5% $CO_2$) the tissue was triturated. The cell suspension was washed in culture medium for glial cells [DMEM supplemented with 10% FBS (Gibco), L-glutamine (1 mM), sodium pyruvate (1 mM), penicillin (100 units/ml), and streptomycin (100 mg/ml)] and cultured at 37° C./5% $CO_2$ in 75-cm$^2$ Falcon tissue-culture flasks (BD, San Jose, Calif., USA) coated with polyD-lysine (PDL) (10 mg/ml; Sigma-Aldrich) in borate buffer [2.37 g of borax and 1.55 g of boric acid dissolved in 500 ml of sterile water (pH 8.4)] for 1 h, then rinsed thoroughly with sterile, glass-distilled water. Half of the medium was changed after 6 h in culture and every second day thereafter, starting on day 2, for a total culture time of 10-14 days. Microglia were shaken off the primary mixed brain glial cell cultures (150 rpm, 37° C., 6 h) with maximum yields between days 10 and 14, seeded (10$^5$ cells per milliliter) onto PDL-pretreated 24-well plates (1 ml per well), and grown in culture medium for microglia [DMEM supplemented with 10% FBS, L-glutamine (1 mM), sodium pyruvate (1 mM), 2-mercaptoethanol (50 mM), penicillin (100 units/ml), and streptomycin (100 mg/ml)]. The cells were allowed to adhere to the surface of a PDL-coated culture flask (30 min, 37° C./5% $CO_2$), and nonadherent cells were rinsed off.

Primary cortical cultures from brain tissues of gestation day 16 (E16) C57Bl/6, TDP-43$^{Wt}$, TDP-43$^{A315T}$ and TDP-43$^{G348C}$ mice were prepared as described. Briefly, dissociated cortical cells (2.5-3.5 hemispheres) were plated onto PDL-coated 24-well, containing DMEM supplemented with 20 mM glucose, 2 mM glutamine, 5% fetal bovine serum, and 5% horse serum. Cytosine arabinoside was added 4-5 days after the plating to halt the growth of nonneuronal cells. Cultures were maintained at 37° C. in a humidified CO2 incubator and used for experiments between 14 and 21 days in vitro. Cells were treated with Withaferin A (Enzo life sciences, Plymouth meeting, PA, USA) at a final concentration of 1 μM for 24 hrs. Bone-marrow derived macrophages (BMMs) were isolated and cultured using established protocols as described elsewhere[23].

Co-Immunoprecipitation and Western Blot Assays

After transfection of plasmids, BV-2 cells were cultured for 48 h and then harvested with lysis buffer (25 mM HEPES-NaOH (pH 7.9), 150 mM NaCl, 1.5 mM $MgCl_2$, 0.2 mM EDTA, 0.5% Triton-X-100, 1 mM dithiothreitol, protease inhibitor cocktail). Alternatively, spinal cords from TDP-43 transgenic mice or sporadic ALS subjects along with controls were lysed in the buffer. The lysate was incubated with 50 μl of Dynabeads (Protein-G beads, Invitrogen), anti-TDP-43 polyclonal (ProteinTech, Chicago, Ill., USA) and anti-HA antibody (clone 3F10, Roche, San Francisco, Calif., USA). After subsequent washing, the beads were incubated overnight at 4° with 400 μg of cell lysate. Antibody-bound complexes were eluted by boiling in Laemmli sample buffer. Supernatants were resolved by 10% SDS-PAGE and transferred on nitrocellulose membrane (Biorad, Hercules, Calif., USA). The membrane was incubated with anti-p65 antibody, and immunoreactive proteins were visualized by chemiluminescence (Perkin and Elmer, Santa Clara, Calif., USA) as described previously[24]. In some cases, phospho-p65$^{Ser536}$ (Cell Signaling, Boston, Mass., USA) was used at a concentration of 1:1000.

Mass Spectrometer Analysis

BV-2 microglial cells were transiently transfected with plasmid vector pCMV-TDP43$^{wt}$ coding for TDP-43$^{wt}$ tagged with hemagglutinin (HA) and subsequently treated with LPS. 48 hrs after transfection, the LPS-challenged BV-2 cells were then harvested and cell extracts co-immunoprecipitated with anti-HA antibody. Proteins were resolved in 4-20% Tris-glycine gels (Precast gels, Biorad) and stained with Sypro-Ruby (Biorad). Protein bands from the gel were excised and subjected to mass spectrometer analysis at the Proteomics Platform, Quebec Genomics Centre, Quebec. The experiments were performed on a Thermo Surveyor MS pump connected to a LTQ linear ion trap mass spectrometer (Thermo Electron, San Jose, Calif., USA) equipped with a nanoelectrospray ion source (Thermo Electron). Scaffold (version 1.7; Proteome Software Inc., Portland, Oreg., USA) was used to validate MS/MS-based peptide and protein identifications. Peptide identifications were accepted if they could be established at >90.0% probability as specified by the Peptide Prophet algorithm[25].

Immunofluorescence Microscopy

Cells were grown to 70% confluence on glass coverslips and fixed in 2% paraformaldehyde for 30 min. In some cases BV-2 cells were transiently transfected with the pCMV-TDP-43$^{wt}$ and pCMV-p65 vectors using the Lipofectamine2000 reagent. After fixation with 4% paraformaldehyde (PFA), cells were washed in phosphate-buffered saline (PBS), and permeabilized with 0.2% Triton X-100 in PBS for 15 min. After blocking coverslips with 5% normal goat serum for 1 hr at room temperature, primary antibody incubations were performed in 1% normal goat serum in PBS overnight, followed by an appropriate Alexa Fluor 488 or 594 secondary antibody (Invitrogen) for 1 hr at room temperature. Similar procedures were used for staining spinal cord sections from TDP-43 transgenic mice and sections of sporadic ALS cases. Cells were viewed using a 40× or 63× oil immersion objectives on a Leica DM5000B microscope (Leica Microsystems, Bannockburn, Ill., USA).

Quantitative Real-Time RT-PCR

Real-time RT-PCR was performed with a LightCycler 480 (Roche Diagnostics) sequence detection system using Light-Cycler SYBR Green I at the Quebec genomics Centre, Quebec. Total RNA was extracted from cell culture experiments using Trizol reagent (Invitrogen). Total RNA was treated with DNase (Qiagen, Valencia, Calif., USA) to get rid of genomic DNA contaminations. Total RNA was the quantified using Nanodrop and its purity verified by Bioanalyzer 2100 (Agilent Technologies, Santa Clara, Calif., USA). Gene-specific primers were constructed using the GeneTools (Biotools Inc.) software. 3 genes Atp5, Hprt1 and GAPDH were used as internal control genes. The primers used for the analysis of genes are given in S-Table 2 (Swamp et al. *J Exp Med* 2011, 208, 2429-2447).

Cytotoxicity Assay

N2a cells were transfected with pCMV-hTDP-43 (both wild type and mutants). 48 hrs after transfection, cells were treated with the conditioned media derived from BV-2 cells, some of which were treated with Lipopolysaccharide (0111: B4 serotype; Sigma). 24 hrs after challenging N2a cells, culture supernatants were assayed for CytoTox-ONE Homogeneous Membrane Integrity Assay (Promega, Wis., USA), a fluorimetric assay which depends on the levels of lactate dehydrogenase (LDH) released due to cell death[26]. The assay was performed according to the manufacturer's protocol. Fluorescence was measured using a SpectraMAX Gemini EM (Molecular Devices, Sunnyvale, Calif., USA) fluorescence plate reader at an excitation wavelength of 560 nm and an emission wavelength of 590 nm. Similar techniques were used for primary cortical neurons derived from TDP-43 transgenic mice.

ELISA

The levels of TNF-α, IL-1β, IL-6 and IFN-γ were assayed by multi-analyte ELISA kit (mouse inflammatory cytokine array, SABiosciences, Frederick, Md., USA). Mouse p65 ELISA (Stressgen, Ann Arbor, Mich., USA) and human p65 ELISA (SABiosciences) were carried out according to manufacturer's instructions. For TDP-43 ELISA, we used sandwich-ELISA protocol. Briefly ELISA plates were incubated in mouse monoclonal antibody against TDP-43 (Abnova, clone E2-D3) overnight and the total protein extracts (both soluble and insoluble fractions) were incubated in pre-coated plates. A second TDP-43 polyclonal antibody (ProteinTech) was further added and ELISA performed as described elsewhere[27, 28]. The standard curve for the ELISA assay was carried out with triplicate measurements using 100 μl/well of recombinant TDP-43 protein (MW 54.3 kDa, AAH01487, recombinant protein with GST tag, Abnova Corporation, Walnut, USA) solution at different concentrations (0.24, 0.48, 0.97, 1.9, 3.9, 7.8, 15.6, 31.2, 62.5, 125, 250, 500, 1000 and 1250 ng/ml) of the protein in PBS. The relative concentration estimates of TDP-43 were calculated according to each standard curve.

Nitrite and Reactive Oxygen Species Assays

The cell culture supernatants from cortical neurons or N2a cells were assayed for nitrite concentration using Griess Reagent (Invitrogen) as described elsewhere[29]. The supernatants were also assayed for reactive oxygen species (ROS) using H2DCFDA (Sigma, St. Louis, Mo., USA).

Electrophoretic Mobility Shift Assay (EMSA)

48 hrs after transfection of CMV-p65 with pCMV-TDP43$^{WT}$ or pCMV-TDP43$^{G348C}$ and treatment with LPS, BV-2 cells were harvested and nuclear extracts prepared. Nuclear proteins were extracted using a protein extraction kit Panomics (Redwood City, Calif., USA) as per the manufacturer's instructions. Concentrations of nuclear proteins were determined on diluted samples using a Bradford assay (Biorad). Interaction between p65 in the protein extract and DNA probe was investigated using EMSA kit from Panomics as per the manufacturer's instructions. These nuclear extracts were incubated with NF-κB binding site specific oligonucleotides coated with streptavidin. Electrophoretic mobility shift assay (EMSA) was then performed using the NF-κB EMSA kit.

Reporter Gene Assays

BV2 cells were harvested in 120 μl of cell lysis buffer (Promega, Madison, Wis., USA), and an ensuing 1-min centrifugation step (20,000×g) yielded a luciferase-containing supernatant. In both cases aliquots of 20-μl supernatant were tested for luciferase activity (luciferase assay kit, Promega) and for β-galactosidase activity (β-galactosidase assay kit, Promega) to adjust for transfection efficiency.

RNA Intereference

To selectively prevent TDP-43 expression, we employed the RNA interference technology. A double-stranded RNA (siRNA) was employed to degrade TDP-43 mRNA and thus to limit the available protein. The siRNA experiments were designed and conducted as described earlier[26]. The siRNAs directed against the murine TDP-43 mRNA (NM_145556.4) consisted of sequences with symmetrical 3'-UU overhangs using siRNA Target Finder (Ambion, Tex., USA). The sequence of the most effective TDP-43 siRNAs represented is as follows: 5'-AGGAAUCAGCGUGCAUAUAUU-3' (SEQ ID NO:17), 5'-UAUAUGCACGCUGAUUCCUUU-3' (SEQ ID NO:18). To account for the non-sequence-specific effects, scrambled siRNA was used. The sequence of scrambled siRNA is as follows: 5'-GUGCA-CAUGAGUGAGAUUU-3' (SEQ ID NO:19) and 5'-CACGUGUACUCACUCUAAA-3' (SEQ ID NO:20). TDP-43 siRNAs or the scrambled siRNAs were suspended in diethyl gyro-carbonate water to yield desired concentration. For in vitro transfection, cells were plated in 24-well plates and transfected with 0.6 μmol/L siRNAs with 2 μL Lipofectamine 2000 (Invitrogen). The cells were then kept for 72 h in OptiMEM medium (Gibco).

Accelerating Rotarod

Accelerating rotarod was performed on mice at 4 rpm speed with 0.25 rpm/sec acceleration as described elsewhere[30]. Mice were subjected to three trials per session and every two weeks.

In Vivo Bioluminescence Imaging

As previously described[31, 32], the images were gathered using IVIS® 200 Imaging System (CaliperLSXenogen, Alameda, Calif., USA). Twenty-five minutes prior to imaging session, the mice received intraperitoneal (i.p.) injection of the luciferase substrate D-luciferine (150 mg/kg—for mice between 20 and 25 g, 150-187.5 ml of a solution of 20 mg/ml of D-luciferine dissolved in 0.9% saline was injected) (CaliperLS-Xenogen).

Statistical Analysis

For statistical analysis, the data obtained from independent experiments are presented as the mean±SEM; they were analyzed using a paired t-test with Mann-Whitney test, 1-way ANOVA with Kruskal-Wallis test or 2-way ANOVA with Bonferroni adjustment for multiple comparisons using the GraphPad Prism Software version 5.0 (La Jolla, Calif., USA). For rotarod and GFAP imaging studies, repeated measures ANOVA was used. In some experiments, an unpaired t-test followed by a Welch's test was performed. Differences were considered significant at p<0.05.

DNA Constructs and Generation of WT, A315T and G348C TDP-43 Transgenic Mice.

TARDBP (NM_007375) was amplified by PCR from a human BAC clone (clone RPCI-11, clone number: 829B14) along with the endogenous promoter (~4 kb). A315T and G348C mutations in TDP-43 were inserted using site-directed mutagenesis. The full-length genomic TARDBP (TDP-43$^{Wt}$ TDP-43$^{A315T}$, and TDP-43$^{G348C}$) was linearized by Swa-1 restriction enzyme and an 18 kb DNA fragment microinjected in one-day mouse embryos (having a background of C3H×C57Bl/6). Founders were identified by southern blotting and were bred with non-transgenic C57Bl/6 mice to establish stable transgenic lines. The transgenic mice were identified by PCR amplification of the human TARDBP gene using the following primer pairs as listed in Table 4. The mRNA was analysed in brain and spinal cord by real-time PCR and protein analyzed by western blot using monoclonal human TDP-43 antibody (Clone E2-D3, Abnova, Walnut, Calif., USA). To avoid the effects of genetic background, all experiments were performed on aged-matched littermates. The use and maintenance of the mice described in this article were performed in accordance to the Guide of Care and Use of Experimental Animals of the Canadian Council on Animal Care.

TABLE 4

| Gene Symbol | Forward Primer | Reverse Primer |
| --- | --- | --- |
| TDP-43$^{Wt}$ | CTCTTTGTGGAGAGGAC (SEQ ID NO: 9) | CCCCAACTGCTCTGTAG (SEQ ID NO: 10) |
| TDP-43$^{A315T}$ | CTCTTTGTGGAGAGGAC (SEQ ID NO: 11) | TTATTACCCGATGGGCA (SEQ ID NO: 12) |
| TDP-43$^{G348C}$ | CTCTTTGTGGAGAGGAC (SEQ ID NO: 13) | GGATTAATGCTGAACGT (SEQ ID NO: 14) |
| GFAP-luc | GAAATGTCCGTTCGGTTGGCAGAAGC (SEQ ID NO: 15) | CCAAAACCGTGATGGAATGGAACAACA (SEQ ID NO: 16) |

Co-Immunoprecipitation and Western Blot Assays

Snap frozen spinal cords of mice were harvested with lysis buffer containing 25 mM HEPES-NaOH (pH 7.9), 150 mM NaCl, 1.5 mM MgCl$_2$, 0.2 mM EDTA, 0.5% Triton-X-100, 1 mM dithiothreitol and protease inhibitor cocktail. Protein samples were estimated using Bradford method. The lysate was incubated with 50 µl of Dynabeads (Protein-G beads, Invitrogen), anti-TDP-43 polyclonal (ProteinTech, Chicago, Ill., USA) or anti-peripherin polyclonal antibody (AB1530, Chemicon, Billerica, Mass., USA). After subsequent washing, the beads were incubated overnight at 4° C. with 400 g of tissue lysate. Antibody-bound complexes were eluted by boiling in Laemmli sample buffer. Supernatants were resolved by 10% SDS-PAGE and transferred on nitrocellulose membrane (Biorad, Hercules, Calif., USA). The membrane was incubated with anti-ubiquitin antibody (1:1000, Abcam, Cambridge, Mass., USA). For other western blot assays, blots were incubated with primary antibodies against human monoclonal TARDBP antibody (1:1000, Abnova, clone E2-D3), peripherin polyclonal (1:1000, Chemcion—AB1530), peripherin monoclonal (1:500, Chemicon, AB1527), Clone NR4 for NF-L (1:1000, Sigma), Clone NN18 for NF-M (1:1000, Millipore) and Clone N52 for NF-H (1:1000, Millipore). Immunoreactive proteins were then visualized by chemiluminescence (Perkin and Elmer, Santa Clara, Calif., USA) as described previously (Dequen et al., 2008). Actin (1:10000, Chemicon) is used as a loading control.

Immunohistochemistry/Immunofluorescence Microscopy

4% Paraformaldehyde (PFA) fixed spinal cord and brain sections of mice were sectioned and fixed on slides. For immunohistochemistry, tissues were treated with hydrogen-peroxide solution before permeabilisation. After blocking with 5% normal goat serum for 1 hr at room temperature, primary antibody incubations were performed in 1% normal goat serum in PBST overnight, followed by an appropriate Alexa Fluor 488 or 594 secondary antibody (1:500, Invitrogen) for 1 hr at room temperature. For immunohistochemistry, tissues were incubated in biotinylated secondary antibodies (1:500, Vector labs, Burlingame, Calif., USA), incubated in avidin-biotin complex and developed using Dab Kit (Vector labs). Z-stacked sections were viewed using a 40× or 60× oil immersion objectives on an Olympus Fluoview™ Confocal System (Olympus, Center Valley, Pa., USA).

Neurofilament ELISA

Wells of microtiter plates were coated with 0.1% NaN3/TBS including the primary antibodies (NR4; 1:600, N52; 1:1000, NN18; 1:500). The coated wells were incubated with 10% normal goat serum/0.2% Tween 20/TBS for 30 min at 37° C. After washing twice with TBS, an aliquot (100 µL) of the diluted samples was applied in each well, and incubated overnight at 4° C. Further ELISA was performed using standard procedure as described elsewhere (Noto et al., 2010).

Quantitative Real-Time RT-PCR

Real-time RT-PCR was performed with a LightCycler 480 (Roche Diagnostics) sequence detection system using LightCycler SYBR Green I at the Quebec genomics Centre, Quebec. Total RNA was extracted from frozen spinal cord or brain tissues using Trizol reagent (Invitrogen). Total RNA was treated with DNase (Qiagen, Valencia, Calif., USA) to get rid of genomic DNA contaminations. Total RNA was then quantified using Nanodrop and its purity verified by Bioanalyzer 2100 (Agilent Technologies, Santa Clara, Calif., USA). Gene-specific primers were constructed using the GeneTools (Biotools Inc.) software v.3. Genes Atp5 and GAPDH were used as internal control genes. The primers used for the analysis of genes are described in Swamp et al. Brain, 2011; 134; 2610-2626. The presence of GFAP-luc transgene was assessed by PCR with HotStar Taq Master mix Kit (Quiagen, Mississauga, ON, Canada) in 15 mM MgCl$_2$ PCR buffer with the known primers (Keller et al., 2009; Keller et al., 2010).

Barnes Maze Task

For spatial learning test, the Barnes maze task was performed as described previously (Prut et al., 2007). The animals were subjected to four trials per session with an inter-trial interval (ITI) of 15 min. The probe trial takes 90 sec (half of the time used for the training trials) per mouse. Twelve days after the first probe trial mice are tested again in a second probe trial that takes 90 sec per mouse. Mice are not tested between the two probe trials. The time spent by the individual mice to reach the platform was recorded as the primary latency using video tracking software (ANY-maze, Wood Dale, Ill., USA).

Step-Through Passive Avoidance Test

A two-compartment step-through passive avoidance apparatus (Ugo basile, Collegeville, Pa., USA) was used. The apparatus is divided into bright and dark compartments by a wall with a guillotine door. The bright compartment was illuminated by a fluorescent light (8 W). Mice at various ages were placed in the bright compartment and allowed to explore for 30 s, at which point the guillotine door was raised to allow the mice to enter the dark compartment. When the mice entered the dark compartment, the guillotine door was closed and an electrical foot shock (0.6 mA) was delivered for 4 sec only on the $2^{nd}$ day. On the test day ($3^{rd}$ day) mice were placed in the bright compartment, no shock was given, and their delay in latency to enter the dark compartment was recorded. The procedure was repeated every month to test the mice at different ages.

Neuromuscular Junction Staining and Count

For monitoring the neuromuscular junctions, 25 mm thick muscle sections were incubated for 1 h in 0.1 M glycine in PBS for 2 h at RT and then stained with Alexa Fluor 594-conjugated α-bungarotoxin (1:2000, Molecular Probes/Invitrogen detection technologies, Carlsbad, Calif., USA) diluted in 3% BSA in PBS for 3 h at RT. After washing in PBS, the muscle sections were blocked in 3% BSA, 10% goat serum and 0.5% Triton X-100 in PBS overnight at 48° C. The next day, the sections were incubated with mouse antineurofilament antibody 160 K (1:2000, Temecula, Calif., USA) and mouse anti-synaptophysin (Dako, Mississauga, ON, Canada) in the same blocking solution overnight at 48° C. After washing for 5 h, muscle sections were incubated with goat anti-mouse Alexa Fluor 488-conjugated secondary antibody (Probes/Invitrogen detection technologies, Carlsbad, Calif., USA) diluted 1:500 in blocking buffer for 3 h at RT. Three hundred neuromuscular junctions were counted per animal sample, discriminating both innervated and denervated junctions as described above. Frequencies of innervation, partial denervation and denervation were then converted to percentages for statistical analyses (n=5, two-way ANOVA with Bonferroni post-test).

Accelerating Rotarod

Accelerating rotarod was performed on mice at 4 rpm speed with 0.25 rpm/sec acceleration as described elsewhere (Gros-Louis et al., 2008). Mice were subjected to three trials per session and every two weeks.

In Vivo Bioluminescence Imaging

As previously described, (Keller et al., 2009; Keller et al., 2010) the images were gathered using IVIS® 200 Imaging System (CaliperLSXenogen, Alameda, Calif., USA). Twenty-five minutes prior to imaging session, the mice received intraperitoneal (i.p.) injection of the luciferase substrate D-luciferine (150 mg/kg—for mice between 20 and 25 g, 150-187.5 ml of a solution of 20 mg/ml of D-luciferine dissolved in 0.9% saline was injected) (CaliperLS-Xenogen).

Statistical Analysis

For statistical analysis, the data obtained from independent experiments are presented as the mean±SEM. A two-way analysis of variance (ANOVA) with repeated measures was used to study the effect of group (transgenic and non-transgenic mice) and time (in months or weeks) on latency to fall (accelerating rotarod test), latency to go to the dark chamber (passive avoidance test), primary errors and primary latency (Barnes maze test). Two-way ANOVA with repeated measures was also used for axonal calibre distribution and total flux of photons for in vivo imaging. The mixed procedure of the SAS software version 9.2 (SAS Institute Inc., Cary, N.C., USA) was used with a repeated statement and covariance structure that minimize the Akaike information criterion. The method of Kenward-Roger was used to calculate the degree of freedom. Pairwise comparisons were made using Bonferroni adjustment. One-way ANOVA was performed using GraphPad Prism Software version 5.0 (La Jolla, Calif., USA) for real-time inflammation array, real-time RT-PCR and neurofilament ELISA analysis. Post-hoc comparisons were performed by Tukey's test, with the statistical significance set at $p<0.05$.

Withaferin A administration

The drug used in this study was Withaferin A, obtained from Enzo Life sciences (Farminngdale, N.Y.). Withaferin A was first dissolved in DMSO and diluted in 0.9% saline. The final concentration of DMSO was 10%. The drug was made fresh every two weeks and was protected from light. Male and female transgenic mice and their transgenic littermates were divided randomly into following two groups (n=8 per group): (A) Transgenic control, which received vehicle (0.9% Saline with 10% DMSO) and (B) Transgenic WFA treatment group, which received an intraperitoneal injection of WFA at the rate of 4 mg/kg body weight, twice a week.

Animals were observed weekly for onset of disease symptoms (body weight and reflex score), as well as progression to death. Onset of disease was scored as the first observation of abnormal gait or overt hind limb weakness. End-stage of the disease was scored as complete paralysis of both hind limbs and the inability of the animals to right themselves after being placed on their side.

REFERENCES

1. Neumann, M., et al. Ubiquitinated TDP-43 in frontotemporal lobar degeneration and amyotrophic lateral sclerosis. *Science* 314, 130-133 (2006).
2. Dreyfuss, G., Matunis, M. J., Pinol-Roma, S. & Burd, C G hnRNP proteins and the biogenesis of mRNA. *Annu Rev Biochem* 62, 289-321 (1993).
3. Arai, T., et al. TDP-43 is a component of ubiquitin-positive tau-negative inclusions in frontotemporal lobar degeneration and amyotrophic lateral sclerosis. *Biochem Biophys Res Commun* 351, 602-611 (2006).
4. Corrado, L., et al. High frequency of TARDBP gene mutations in Italian patients with amyotrophic lateral sclerosis. *Hum Mutat* 30, 688-694 (2009).
5. Daoud, H., et al. Contribution of TARDBP mutations to sporadic amyotrophic lateral sclerosis. *J Med Genet* 46, 112-114 (2009).
6. Gitcho, M. A., et al. TDP-43 A315T mutation in familial motor neuron disease. *Ann Neurol* 63, 535-538 (2008).
7. Kabashi, E., et al. TARDBP mutations in individuals with sporadic and familial amyotrophic lateral sclerosis. *Nat Genet* 40, 572-574 (2008).
8. Sreedharan, J., et al. TDP-43 mutations in familial and sporadic amyotrophic lateral sclerosis. *Science* 319, 1668-1672 (2008).
9. Van Deerlin, V. M., et al. TARDBP mutations in amyotrophic lateral sclerosis with TDP-43 neuropathology: a genetic and histopathological analysis. *Lancet Neurol* 7, 409-416 (2008).
10. Wils, H., et al. TDP-43 transgenic mice develop spastic paralysis and neuronal inclusions characteristic of ALS and frontotemporal lobar degeneration. *Proc Natl Acad Sci USA* 107, 3858-3863 (2010).

11. Wegorzewska, I., Bell, S., Cairns, N.J., Miller, T. M. & Baloh, R. H. TDP-43 mutant transgenic mice develop features of ALS and frontotemporal lobar degeneration. *Proc Natl Acad Sci USA* 106, 18809-18814 (2009).
12. Stallings, N. R., Puttaparthi, K., Luther, C. M., Burns, D. K. & Elliott, J. L. Progressive motor weakness in transgenic mice expressing human TDP-43. *Neurobiol Dis* (2010).
13. Xu, Y. F., et al. Wild-Type Human TDP-43 Expression Causes TDP-43 Phosphorylation, Mitochondrial Aggregation, Motor Deficits, and Early Mortality in Transgenic Mice. *J Neurosci* 30, 10851-10859 (2010).
14. Sephton, C. F., et al. TDP-43 is a developmentally regulated protein essential for early embryonic development. *J Biol Chem* 285, 6826-6834 (2010).
15. Chiang, P. M., et al. Deletion of TDP-43 down-regulates Tbc1d1, a gene linked to obesity, and alters body fat metabolism. *Proc Natl Acad Sci USA* (2010).
16. Seyfried, N. T., et al. Multiplex SILAC analysis of a cellular TDP-43 proteinopathy model reveals protein inclusions associated with SUMOylation and diverse polyubiquitin chains. *Mol Cell Proteomics* 9, 705-718 (2010).
17. Boillee, S., Vande Velde, C. & Cleveland, D. W. ALS: a disease of motor neurons and their nonneuronal neighbors. *Neuron* 52, 39-59 (2006).
18. Boillee, S., et al. Onset and progression in inherited ALS determined by motor neurons and microglia. *Science* 312, 1389-1392 (2006).
19. Clement, A. M., et al. Wild-type nonneuronal cells extend survival of SOD1 mutant motor neurons in ALS mice. *Science* 302, 113-117 (2003).
20. Zhang, R., et al. Circulating endotoxin and systemic immune activation in sporadic amyotrophic lateral sclerosis (sALS). *J Neuroimmunol* 206, 121-124 (2009).
21. Zhang, R., et al. Gene expression profiling in peripheral blood mononuclear cells from patients with sporadic amyotrophic lateral sclerosis (sALS). *J Neuroimmunol* 230, 114-123 (2011).
22. Weydt, P., Yuen, E. C., Ransom, B. R. & Moller, T. Increased cytotoxic potential of microglia from ALS-transgenic mice. *Glia* 48, 179-182 (2004).
23. Davies, J. Q. & Gordon, S. Isolation and culture of murine macrophages. *Methods Mol Riot* 290, 91-103 (2005).
24. Dequen, F., Bomont, P., Gowing, G., Cleveland, D. W. & Julien, J. P. Modest loss of peripheral axons, muscle atrophy and formation of brain inclusions in mice with targeted deletion of gigaxonin exon 1. *J Neurochem* 107, 253-264 (2008).
25. Keller, A., Nesvizhskii, A. I., Kolker, E. & Aebersold, R. Empirical statistical model to estimate the accuracy of peptide identifications made by MS/MS and database search. *Anal Chem* 74, 5383-5392 (2002).
26. Swamp, V., Das, S., Ghosh, S. & Basu, A. Tumor necrosis factor receptor-1-induced neuronal death by TRADD contributes to the pathogenesis of Japanese encephalitis. *J Neurochem* 103, 771-783 (2007).
27. Kasai, T., et al. Increased TDP-43 protein in cerebrospinal fluid of patients with amyotrophic lateral sclerosis. *Acta Neuropathol* 117, 55-62 (2009).
28. Noto, Y. I., et al. Elevated CSF TDP-43 levels in amyotrophic lateral sclerosis: Specificity, sensitivity, and a possible prognostic value. *Amyotroph Lateral Scler* (2010).
29. Swamp, V., Ghosh, J., Duseja, R., Ghosh, S. & Basu, A. Japanese encephalitis virus infection decrease endogenous IL-10 production: correlation with microglial activation and neuronal death. *Neurosci Lett* 420, 144-149 (2007).
30. Gros-Louis, F., et al. Als2 mRNA splicing variants detected in KO mice rescue severe motor dysfunction phenotype in Als2 knock-down zebrafish. *Hum Mol Genet* 17, 2691-2702 (2008).
31. Cordeau, P., Jr., Lalancette-Hebert, M., Weng, Y. C. & Kriz, J. Live imaging of neuroinflammation reveals sex and estrogen effects on astrocyte response to ischemic injury. *Stroke* 39, 935-942 (2008).
32. Maysinger, D., Behrendt, M., Lalancette-Hebert, M. & Kriz, J. Real-time imaging of astrocyte response to quantum dots: in vivo screening model system for biocompatibility of nanoparticles. *Nano Lett* 7, 2513-2520 (2007).
33. Horvath, R. J., Nutile-McMenemy, N., Alkaitis, M. S. & Deleo, J. A. Differential migration, LPS-induced cytokine, chemokine, and NO expression in immortalized BV-2 and HAPI cell lines and primary microglial cultures. *J Neurochem* 107, 557-569 (2008).
34. Aleyasin, H., et al. Nuclear factor-(kappa)B modulates the p53 response in neurons exposed to DNA damage. *J Neurosci* 24, 2963-2973 (2004).
35. Pizzi, M., et al. Inhibition of IkappaBalpha phosphorylation prevents glutamate-induced NF-kappaB activation and neuronal cell death. *Acta Neurochir Suppl* 93, 59-63 (2005).
36. Oh, J. H., Lee, T. J., Park, J. W. & Kwon, T. K. Withaferin A inhibits iNOS expression and nitric oxide production by Akt inactivation and down-regulating LPS-induced activity of NF-kappaB in RAW 264.7 cells. *Eur J Pharmacol* 599, 11-17 (2008).
37. Thaiparambil, J. T., et al. Withaferin A inhibits breast cancer invasion and metastasis at sub-cytotoxic doses by inducing vimentin disassembly and serine 56 phosphorylation. *Int J Cancer* (2011).
38. Suzuki, M., et al. Increased expression of TDP-43 in the skin of amyotrophic lateral sclerosis. *Acta Neurol Scand* (2010).
39. Baumer, D., Parkinson, N. & Talbot, K. TARDBP in amyotrophic lateral sclerosis: identification of a novel variant but absence of copy number variation. *J Neurol Neurosurg Psychiatry* 80, 1283-1285 (2009).
40. Gitcho, M. A., et al. TARDBP 3'-UTR variant in autopsy-confirmed frontotemporal lobar degeneration with TDP-43 proteinopathy. *Acta Neuropathol* 118, 633-645 (2009).
41. Guerreiro, R. J., et al. TDP-43 is not a common cause of sporadic amyotrophic lateral sclerosis. *PLoS One* 3, e2450 (2008).
42. Dormann, D., et al. Proteolytic processing of TAR DNA binding protein-43 by caspases produces C-terminal fragments with disease defining properties independent of progranulin. *J Neurochem* 110, 1082-1094 (2009).
43. Igaz, L. M., et al. Expression of TDP-43 C-terminal Fragments in Vitro Recapitulates Pathological Features of TDP-43 Proteinopathies. *J Biol Chem* 284, 8516-8524 (2009).
44. Johnson, B. S., McCaffery, J. M., Lindquist, S. & Gitler, A. D. A yeast TDP-43 proteinopathy model: Exploring the molecular determinants of TDP-43 aggregation and cellular toxicity. *Proc Natl Acad Sci USA* 105, 6439-6444 (2008).
45. Zhang, Y. J., et al. Aberrant cleavage of TDP-43 enhances aggregation and cellular toxicity. *Proc Natl Acad Sci USA* 106, 7607-7612 (2009).

46. Bergmann, M., Hart, L., Lindsay, M., Barnes, P. J. & Newton, R. IkappaBalpha degradation and nuclear factor-kappaB DNA binding are insufficient for interleukin-1beta and tumor necrosis factor-alpha-induced kappaB-dependent transcription. Requirement for an additional activation pathway. *J Biol Chem* 273, 6607-6610 (1998).

47. Yoza, B. K., Hu, J. Y. & McCall, C. E. Protein-tyrosine kinase activation is required for lipopolysaccharide induction of interleukin 1beta and NFkappaB activation, but not NFkappaB nuclear translocation. *J Biol Chem* 271, 18306-18309 (1996).

48. Gerritsen, M. E., et al. CREB-binding protein/p300 are transcriptional coactivators of p65. *Proc Natl Acad Sci USA* 94, 2927-2932 (1997).

49. Perkins, N. D., et al. Regulation of NF-kappaB by cyclin-dependent kinases associated with the p300 coactivator. *Science* 275, 523-527 (1997).

50. Schmitz, M. L., Stelzer, G., Altmann, H., Meisterernst, M. & Baeuerle, P. A. Interaction of the COOH-terminal transactivation domain of p65 NF-kappa B with TATA-binding protein, transcription factor IIB, and coactivators. *J Biol Chem* 270, 7219-7226 (1995).

51. Schmitz, M. L., dos Santos Silva, M. A. & Baeuerle, P. A. Transactivation domain 2 (TA2) of p65 NF-kappa B. Similarity to TA1 and phorbol ester-stimulated activity and phosphorylation in intact cells. *J Biol Chem* 270, 15576-15584 (1995).

52. Sheppard, K. A., et al. Transcriptional activation by NF-kappaB requires multiple coactivators. *Mol Cell Riot* 19, 6367-6378 (1999).

53. Deng, H. X., et al. FUS-immunoreactive inclusions are a common feature in sporadic and non-SOD1 familial amyotrophic lateral sclerosis. *Ann Neurol* 67, 739-748 (2010).

54. Kwiatkowski, T. J., Jr., et al. Mutations in the FUS/TLS gene on chromosome 16 cause familial amyotrophic lateral sclerosis. *Science* 323, 1205-1208 (2009).

55. Vance, C., et al. Mutations in FUS, an RNA processing protein, cause familial amyotrophic lateral sclerosis type 6. *Science* 323, 1208-1211 (2009).

56. Ling, S. C., et al. ALS-associated mutations in TDP-43 increase its stability and promote TDP-43 complexes with FUS/TLS. *Proc Natl Acad Sci USA* 107, 13318-13323 (2010).

57. Voigt, A., et al. TDP-43-mediated neuron loss in vivo requires RNA-binding activity. *PLoS One* 5, e12247 (2010).

58. Douville, R., Liu, J., Rothstein, J. & Nath, A. Identification of active loci of a human endogenous retrovirus in neurons of patients with amyotrophic lateral sclerosis. *Ann Neurol* 69, 141-151 (2011).

59. Johnson, J. O., et al. Exome sequencing reveals VCP mutations as a cause of familial ALS. *Neuron* 68, 857-864 (2010).

60. Custer, S. K., Neumann, M., Lu, H., Wright, A. C. & Taylor, J. P. Transgenic mice expressing mutant forms VCP/p97 recapitulate the full spectrum of IBMPFD including degeneration in muscle, brain and bone. *Hum Mol Genet* 19, 1741-1755 (2010).

61. Badadani, M., et al. VCP associated inclusion body myopathy and paget disease of bone knock-in mouse model exhibits tissue pathology typical of human disease. *PLoS One* 5 (2010).

62. Maruyama, H., et al. Mutations of optineurin in amyotrophic lateral sclerosis. *Nature* 465, 223-226 (2010).

63. Development of a novel nonradiometric assay for nucleic acid binding to TDP-43 suitable for high-throughput screening using AlphaScreen technology. *J. Biomol Screen*, 15, 1099-1106 (2012).

Barbeito L H, Pehar M, Cassina P, Vargas M R, Peluffo H, Viera L, Estevez A G and Beckman J S. A role for astrocytes in motor neuron loss in amyotrophic lateral sclerosis. *Brain Res Brain Res Rev* 2004; 47:263-74.

Beaulieu J M, Kriz J and Julien J P. Induction of peripherin expression in subsets of brain neurons after lesion injury or cerebral ischemia. *Brain Res* 2002; 946:153-61.

Beaulieu J M, Nguyen M D and Julien J P. Late onset of motor neurons in mice overexpressing wild-type peripherin. *J Cell Biol* 1999; 147:531-44.

Bose J K, Wang I F, Hung L, Tarn W Y and Shen C K. TDP-43 overexpression enhances exon 7 inclusion during the survival of motor neuron pre-mRNA splicing. *J Biol Chem* 2008; 283:28852-9.

Buratti E, Dork T, Zuccato E, Pagani F, Romano M and Baralle F E. Nuclear factor TDP-43 and S R proteins promote in vitro and in vivo CFTR exon 9 skipping. *EMBO J* 2001; 20:1774-84.

Cairns N J, Neumann M, Bigio E H, Holm I E, Troost D, Hatanpaa K J, Foong C, White C L, 3rd, Schneider J A, Kretzschmar H A, Carter D, Taylor-Reinwald L, Paulsmeyer K, Strider J, Gitcho M, Goate A M, Morris J C, Mishra M, Kwong L K, Stieber A, Xu Y, Forman M S, Trojanowski J Q, Lee V M and Mackenzie I R. TDP-43 in familial and sporadic frontotemporal lobar degeneration with ubiquitin inclusions. *Am J Pathol* 2007; 171: 227-40.

Carpenter S. Proximal axonal enlargement in motor neuron disease. *Neurology* 1968; 18:841-51.

Corbo M and Hays A P. Peripherin and neurofilament protein coexist in spinal spheroids of motor neuron disease. *J Neuropathol Exp Neurol* 1992; 51:531-7.

Di Giorgio F P, Boulting G L, Bobrowicz S and Eggan K C. Human embryonic stem cell-derived motor neurons are sensitive to the toxic effect of glial cells carrying an ALS-causing mutation. *Cell Stem Cell* 2008; 3:637-48.

Di Giorgio F P, Carrasco M A, Siao M C, Maniatis T and Eggan K. Non-cell autonomous effect of glia on motor neurons in an embryonic stem cell-based ALS model. *Nat Neurosci* 2007; 10:608-14.

Forman M S, Trojanowski J Q and Lee V M. TDP-43: a novel neurodegenerative proteinopathy. *Curr Opin Neurobiol* 2007; 17:548-55.

Hodges J R, Davies R R, Xuereb J H, Casey B, Broe M, Bak T H, Kril J J and Halliday G M. Clinicopathological correlates in frontotemporal dementia. *Ann Neurol* 2004; 56:399-406.

Julien J P. ALS: astrocytes move in as deadly neighbors. *Nat Neurosci* 2007; 10:535-7.

Kabashi E, Valdmanis P N, Dion P, Spiegelman D, McConkey B J, Vande Velde C, Bouchard J P, Lacomblez L, Pochigaeva K, Salachas F, Pradat P F, Camu W, Meininger V, Dupre N and Rouleau G A. TARDBP mutations in individuals with sporadic and familial amyotrophic lateral sclerosis. *Nat Genet* 2008; 40:572-4.

Keller A F, Gravel M and Kriz J. Live imaging of amyotrophic lateral sclerosis pathogenesis: disease onset is characterized by marked induction of GFAP in Schwann cells. *Glia* 2009; 57:1130-42.

Keller A F, Gravel M and Kriz J. Treatment with minocycline after disease onset alters astrocyte reactivity and increases microgliosis in SOD1 mutant mice. *Exp Neurol* 2010.

Kriz J, Meier J, Julien J P and Padjen A L. Altered ionic conductances in axons of transgenic mouse expressing the human neurofilament heavy gene: A mouse model of amyotrophic lateral sclerosis. *Exp Neurol* 2000; 163:414-21.

Lagier-Tourenne C and Cleveland D W. Rethinking ALS: the FUS about TDP-43. *Cell* 2009; 136:1001-4.

Lomen-Hoerth C, Murphy J, Langmore S, Kramer J H, Olney R K and Miller B. Are amyotrophic lateral sclerosis patients cognitively normal? *Neurology* 2003; 60:1094-7.

Lu C H, Kalmar B, Malaspina A, Greensmith L and Petzold A. A method to solubilise protein aggregates for immunoassay quantification which overcomes the neurofilament "hook" effect. *J Neurosci Methods* 2011; 195:143-50.

Mercado P A, Ayala Y M, Romano M, Buratti E and Baralle F E. Depletion of TDP 43 overrides the need for exonic and intronic splicing enhancers in the human apoA-II gene. *Nucleic Acids Res* 2005; 33:6000-10.

Migheli A, Pezzulo T, Attanasio A and Schiffer D. Peripherin immunoreactive structures in amyotrophic lateral sclerosis. *Lab Invest* 1993; 68:185-91.

Nagai M, Re D B, Nagata T, Chalazonitis A, Jessell T M, Wichterle H and Przedborski S. Astrocytes expressing ALS-linked mutated SOD1 release factors selectively toxic to motor neurons. *Nat Neurosci* 2007; 10:615-22.

Noto Y I, Shibuya K, Sato Y, Kanai K, Misawa S, Sawai S, Mori M, Uchiyama T, Isose S, Nasu S, Sekiguchi Y, Fujimaki Y, Kasai T, Tokuda T, Nakagawa M and Kuwabara S. Elevated CSF TDP-43 levels in amyotrophic lateral sclerosis: Specificity, sensitivity, and a possible prognostic value. *Amyotroph Lateral Scler* 2010.

Ou S H, Wu F, Harrich D, Garcia-Martinez L F and Gaynor R B. Cloning and characterization of a novel cellular protein, TDP-43, that binds to human immunodeficiency virus type 1 TAR DNA sequence motifs. *J Virol* 1995; 69:3584-96.

Polymenidou M, Lagier-Tourenne C, Hutt K R, Huelga S C, Moran J, Liang T Y, Ling S C, Sun E, Wancewicz E, Mazur C, Kordasiewicz H, Sedaghat Y, Donohue J P, Shiue L, Bennett C F, Yeo G W and Cleveland D W. Long pre-mRNA depletion and RNA missplicing contribute to neuronal vulnerability from loss of TDP-43. *Nat Neurosci* 2011; 14:459-68.

Prut L, Abramowski D, Krucker T, Levy C L, Roberts A J, Staufenbiel M and Wiessner C. Aged APP23 mice show a delay in switching to the use of a strategy in the Barnes maze. *Behav Brain Res* 2007; 179:107-10.

Robertson J, Doroudchi M M, Nguyen M D, Durham H D, Strong M J, Shaw G, Julien J P and Mushynski W E. A neurotoxic peripherin splice variant in a mouse model of ALS. *J Cell Biol* 2003; 160:939-49.

Rutherford N J, Zhang Y J, Baker M, Gass J M, Finch N A, Xu Y F, Stewart H, Kelley B J, Kuntz K, Crook R J, Sreedharan J, Vance C, Sorenson E, Lippa C, Bigio E H, Geschwind D H, Knopman D S, Mitsumoto H, Petersen R C, Cashman N R, Hutton M, Shaw C E, Boylan K B, Boeve B, Graff-Radford N R, Wszolek Z K, Caselli R J, Dickson D W, Mackenzie I R, Petrucelli L and Rademakers R. Novel mutations in TARDBP (TDP-43) in patients with familial amyotrophic lateral sclerosis. *PLoS Genet* 2008; 4:e1000193.

Sanelli T, Xiao S, Horne P, Bilbao J, Zinman L and Robertson J. Evidence that TDP-43 is not the major ubiquitinated target within the pathological inclusions of amyotrophic lateral sclerosis. *Journal of neuropathology and experimental neurology* 2007; 66:1147-53.

Seeley W W. Selective functional, regional, and neuronal vulnerability in frontotemporal dementia. *Curr Opin Neurol* 2008; 21:701-7.

Stallings N R, Puttaparthi K, Luther C M and Elliott J L. Generation and characterization of wild-type and mutant TDP-43 transgenic mice. Society For Neuroscience, Abstract Book 2009; 2009.

Sterneck E, Kaplan D R and Johnson P F. Interleukin-6 induces expression of peripherin and cooperates with Trk receptor signaling to promote neuronal differentiation in PC12 cells. *J Neurochem* 1996; 67:1365-74.

Talbot K and Ansorge O. Recent advances in the genetics of amyotrophic lateral sclerosis and frontotemporal dementia: common pathways in neurodegenerative disease. *Hum Mol Genet* 2006; 15 Spec No 2:R182-7.

Van Deerlin V M, Leverenz J B, Bekris L M, Bird T D, Yuan W, Elman L B, Clay D, Wood E M, Chen-Plotkin A S, Martinez-Lage M, Steinbart E, McCluskey L, Grossman M, Neumann M, Wu I L, Yang W S, Kalb R, Galasko D R, Montine T J, Trojanowski J Q, Lee V M, Schellenberg G D and Yu C E. TARDBP mutations in amyotrophic lateral sclerosis with TDP-43 neuropathology: a genetic and histopathological analysis. *Lancet Neurol* 2008; 7:409-16.

Wong N K, He B P and Strong M J. Characterization of neuronal intermediate filament protein expression in cervical spinal motor neurons in sporadic amyotrophic lateral sclerosis (ALS). *J Neuropathol Exp Neurol* 2000; 59:972-82.

Xiao S, Tjostheim S, Sanelli T, McLean J R, Horne P, Fan Y, Ravits J, Strong M J and Robertson J. An aggregate-inducing peripherin isoform generated through intron retention is upregulated in amyotrophic lateral sclerosis and associated with disease pathology. *J Neurosci* 2008; 28:1833-40.

Yokoseki A, Shiga A, Tan C F, Tagawa A, Kaneko H, Koyama A, Eguchi H, Tsujino A, Ikeuchi T, Kakita A, Okamoto K, Nishizawa M, Takahashi H and Onodera O. TDP-43 mutation in familial amyotrophic lateral sclerosis. *Ann Neurol* 2008; 63:538-42.

Yum S W, Zhang J, Mo K, Li J and Scherer S S. A novel recessive Nefl mutation causes a severe, early-onset axonal neuropathy. *Ann Neurol* 2009; 66:759-70.

Zhang Y J, Xu Y F, Cook C, Gendron T F, Roettges P, Link C D, Lin W L, Tong J, Castanedes-Casey M, Ash P, Gass J, Rangachari V, Buratti E, Baralle F, Golde T E, Dickson D W and Petrucelli L. Aberrant cleavage of TDP-43 enhances aggregation and cellular toxicity. *Proc Natl Acad Sci USA* 2009; 106:7607-12.

What is claimed is:

1. A method for the diagnosis and treatment of a subject predisposed or suspected of developing amyotrophic lateral sclerosis (ALS), the method comprising the steps of:
contacting a TDP-43 polypeptide with an anti-TDP-43 polypeptide specific antibody in a biological sample of the subject;
contacting a NF-κB p65 polypeptide with an anti-NF-κB p65 polypeptide specific antibody in the biological sample;
detecting the level of interaction between the TDP-43 polypeptide and the NF-κB p65 polypeptide by ELISA, radioimmunoassay, immunoprecipitation assay, Western blot assay, electrophoretic mobility shift assay (EMSA) or immunostaining assay;
wherein detecting a level of interaction between TDP-43 polypeptide and NF-κB p65 polypeptide in the biological sample at least 1.5-fold higher than a reference level of interaction between TDP-43 polypeptide and NF-κB p65 polypeptide indicates that the subject is predisposed or suspected of developing ALS or is suffering from ALS;
diagnosing the subject predisposed or suspected of developing ALS or suffering from ALS;
treating the subject predisposed or suspected of developing ALS or suffering from ALS with an effective amount of a compound indicated for halting the progression of ALS or reducing the pathological manifestations of ALS;
wherein the reference level is the level in a subject not suffering from ALS;
wherein the TDP-43 polypeptide comprises the polypeptide of SEQ ID NO: 1;
wherein the NF-κB p65 polypeptide comprises the polypeptide of SEQ ID NO: 3.

2. The method of claim 1, wherein the level of interaction between TDP-43 polypeptide and NF-κB p65 polypeptide is at least 1.8-fold higher than the reference.

3. The method of claim 1, wherein the NF-κB p65 polypeptide interacts with the N-terminal portion of TDP-43 polypeptide.

4. The method of claim 1, wherein the NF-κB p65 polypeptide interacts with a RNA recognition motif (RRM) domain of TDP-43 polypeptide.

5. The method of claim 1, wherein the level of interaction between TDP-43 polypeptide and NF-κB p65 polypeptide is determined by ELISA.

6. The method of claim 1, wherein the biological sample is from blood, urine, cerebrospinal fluid, cortical neurons, microglial cells, myeloid cells or spinal cord extract.

7. The method of claim 1 wherein the determination of the level of interaction between TDP-43 polypeptide and NF-κB p65 polypeptide is repeated after a time interval in order to monitor the progression or regression of ALS, and wherein detecting an increased level of interaction between TDP-43 polypeptide and NF-κB p65 polypeptide over the time interval indicates a progression of ALS and wherein observing a decreased level of interaction between TDP-43 polypeptide and NF-κB p65 polypeptide over the time interval indicates a regression of ALS.

8. The method of claim 7, wherein the time interval is hourly, daily, weekly, monthly or yearly.

9. The method of claim 1 wherein the compound is a withanolide.

10. The method of claim 9 wherein the withanolide is withaferin A.

11. The method of claim 1 where the compound is an anti-TDP-43 antibody.

* * * * *

SEQUENCE LISTING

<160> NUMBER OF SEQ ID NOS: 31

<210> SEQ ID NO 1
<211> LENGTH: 414
<212> TYPE: PRT
<213> ORGANISM: Homo sapiens

<400> SEQUENCE: 1

```
Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
```

<210> SEQ ID NO 2
<211> LENGTH: 1728
<212> TYPE: DNA
<213> ORGANISM: Homo sapiens

<400> SEQUENCE: 2

```
gcgcttgggt ccgtcgctgc ttcggtgtcc ctgtcgggct tcccagcagc ggcctagcgg    60
gaaaagtaaa agatgtctga atatattcgg gtaaccgaag atgagaacga tgagcccatt   120
gaaataccat cggaagacga tgggacggtg ctgctctcca cggttacagc ccagtttcca   180
ggggcgtgtg ggcttcgcta caggaatcca gtgtctcagt gtatgagagg tgtccggctg   240
gtagaaggaa ttctgcatgc cccagatgct ggctggggaa atctggtgta tgttgtcaac   300
tatccaaaag ataacaaaag aaaaatggat gagacagatg cttcatcagc agtgaaagtg   360
aaaagagcag tccagaaaac atccgattta atagtgttgg gtctcccatg gaaaacaacc   420
gaacaggacc tgaaagagta ttttagtacc tttggagaag ttcttatggt gcaggtcaag   480
aaagatctta agactggtca ttcaaggggg tttggctttg tcgttttac ggaatatgaa   540
acacaagtga agtaatgtc acagcgacat atgatagatg gacgatggtg tgactgcaaa   600
cttcctaatt ctaagcaaag ccaagatgag cctttgagaa gcagaaaagt gtttgtgggg   660
cgctgtacag gggacatgac tgaggatgag ctgcgggagt tcttctctca gtacggggat   720
gtgatggatg tcttcatccc caagccattc agggcctttg cctttgttac atttgcagat   780
gatcagattg cgcagtctct tgtggagag gacttgatca ttaaaggaat cagcgttcat   840
atatccaatg ccgaacctaa gcacaatagc aatagacagt tagaaagaag tggaagattt   900
ggtggtaatc caggtggctt tgggaatcag ggtggatttg gtaatagcag aggggtgga   960
gctggtttgg gaaacaatca aggtagtaat atgggtggtg gatgaacttt tggtgcgttc  1020
agcattaatc cagccatgat ggctgccgcc caggcagcac tacagagcag ttggggtatg  1080
atgggcatgt tagccagcca gcagaaccag tcaggcccat cgggtaataa ccaaaaccaa  1140
ggcaacatgc agagggagcc aaaccaggcc ttcggttctg gaaataactc ttatagtggc  1200
tctaattctg gtgcagcaat tggttggga tcagcatcca atgcagggtc gggcagtggt  1260
tttaatggag gctttggctc aagcatggat tctaagtctt ctggctgggg aatgtagaca  1320
gtggggttgt ggttggttgg tatagaatgg tgggaattca aatttttcta aactcatggt  1380
aagtatattg taaatacat atgtactaag aattttcaaa attggtttgt tcagtgtgga  1440
gtatattcag cagtattttt gacatttttc tttggaaaaa gggagagcta aaggaatttt  1500
ataagttttg ttacatgaaa ggttgaaata ttgagtggtt gaaagtgaac tgctgtttgc  1560
ctgattggta aaccaacaca ctacaattga tatcaaaagg tttctcctgt aatattttat  1620
ccctggactt gtcaagtgaa ttctttgcat gttcaaaacg gaaaccattg attagaacta  1680
cattctttac cccttgtttt aatttgaacc ccaccatatg gatttttt                1728
```

<210> SEQ ID NO 3
<211> LENGTH: 551
<212> TYPE: PRT
<213> ORGANISM: Homo sapiens

<400> SEQUENCE: 3

```
Met Asp Glu Leu Phe Pro Leu Ile Phe Pro Ala Glu Pro Ala Gln Ala
1               5                   10                  15
```

-continued

```
Ser Gly Pro Tyr Val Glu Ile Ile Glu Gln Pro Lys Gln Arg Gly Met
            20              25              30

Arg Phe Arg Tyr Lys Cys Glu Gly Arg Ser Ala Gly Ser Ile Pro Gly
            35              40              45

Glu Arg Ser Thr Asp Thr Thr Lys Thr His Pro Thr Ile Lys Ile Asn
50              55              60

Gly Tyr Thr Gly Pro Gly Thr Val Arg Ile Ser Leu Val Thr Lys Asp
65              70              75              80

Pro Pro His Arg Pro His Pro His Glu Leu Val Gly Lys Asp Cys Arg
                85              90              95

Asp Gly Phe Tyr Glu Ala Glu Leu Cys Pro Asp Arg Cys Ile His Ser
            100             105             110

Phe Gln Asn Leu Gly Ile Gln Cys Val Lys Lys Arg Asp Leu Glu Gln
            115             120             125

Ala Ile Ser Gln Arg Ile Gln Thr Asn Asn Asn Pro Phe Gln Val Pro
130             135             140

Ile Glu Glu Gln Arg Gly Asp Tyr Asp Leu Asn Ala Val Arg Leu Cys
145             150             155             160

Phe Gln Val Thr Val Arg Asp Pro Ser Gly Arg Pro Leu Arg Leu Pro
            165             170             175

Pro Val Leu Pro His Pro Ile Phe Asp Asn Arg Ala Pro Asn Thr Ala
            180             185             190

Glu Leu Lys Ile Cys Arg Val Asn Arg Asn Ser Gly Ser Cys Leu Gly
            195             200             205

Gly Asp Glu Ile Phe Leu Leu Cys Asp Lys Val Gln Lys Glu Asp Ile
210             215             220

Glu Val Tyr Phe Thr Gly Pro Gly Trp Glu Ala Arg Gly Ser Phe Ser
225             230             235             240

Gln Ala Asp Val His Arg Gln Val Ala Ile Val Phe Arg Thr Pro Pro
            245             250             255

Tyr Ala Asp Pro Ser Leu Gln Ala Pro Val Arg Val Ser Met Gln Leu
            260             265             270

Arg Arg Pro Ser Asp Arg Glu Leu Ser Glu Pro Met Glu Phe Gln Tyr
            275             280             285

Leu Pro Asp Thr Asp Asp Arg His Arg Ile Glu Glu Lys Arg Lys Arg
            290             295             300

Thr Tyr Glu Thr Phe Lys Ser Ile Met Lys Lys Ser Pro Phe Ser Gly
305             310             315             320

Pro Thr Asp Pro Arg Pro Pro Arg Arg Ile Ala Val Pro Ser Arg
            325             330             335

Ser Ser Ala Ser Val Pro Lys Pro Ala Pro Gln Pro Tyr Pro Phe Thr
            340             345             350

Ser Ser Leu Ser Thr Ile Asn Tyr Asp Glu Phe Pro Thr Met Val Phe
            355             360             365

Pro Ser Gly Gln Ile Ser Gln Ala Ser Ala Leu Ala Pro Ala Pro Pro
            370             375             380

Gln Val Leu Pro Gln Ala Pro Ala Pro Ala Pro Ala Pro Ala Met Val
385             390             395             400

Ser Ala Leu Ala Gln Ala Pro Ala Pro Val Pro Val Leu Ala Pro Gly
            405             410             415

Pro Pro Gln Ala Val Ala Pro Ala Pro Lys Pro Thr Gln Ala Gly
            420             425             430

Glu Gly Thr Leu Ser Glu Ala Leu Leu Gln Leu Gln Phe Asp Asp Glu
```

```
                435                 440                 445
Asp Leu Gly Ala Leu Leu Gly Asn Ser Thr Asp Pro Ala Val Phe Thr
        450                 455                 460

Asp Leu Ala Ser Val Asp Asn Ser Glu Phe Gln Gln Leu Leu Asn Gln
465                 470                 475                 480

Gly Ile Pro Val Ala Pro His Thr Thr Glu Pro Met Leu Met Glu Tyr
            485                 490                 495

Pro Glu Ala Ile Thr Arg Leu Val Thr Gly Ala Gln Arg Pro Pro Asp
                500                 505                 510

Pro Ala Pro Ala Pro Leu Gly Ala Pro Gly Leu Pro Asn Gly Leu Leu
            515                 520                 525

Ser Gly Asp Glu Asp Phe Ser Ser Ile Ala Asp Met Asp Phe Ser Ala
        530                 535                 540

Leu Leu Ser Gln Ile Ser Ser
545                 550

<210> SEQ ID NO 4
<211> LENGTH: 1767
<212> TYPE: DNA
<213> ORGANISM: Homo sapiens

<400> SEQUENCE: 4
gaattccggc gaatggctcg tctgtagtgc acgccgcggg cccagctgcg accccggccc      60
cgcccccggg accccggcca tggacgaact gttcccctc atcttcccgg cagagccagc      120
ccaggcctct ggccctatg tggagatcat tgagcagccc aagcagcggg gcatgcgctt      180
ccgctacaag tgcgagggc gctccgcggg cagcatccca ggcgagagga gcacagatac      240
caccaagacc caccccacca tcaagatcaa tggctacaca ggaccaggga cagtgcgcat      300
ctccctggtc accaaggacc ctcctcaccg gcctcacccc acgagcttg taggaaagga      360 ctgccgggat ggcttctatg aggctgagct ctgcccggac cgctgcatcc acagtttcca      420
gaacctggga atccagtgtg tgaagaagcg ggacctggag caggctatca gtcagcgcat      480
ccagaccaac aacaacccct tccaagttcc tatagaagag cagcgtgggg actacgacct      540
gaatgctgtg cggctctgct ccaggtgac agtgcgggac ccatcaggca ggcccctccg      600
cctgccgcct gtccttcctc atcccatctt tgacaatcgt gccccaaca ctgccgagct      660 caagatctgc cgagtgaacc gaaactctgg cagctgcctc ggtggggatg agatcttcct      720
actgtgtgac aaggtgcaga agaggacat tgaggtgtat tcacgggac caggctggga      780 ggcccgaggc tccttttcgc aagctgatgt gcaccgacaa gtggccattg tgttccggac      840
ccctccctac gcagacccca gcctgcaggc tcctgtgcgt gtctccatgc agctgcggcg      900
gccttccgac cgggagctca gtgagcccat ggaattccag tacctgccag atacagacga      960
tcgtcaccgg attgaggaga aacgtaaaag gacatatgag accttcaaga gcatcatgaa      1020
gaagagtcct ttcagcggac ccaccgaccc ccggcctcca cctcgacgca ttgctgtgcc      1080
ttcccgcagc tcagcttctg tccccaagcc agcacccag cctatccct ttacgtcatc      1140 cctgagcacc atcaactatg atgagtttcc caccatggtg tttccttctg gcagatcag      1200 ccaggcctcg gccttggccc cggccctcc ccaagtcctg ccccaggctc agcccctgc      1260 ccctgctcca gccatggtat cagctctggc ccaggcccca gccctgtcc cagtcctagc      1320 cccaggccct cctcaggctg tggccccacc tgccccaag cccacccagg ctggggaagg      1380
aacgctgtca gaggccctgc tgcagctgca gtttgatgat gaagacctgg gggccttgct      1440
```

-continued

```
tggcaacagc acagacccag ctgtgttcac agacctggca tccgtcgaca actccgagtt    1500
tcagcagctg ctgaaccagg gcatacctgt ggccccccac acaactgagc ccatgctgat    1560
ggagtaccct gaggctataa ctcgcctagt gacaggggcc cagaggcccc ccgacccagc    1620
tcctgctcca ctgggggccc cggggctccc caatggcctc ctttcaggag atgaagactt    1680
ctcctccatt gcggacatgg acttctcagc cctgctgagt cagatcagct cctaaggggg    1740
tgacgcctgc cctccccaga gcactgg                                        1767
```

```
<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gcgggaaaag taaaagatgt c                                                21

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
attcctgcag cccgggggat cc                                               22

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
gagcgactgg ggttgagaag c                                                21

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
cccataggca ctgtcttctt tcacc                                            25

<210> SEQ ID NO 9
<211> LENGTH: 17
<212> TYPE: DNA
<213> ORGANISM: Artificial sequence
<220> FEATURE:
<223> OTHER INFORMATION: Primer

<400> SEQUENCE: 9
ctctttgtgg agaggac                                                     17

<210> SEQ ID NO 10
<211> LENGTH: 17
<212> TYPE: DNA
<213> ORGANISM: Artificial sequence
<220> FEATURE:
<223> OTHER INFORMATION: Primer
```

```
<400> SEQUENCE: 10
ccccaactgc tctgtag                                                   17

<210> SEQ ID NO 11
<211> LENGTH: 17
<212> TYPE: DNA
<213> ORGANISM: Artificial sequence
<220> FEATURE:
<223> OTHER INFORMATION: Primer

<400> SEQUENCE: 11
ctctttgtgg agaggac                                                   17

<210> SEQ ID NO 12
<211> LENGTH: 17
<212> TYPE: DNA
<213> ORGANISM: Artificial sequence
<220> FEATURE:
<223> OTHER INFORMATION: Primer

<400> SEQUENCE: 12
ttattacccg atgggca                                                   17

<210> SEQ ID NO 13
<211> LENGTH: 17
<212> TYPE: DNA
<213> ORGANISM: Artificial sequence
<220> FEATURE:
<223> OTHER INFORMATION: Primer

<400> SEQUENCE: 13
ctctttgtgg agaggac                                                   17

<210> SEQ ID NO 14
<211> LENGTH: 17
<212> TYPE: DNA
<213> ORGANISM: Artificial sequence
<220> FEATURE:
<223> OTHER INFORMATION: Primer

<400> SEQUENCE: 14
ggattaatgc tgaacgt                                                   17

<210> SEQ ID NO 15
<211> LENGTH: 26
<212> TYPE: DNA
<213> ORGANISM: Artificial sequence
<220> FEATURE:
<223> OTHER INFORMATION: Primer

<400> SEQUENCE: 15
gaaatgtccg ttcggttggc agaagc                                         26

<210> SEQ ID NO 16
<211> LENGTH: 27
<212> TYPE: DNA
<213> ORGANISM: Artificial sequence
<220> FEATURE:
<223> OTHER INFORMATION: Primer

<400> SEQUENCE: 16
ccaaaaccgt gatggaatgg aacaaca                                        27

<210> SEQ ID NO 17
```

```
<211> LENGTH: 21
<212> TYPE: RNA
<213> ORGANISM: Artificial sequence
<220> FEATURE:
<223> OTHER INFORMATION: siRNA

<400> SEQUENCE: 17
aggaaucagc gugcauauau u                                              21

<210> SEQ ID NO 18
<211> LENGTH: 21
<212> TYPE: RNA
<213> ORGANISM: Artificial sequence
<220> FEATURE:
<223> OTHER INFORMATION: siRNA

<400> SEQUENCE: 18
uauaugcacg cugauuccuu u                                              21

<210> SEQ ID NO 19
<211> LENGTH: 19
<212> TYPE: RNA
<213> ORGANISM: Artificial sequence
<220> FEATURE:
<223> OTHER INFORMATION: siRNA

<400> SEQUENCE: 19
gugcacauga gugagauuu                                                 19

<210> SEQ ID NO 20
<211> LENGTH: 19
<212> TYPE: RNA
<213> ORGANISM: Artificial sequence
<220> FEATURE:
<223> OTHER INFORMATION: siRNA

<400> SEQUENCE: 20
cacguguacu cacucuaaa                                                 19

<210> SEQ ID NO 21
<211> LENGTH: 24
<212> TYPE: DNA
<213> ORGANISM: Artificial sequence
<220> FEATURE:
<223> OTHER INFORMATION: ssDNA oligonucleotide

<400> SEQUENCE: 21
tgtgtgtgtg tgtgtgtgtg tgtg                                           24

<210> SEQ ID NO 22
<211> LENGTH: 16
<212> TYPE: DNA
<213> ORGANISM: Artificial sequence
<220> FEATURE:
<223> OTHER INFORMATION: ssDNA oligonucleotide

<400> SEQUENCE: 22
tgtgtgtgtg tgtgtg                                                    16

<210> SEQ ID NO 23
<211> LENGTH: 32
<212> TYPE: DNA
<213> ORGANISM: Artificial sequence
<220> FEATURE:
<223> OTHER INFORMATION: ssDNA oligonucleotide

<400> SEQUENCE: 23
```

-continued

```
ctgcttttg cctgtactgg gtctctgtgg tt                              32
```

<210> SEQ ID NO 24
<211> LENGTH: 12
<212> TYPE: DNA
<213> ORGANISM: Artificial sequence
<220> FEATURE:
<223> OTHER INFORMATION: ssDNA oligonucleotide

<400> SEQUENCE: 24

```
tgtgtgtgtg tg                                                   12
```

<210> SEQ ID NO 25
<211> LENGTH: 8
<212> TYPE: DNA
<213> ORGANISM: Artificial sequence
<220> FEATURE:
<223> OTHER INFORMATION: ssDNA oligonucleotide

<400> SEQUENCE: 25

```
tgtgtgtg                                                         8
```

<210> SEQ ID NO 26
<211> LENGTH: 24
<212> TYPE: DNA
<213> ORGANISM: Artificial sequence
<220> FEATURE:
<223> OTHER INFORMATION: ssDNA oligonucleotide

<400> SEQUENCE: 26

```
acacacacac acacacacac acac                                      24
```

<210> SEQ ID NO 27
<211> LENGTH: 24
<212> TYPE: RNA
<213> ORGANISM: Artificial sequence
<220> FEATURE:
<223> OTHER INFORMATION: ssRNA oligonucleotide

<400> SEQUENCE: 27

```
ugugugugug ugugugugug ugug                                      24
```

<210> SEQ ID NO 28
<211> LENGTH: 16
<212> TYPE: RNA
<213> ORGANISM: Artificial sequence
<220> FEATURE:
<223> OTHER INFORMATION: ssRNA oligonucleotide

<400> SEQUENCE: 28

```
ugugugugug ugugug                                               16
```

<210> SEQ ID NO 29
<211> LENGTH: 12
<212> TYPE: RNA
<213> ORGANISM: Artificial sequence
<220> FEATURE:
<223> OTHER INFORMATION: ssRNA oligonucleotide

<400> SEQUENCE: 29

```
ugugugugug ug                                                   12
```

<210> SEQ ID NO 30
<211> LENGTH: 12
<212> TYPE: RNA

```
<213> ORGANISM: Artificial sequence
<220> FEATURE:
<223> OTHER INFORMATION: ssRNA oligonucleotide

<400> SEQUENCE: 30
ucuuucuuuc uu                                                            12

<210> SEQ ID NO 31
<211> LENGTH: 24
<212> TYPE: RNA
<213> ORGANISM: Artificial sequence
<220> FEATURE:
<223> OTHER INFORMATION: ssRNA oligonucleotide

<400> SEQUENCE: 31
acacacacac acacacacac acac                                               24
```